(12) United States Patent
Mozayeni et al.

(10) Patent No.: US 7,604,599 B2
(45) Date of Patent: *Oct. 20, 2009

(54) SYSTEMS AND METHODS FOR USING DYNAMIC VASCULAR ASSESSMENT TO IMPROVE VASCULAR STENT PLACEMENT, APPLICATION, DESIGN AND MARKETING

(75) Inventors: B. Robert Mozayeni, Rockville, MD (US); Kevin E. Crutchfield, Potomac, MD (US); Simon Fitall, Bethesda, MD (US)

(73) Assignee: New Health Sciences, Inc., Bethesda, MD (US)

( * ) Notice: Subject to any disclaimer, the term of this patent is extended or adjusted under 35 U.S.C. 154(b) by 753 days.

This patent is subject to a terminal disclaimer.

(21) Appl. No.: 10/755,208

(22) Filed: Jan. 12, 2004

(65) Prior Publication Data
US 2005/0038342 A1 Feb. 17, 2005

Related U.S. Application Data

(63) Continuation-in-part of application No. 09/966,366, filed on Oct. 1, 2001, now Pat. No. 6,699,193.

(51) Int. Cl.
*A61B 8/00* (2006.01)
*A61B 8/14* (2006.01)
*A61B 5/02* (2006.01)

(52) U.S. Cl. .................. 600/454; 600/439; 600/457; 600/504

(58) Field of Classification Search ......... 600/453–457, 600/500, 504–506, 513; 73/861.25; 514/2
See application file for complete search history.

(56) References Cited

U.S. PATENT DOCUMENTS

5,510,077 A * 4/1996 Dinh et al. ................ 264/485

(Continued)

FOREIGN PATENT DOCUMENTS

EP 0573 249 A1 8/1993

(Continued)

OTHER PUBLICATIONS

Haude, M. et al "Intracoronary Doppler and Quantitative Coronary Angiography-Derived Predictors of MACE After Stent Implementation" Circulation 2001;103:1212.*

(Continued)

*Primary Examiner*—Eric F Winakur
*Assistant Examiner*—Michael T Rozanski
(74) *Attorney, Agent, or Firm*—Howrey LLP

(57) ABSTRACT

The invention relates to systems and methods for assessing blood flow in single or multiple vessels and segments, for assessing vascular health, for conducting clinical trials, for screening therapeutic interventions for effect, for assessing risk factors, for evaluating intracranial pressure and for analyzing the results in a defined manner. The invention enables direct monitoring of therapies, substances and devices on blood vessels, especially those of the cerebral vasculature. Relevant blood flow parameters include mean flow velocity, systolic acceleration, and pulsatility index. Measurement and analysis of these parameters, and others, provides details regarding the vascular health of individual and multiple vessels and a global analysis of an individual's overall vascular health. The invention is applicable as both a system and method for monitoring and improving the design, performance, marketing and use of vascular stents. In particular, the invention enables DVA-assisted stenting procedures, including both pre-operative and post-operative management.

19 Claims, 35 Drawing Sheets

U.S. PATENT DOCUMENTS

| | | | | |
|---|---|---|---|---|
| 5,534,007 | A * | 7/1996 | St. Germain et al. | 623/1.11 |
| 6,183,423 | B1 | 2/2001 | Gaumond et al. | |
| 6,254,628 | B1 * | 7/2001 | Wallace et al. | 623/1.12 |
| 6,656,122 | B2 * | 12/2003 | Davidson et al. | 600/454 |
| 6,692,443 | B2 * | 2/2004 | Crutchfield et al. | 600/504 |
| 6,697,667 | B1 * | 2/2004 | Lee et al. | 600/479 |
| 6,699,193 | B2 | 3/2004 | Crutchfield et al. | |
| 6,723,051 | B2 * | 4/2004 | Davidson et al. | 600/454 |
| 6,817,979 | B2 | 11/2004 | Nihtila | |
| 6,955,648 | B2 * | 10/2005 | Mozayeni et al. | 600/454 |
| 7,074,183 | B2 | 7/2006 | Castellanos | |
| 7,104,958 | B2 * | 9/2006 | Crutchfield et al. | 600/454 |
| 2002/0099291 | A1 | 7/2002 | Davidson et al. | 600/451 |
| 2004/0152984 | A1 * | 8/2004 | Crutchfield et al. | 600/454 |
| 2007/0016046 | A1 * | 1/2007 | Mozayeni et al. | 600/443 |

FOREIGN PATENT DOCUMENTS

| | | |
|---|---|---|
| WO | WO 99/12473 A | 3/1999 |
| WO | WO 99/52426 A | 10/1999 |

OTHER PUBLICATIONS

Hua Yang et al., *Transcranial Doppler Sonography Monitoring Cerebral Blood Flow and Embolism Signal In Percutaneous Transluminal Carotid Angioplasty and Stent*, Zhongguo Chaosheng Yixue Zazhi (Ultrasonic Medical Journal of China) 15 (9): pp. 700-702, 1999.

International Search Report dated Jun. 30, 2004.

Kelley R.E. et al. "Transcranial Doppler Ultrasonography of the Middle Cerebral Artery in the Hemodynamic Assessment of Internal Carotid Artery Stenosis" Arch. Neur., vol. 47, No. 9, Sep. 1990, pp. 960-964.

Paivansalo M. et al. "Effect of an Internal Carotid Stenosis on Orbital Blood Velocity" Acta Radiologica, Vo. 40, 1990, pp. 270-275.

Ralf Steinmeier, et al. "Cerebral Hemodynamics in Subarachnoid Hemorrhage Evaluated by Transcranial Doppler Sonograpphy. Part 2 . . . " Clinical Studies ; pp. 1-18; Department of Neurosurgery; Univ. of Erlangen-Nurnberg, Erlangen, Germany.

M. Aleksic, et al. "Pulsatility Index Determination by Flowmeter Measurement : A New Indicator for Vascular Resistance?" Eur. Sur. Res. 2004; 36; pp. 345-349.

Schmidt, B. et al "Noninvasive prediction of intracranial pressure curves using transcranial Doppler ultrasonography and bood pressure curves." Stroke; a Journal of Cerebral Circulation , Dec.1997, vol. 28, No. 12; pp. 2465-2472.

* cited by examiner

US Frequency = 2 mHz ($f_0$)

Received Frequency $f_2 > f_0$

Doppler Shift = $f_0 - f_2$
= 2MHz - $f_2$

Fig. 26

| Patient | | | | | | | | | | |
|---|---|---|---|---|---|---|---|---|---|---|
| Patient Id: | | Chart Nbr: | | Gender: | | Ethnic Group: | | | | |
| Full Name: | | | | DOB: | | | | | | |

| Stroke Risk | TCD Overview | TCD Readings | Bio/Health History |
|---|---|---|---|

Patient Id              Reading id

| Artery | Territory | Depth | Dir | Psv | Edv | Mfv | Norms | Sd | Pi | Ed Time | Ps Time | Sus | Sa |
|---|---|---|---|---|---|---|---|---|---|---|---|---|---|

Patient Id: [ ]
Reading Id: [ ]    PSV: [ ]    EDV: [ ]    MFV: [ ]    Norms: [ ]    SD: [ ]
Artery Id: [ ]
Territory: [ ]    PI: [ ]    ED Time: [ ]    PS Time: [ ]    SUS: [ ]    SA: [ ]
Depth: [ ]
Direction: [ ]

SYSTEMS AND METHODS FOR USING DYNAMIC VASCULAR ASSESSMENT TO IMPROVE VASCULAR STENT PLACEMENT, APPLICATION, DESIGN AND MARKETING

CROSS REFERENCE TO RELATED APPLICATIONS

This application is a continuation-in-part application claiming priority to, commonly assigned U.S. patent application Ser. No. 09/966,366 filed on Oct. 1, 2001 now U.S. Pat. No. 6,699,193 entitled "Decision Support Systems And Methods For Assessing Vascular Health" and also claims priority to U.S. Provisional Applications No. 60/438,990, filed Jan. 1, 2003. The above applications are expressly incorporated herein by reference in their entirety.

BACKGROUND OF THE INVENTION

1. Technical Field

The present invention relates generally to systems and methods for assessing vascular health and for assessing the effects of treatments, risk factors and substances, including therapeutic substances, on blood vessels, especially cerebral blood vessels, all achieved by measuring various parameters of blood flow in one or more vessels and analyzing the results in a defined matter. In addition, the present invention further pertains to collecting, analyzing, and using the measurement of various parameters of blood flow in one or more vessels to establish protocols for and to monitor clinical trials. Further, the present invention relates to an automated decision support system for interpreting the values of various parameters of blood flow in one or more vessels in assessing the vascular health of an individual.

2. Background Information

Proper functioning of the vascular system is essential for the health and fitness of living organisms. The vascular system carries essential nutrients and blood gases to all living tissues and removes waste products for excretion. The vasculature is divided into different regions depending on the organ systems served. If vessels feeding a specific organ or group of organs are compromised, the organs and tissues supplied by those vessels are deleteriously affected and may even fail completely.

Vessels, especially various types of arteries, not only transmit fluid to various locations, but are also active in responding to pressure changes during the cardiac cycle. With each contraction of the left ventricle of the heart during systole, blood is pumped through the aorta and then distributed throughout the body. Many arteries contain elastic membranes in their walls which assist in expansion of the vessel during systole. These elastic membranes also function in smoothing pulsatile blood flow throughout the vascular system. The vessel walls of such arteries often rebound following passage of the systolic pressure waveform.

In auto-regulation, cerebral blood vessels maintain constant cerebral blood flow by either constricting or dilating over a certain mean arterial blood pressure range so that constant oxygen delivery is maintained to the brain. Vascular failure occurs when the pressure drops too low and the velocity starts to fall. If the blood pressure gets too high and the vessels can no longer constrict to limit flow, then breakthrough, hyperemia breakthrough, and loss of auto-regulation occur. Both of these conditions are pathologic states, and have been described in the literature in terms of mean arterial pressure and cerebral blood flow velocity. But there are outliers that could not be explained based on that model. The failure of the model is that it relies upon systemic blood pressure; the pressure of blood in the brain itself is not being measured directly. The resultant pressure curve has an S-shaped curve.

The force applied to the blood from each heart beat is what drives it forward. In physics, force is equivalent to mass times acceleration. But when blood is examined on a beat to beat variation, each heartbeat delivers about the same mass of blood, unless there is severe loss of blood or a very irregular heart rhythm. Therefore, as a first approximation, the force of flow on the blood at that particular moment is directly proportional to its acceleration.

Diseased blood vessels lose the ability to stretch. The elasticity or stretch of the blood vessel is very critical to maintaining pulsatile flow. When a muscle is stretched, it is not a passive relaxation. There is a chemical reaction that happens within the muscle itself that causes a micro-contracture to increase the constriction, so that when a bolus of blood comes through with each heartbeat, it stretches the blood vessel wall, but the blood vessel then contracts back and gives the kick forward to maintain flow over such a large surface area with the relatively small organ of the heart. This generates a ripple of waves, starting in the large vessel of the aorta and working its way through the rest of the vessels. As vessels become diseased, they lose the ability to maintain this type of pulsatile flow.

Further, if vessels are compromised due to various factors such as narrowing or stenosis of the vessel lumen, blood flow becomes abnormal. If narrowing of a vessel is extensive, turbulent flow may occur at the stenosis resulting in damage to the vessel. In addition, blood may not flow adequately past the point of stenosis, thereby injuring tissues distal to the stenosis. While such vascular injuries may occur anywhere throughout the body, the coronary and cerebral vascular beds are of supreme importance for survival and well-being of the organism. Narrowing of the coronary vessels supplying the heart may decrease cardiovascular function and decrease blood flow to the myocardium, leading to a heart attack. Such episodes may result in significant reduction in cardiac function and death.

Abnormalities in the cerebral vessels may prevent adequate blood flow to neural tissue, resulting in transient ischemic attacks (TIAs), migraines and stroke. The blood vessels which supply the brain are derived from the internal carotid arteries and the vertebral arteries. These vessels and their branches anastomose through the great arterial circle, also known as the Circle of Willis. From this circle arise the anterior, middle and posterior cerebral arteries. Other arteries such as the anterior communicating artery and the posterior communicating artery provide routes of collateral flow through the great arterial circle. The vertebral arteries join to form the basilar artery, which itself supplies arterial branches to the cerebellum, brain stem and other brain regions. A blockage of blood flow within the anterior cerebral artery, the posterior cerebral artery, the middle cerebral artery, or any of the other arteries distal to the great arterior circle results in compromised blood flow to the neural tissue supplied by that artery. Since neural tissue cannot survive without normal, constant levels of glucose and oxygen within the blood and provided to neurons by glial cells, blockage of blood flow in any of these vessels leads to death of the nervous tissue supplied by that vessel.

Strokes result from blockage of blood flow in cerebral vessels due to constriction of the vessel resulting from an embolus or stenosis. Strokes may also arise from tearing of the vessel wall due to any number of circumstances. Accordingly, a blockage may result in ischemic stroke depriving neural tissue distal to the blockage of oxygen and glucose. A tearing or rupture of the vessel may result in bleeding into the brain, also known as a hemorrhagic stroke. Intracranial bleeding exerts deleterious effects on surrounding tissue due to increased intracranial pressure and direct exposure of neurons to blood.

Regardless of the cause, stroke is a major cause of illness and death. Stroke is the leading cause of death in women and kills more women than breast cancer. Currently, more than three quarters of a million people in the United States experience a stroke each year, and more than 25 percent of these individuals die. Approximately one-third of individuals suffering their first stroke die within the following year. Furthermore, about one-third of all survivors of a first stroke experience additional strokes within the next three years.

In addition to its terminal aspect, stroke is a leading cause of disability in the adult population. Such disability can lead to permanent impairment and decreased function in any part of the body. Paralysis of various muscle groups innervated by neurons affected by the stroke can lead to confinement to a wheel chair, and muscular spasticity and rigidity. Strokes leave many patients with no ability to communicate either orally or by written means. Often, stroke patients are unable to think clearly and have difficulties naming objects, interacting with other individuals, and generally operating in society.

Strokes also result in massive expenditures of resources throughout society, and place a tremendous economic burden on affected individuals and their families. It is estimated that the annual total costs in the United States economy alone is over $30 billion per year, with the average acute care stroke treatment costing approximately $35,000. As the population increases in age, the incidence of stroke will rise dramatically. In fact, the risk of stroke doubles with ever succeeding decade of life. Since the life expectancy of the population has increased dramatically during the last 100 years, the number of individuals over 50 years old has risen precipitously. In this population of individuals living to ages never before expected, the potential for stroke is very high indeed. Accordingly, the financial and emotional impact of cerebral vascular damage is expected to dramatically increase during the next several decades.

Despite the tremendous risk of stroke, there are presently no convenient and accurate methods to access vascular health. Many methods rely on invasive procedures, such as arteriograms, to determine whether vascular stenosis is occurring. These invasive techniques are often not ordered until the patient becomes symptomatic. For example, carotid arteriograms may be ordered following a physical examination pursuant to the appearance of a clinical symptom. Performing an arteriogram is not without risks due to introducing dye materials into the vascular system that may cause allergic responses. Arteriograms also use catheters that can damage the vascular wall and dislodge intraluminal plaque, which can cause an embolic stroke at a downstream site.

Many methods and devices available for imaging cerebral vessels do not provide a dynamic assessment of vascular health. Instead, these imaging procedures and equipment merely provide a snapshot or static image of a vessel at a particular point in time. Cerebral angiography is conventionally held to be the "gold standard" of analyzing blood flow to the brain. But this invasive method of analysis only provides the shape of the vessels in an imaging modality. To obtain the same type of flow criteria from an angiogram as one obtains from the present invention would entail extraordinary efforts and multiple dangerous procedures.

Instruments have been developed to obtain noninvasive measurements of blood velocity in anterior arteries and veins using Doppler principles. In accordance with known Doppler phenomenon, these instruments provide an observer in motion relative to a wave source a wave from the source that has a frequency different from the frequency of the wave at the source. If the source is moving toward the observer, a higher frequency wave is received by the observer. Conversely, if the wave source is moving away from the observer, a lower frequency wave is received. The difference between the emitted and received frequencies is known as the Doppler shift. This Doppler technique may be accomplished through the use of ultrasound energy.

The operation of such instruments in accordance with the Doppler principle may be illustrated with respect to FIGS. 1 to 4. In FIG. 1, the ultrasound probe 40 acts as a stationary wave source, emitting pulsed ultrasound at a frequency of, e.g., 2 MHz. This ultrasound is transmitted through the skull 41 and brain parenchyma to a blood vessel 42. For purposes of illustration, a blood cell 43 is shown moving toward the probe and acts as a moving observer. As illustrated in FIG. 2, the blood cell reflects the pulse of ultrasound and can be considered a moving wave source. The probe receives this reflected ultrasound, acting as a stationary observer. The frequency of the ultrasound received by the probe, $f_1$ is higher than the frequency, $f_0$, originally emitted. The Doppler shift of the received wave can then be calculated. FIGS. 3 and 4 show the effect on a pulse of ultrasound when blood flows in a direction away from the probe. In this case, the received frequency, $f_2$, reflected from the blood cell, is lower than the emitted frequency $f_0$. Again, the Doppler shift can be calculated.

The Doppler effect can be used to determine the velocity of blood flow in the cerebral arteries. For this purpose, the Doppler equation used is the following:

$$F_d = \frac{2 F_t V \cos \Theta}{V_o}$$

where
$F_d$=Doppler frequency shift
$F_t$=Frequency of the transmitter
V=Velocity of blood flow
$\Theta$=Angle of incidence between the probe and the artery
$V_o$=Velocity of ultrasound in body tissue Typically, $F_t$ is a constant, e.g., 2, 4 or 8 MHz, and $V_0$ is approximately 1540 meters second (m/s) in soft body tissue. Assuming that there is a zero angle of incidence between the probe and the artery, the value of cos $\Theta$ is equal to 1. The effect of the angle $\Theta$ is only significant for angles of incidence exceeding 30°.

In exemplary instruments, ultrasonic energy is provided in bursts at a pulse repetition rate or frequency. The probe receives the echoes from each burst and converts the sound energy to an electrical signal. To obtain signal data corresponding to reflections occurring at a specific depth (range) within the head, an electronic gate opens to receive the reflected signal at a selected time after the excitation pulse, corresponding to the expected time of arrival of an echo from a position at the selected depth. The range resolution is generally limited by the bandwidth of the various components of the instrument and the length of the burst. The bandwidth can be reduced by filtering the received signal, but at the cost of an increased length of sample volume.

Other body movements, for example, vessel wall contractions, can also scatter ultrasound, which will be detected as "noise" in the Doppler signal. To reduce this noise interference, a high pass filter is used to reduce the low frequency, high amplitude signals. The high pass filter typically can be adjusted to have a passband above a cutoff frequency selectable between, e.g., about 0 and about 488 Hz.

Many health care providers rarely have such flow diagnostic capabilities at their disposal. For example, health care providers may be situated in remote locations such as in rural areas, on the ocean or in a battlefield situation. These health care providers need access to analytical capabilities for analysis of flow data generated at the remote location. Health care providers facing these geographic impediments are limited in their ability to provide the high quality medical services needed for their patients, especially on an emergency basis. Further, both physicians and individuals concerned for their own health are often limited in their ability to consult with specialists in specific medical disciplines. Accordingly, a system that facilitates access of physicians in various locations to sophisticated medical diagnostic and prognostic capabilities concerning vascular health is needed. Such access would promote delivery of higher quality health care to individuals located throughout the country, especially in remote areas removed from major medical centers.

There is also a need for a system whereby patient vascular data can be transmitted to a central receiving facility, which receives the data, analyzes it, produces a value indicative of the state of vascular health, and then transmit this information to another location, such as the originating data transmitting station, or perhaps directly to the health care provider's office. This system should provide access to sophisticated computing capabilities that would enhance the accuracy of health care providers' diagnostic and prognostic capabilities concerning vascular health. This system should be able to receive high volumes of patient data and rapidly process the data in order to obtain diagnoses and prognoses of disease. Such a system could be used for diagnosis and prognosis of any disease or condition related to vascular health.

There is a further need for a system that facilitates the ability of a health care provider to conveniently and rapidly transmit vascular flow data parameters obtained from a patient to a location where consistent, reproducible analysis is performed. The results of the analysis can then be transmitted to the health care provider to facilitate accurate diagnosis or prognosis of a patient, to recommend treatment options, and to discuss the ramifications of those treatment options with the patient.

There is also a need for a system that enables health care providers to measure the rate and type of developing vascular disease, and to recommend interventions that prevent, minimize, stabilize or reverse the disease.

There is a further need for a system that enables health care providers to predict the vascular reaction to a proposed therapeutic intervention, and to modify the proposed therapeutic intervention if a deleterious or adverse vascular response is anticipated. Physicians often prescribe therapeutic substances for patients with conditions related to the cardiovascular system that may affect vascular health. For example, hypertensive patients may be prescribed beta-blockers with the intent of lowering blood pressure, thereby decreasing the probability of a heart attack. Patients frequently receive more than one therapeutic substance for their condition or conditions. The potential interaction of therapeutic substances at a variety of biological targets, such as blood vessels, is often poorly understood. Therefore, a non-invasive method that can be used to assess the vascular effects of a substance, such as a therapeutic substance, or a combination of therapeutic substances is needed. A clear understanding of the vascular effects of one or more substances on blood vessels may prevent prescriptions of substances with undesirable and potentially lethal effects, such as stroke, vasospasm and heart attack. Accordingly, what is needed is a system and method that can be used for repeated assessment without deleterious effects of potential vascular effects of a substance, or combination of substances, in a patient population during a clinical trial. Such clinical studies may also reveal dosages of individual substances and combinations of substances at specific dosages that provide desirable and unexpected effects on blood vessels.

Furthermore, a system and method that can provide an assessment of the vascular health of an individual is needed. Also needed is a system and method that may be used routinely to assess vascular health, such as during periodic physical examinations. This system and method preferably is non-invasive and provides information concerning the compliance and elasticity of a vessel. Also needed is a system and method that may be used to rapidly assess the vascular health of an individual. Such systems and methods should be available for use in routine physical examinations, and especially in the emergency room, intensive care unit or in neurological clinic. What is also needed is a system and method which can be applied in a longitudinal manner for each individual so that the vascular health of the individual may be assessed over time. In this manner, a problem or a disease process may be detected before the appearance of a major cerebral vascular accident or stroke.

In addition, there is a need for a system and method for assessing whether treatments, risk factors and substances affect blood vessels, particularly cerebral blood vessels, so that their potential for causing vascular responses may be determined. By determining the vascular effects of treatments, risk factors and substances, physicians may recommend that a patient avoid the treatment, risk factor and/or substance. Alternatively, desirable vascular effects of a treatment, therapeutic intervention and/or substance may result in administration of the treatment, therapeutic intervention and/or substance to obtain a desired effect.

In addition, there is also needed a system and method for assessing the efficacy of a treatment, including conducting a procedure, carrying out a therapy, and administering a pharmaceutical substance, in treating vascular disorders, so that identification of those treatments most efficacious in the treatment of vascular disorders can be determined and employed to restore vascular health.

As required by federal regulations, treatments, including drugs and other therapies intended for treating individuals, have to be tested in people. These tests, called clinical trials, provide a variety of information regarding the efficacy of treatment, such as whether it is safe and effective, at what doses it works best, and what side effects it causes. This information guides health professionals and, for nonprescription drugs, consumers in the proper use of medicines. In controlled clinical trials, results observed in patients being administered a treatment are compared to results from similar patients receiving a different treatment such as a placebo or no treatment at all. Controlled clinical trials are the only legal basis for the United States Food and Drug Administration ("FDA") in determining that a new treatment provides "substantial evidence of effectiveness, as well as confirmation of relative safety in terms of the risk-to-benefit ratio for the disease that is to be treated."

It is important to test drugs, therapies, and procedures in those individuals that the treatments are intended to help. It is also important to design clinical studies that ask and answer the right questions about investigational treatment. Before clinical testing is initiated, researchers analyze a treatment's main physical and chemical properties in the laboratory and study its pharmacological and toxic effects on laboratory animals. If the results from the laboratory research and animal studies show promise, the treatment sponsor can apply to the FDA to begin testing in people. Once the FDA has reviewed the sponsor's plans and a local institutional review board—typically a panel of scientists, ethicists, and nonscientists that oversees clinical research at medical centers—approves the protocol for clinical trials, clinical investigators give the treatment to a small number of healthy volunteers or patients. These Phase 1 studies assess the most common acute adverse effects and examine the size of doses that patients can take safely without a high incidence of side effects. Initial clinical studies also begin to clarify what happens to a drug in the human body, e.g., whether it's changed, how much of it is absorbed into the bloodstream and various organs, how long it is retained within the body, how the body rids the drug, and the effect(s) of the drug on the body.

If Phase 1 studies do not reveal serious problems, such as unacceptable toxicity, a clinical study is then conducted wherein the treatment is given to patients who have the condition that the treatment is intended to treat. Researchers then assess whether the treatment has a favorable effect on the condition. The process for the clinical study simply requires recruiting one or more groups of patients to participate in a clinical trial, administering the treatment to those who agree to participate, and determining whether the treatment helps them.

Treatments usually do not miraculously reverse fatal illnesses. More often, they reduce the risk of death but do not entirely eliminate it. This is typically accomplished by relieving one or more symptoms of the illness, such as nasal stuffiness, pain, or anxiety. A treatment may also alter a clinical measurement in a way that physicians consider to be valuable, for example, reduce blood pressure or lower cholesterol. Such treatment effects can be difficult to detect and evaluate. This is mainly because diseases do not follow a predictable path. For example, many acute illnesses or conditions, such as viral ailments like influenza, minor injuries, and insomnia, go away spontaneously without treatment. Some chronic conditions like arthritis, multiple sclerosis, or asthma often follow a varying course, e.g., better for a time, then worse, then better again, usually for no apparent reason. Heart attacks and strokes have widely variable death rates depending on treatment, age, and other risk factors, making the "expected" mortality for an individual patient hard to predict.

A further difficulty in gauging the effectiveness of an investigational treatment is that in some cases, measurements of disease are subjective, relying on interpretation by the physician or patient. In those circumstances, it's difficult to tell whether treatment is having a favorable effect, no effect, or even an adverse effect. The way to answer critical questions about an investigational treatment is to subject it to a controlled clinical trial.

In a controlled trial, patients in one group receive the investigational treatment. Those in a comparable group, the control group, receives either no treatment at all, a placebo (an inactive substance that looks like the investigational drug), or a treatment known to be effective. The test and control groups are typically studied at the same time. Usually, the same group of patients is divided into two sub-groups, with each subgroup receiving a different treatment.

In some special cases, a study uses a "historical control," in which patients given the investigational treatment are compared with similar patients treated with the control treatment at a different time and place. Often, patients are examined for a period of time after treatment with an investigational treatment, with the investigators comparing the patients' status both before and after treatment. Here, too, the comparison is historical and based on an estimate of what would have happened without treatment. The historical control design is particularly useful when the disease being treated has high and predictable death or illness rates. It is important that treatment and control groups be as similar as possible in characteristics that can affect treatment outcomes. For example, all patients in a specific group must have the disease the treatment is meant to treat or the same stage of the disease. Treatment and control groups should also be of similar age, weight, and general health status, and similar in other characteristics that could affect the outcome of the study, such as other treatment(s) being received at the same time.

A principal technique used in controlled trials is called "randomization." Patients are randomly assigned to either the treatment or control group rather than deliberately selected for one group or the other. An important assumption, albeit a seriously flawed one, is that when the study population is large enough and the criteria for participation are carefully defined, randomization yields treatment and control groups that are similar in important characteristics. Because assignment to one group or another is not under the control of the investigator, randomization also eliminates the possibility of "selection bias," the tendency to pick healthier patients to get the new treatment or a placebo. In a double-blind study, neither the patients, the investigators, nor the data analysts know which patients got the investigational drug.

Unfortunately, careful definition of selection criteria for matching participation in clinical trials has not been conventionally available. Vascular health, and more particularly cerebrovascular health, has been a criterion that has been difficult, if not impossible, to assess for possible clinical trial participants. Thus, there remains a need in the art for the ability to truly randomize clinical trials by choosing trial participants with matched vascular and cerebrovascular characteristics.

Moreover, an important aspect of clinical trials is to assess the risk of adverse effects of a given treatment. This can be difficult for adverse effects that manifest themselves only long after the short run of a clinical trial has run its course. Unfortunately, vascular effects, and more particularly cerebrovascular adverse effects, are difficult, if not impossible, to assess during the course of a clinical trial. Thus, there remains a need in the art for the ability to accurately assess adverse effects brought about by a treatment upon vascular and cerebrovascular health characteristics.

There is also needed a system and method for assessing the efficacy of a treatment, including conducting a procedure, carrying out a therapy, and administering a pharmaceutical substance or combinations thereof in treating vascular disorders, so that identification of deleterious treatments can be determined and no longer be prescribed.

Further, there is a need for a system and method for assessing the impact of a treatment, including conducting a procedure, carrying out a therapy, and administering a pharmaceutical substance, or combinations of pharmaceutical substances, upon vascular health, so that the impact of a treatment which have an effect upon vascular health can be ascertained.

SUMMARY OF THE INVENTION

The present invention provides a solution to the above-described shortcomings by providing a system and method for assessing the vascular health of an individual. This system and method is inexpensive, rapid, non-invasive, and provides superior data concerning the dynamic function of the vasculature. Accordingly, this system and method may be used in a wide variety of situations including, but not limited to, periodic physical examinations, in an intensive care unit, in an emergency room, in the field such as in battlefield situations or at the scene of an emergency on the highway or in the country, and in a neurological clinic. The use of this system and method enables physicians to evaluate individuals not only for their current state of vascular health, but also to detect any deviations from vascular health by evaluating specific parameters of vascular function.

In addition to use during routine physical examinations, the present system and method may be used to evaluate individuals with the risk factors for cerebral vascular malfunction. Such risk factors include, but are not limited to a prior history of stroke, a genetic predisposition to stroke, smoking, alcohol consumption, caffeine consumption, obesity, hypertension, aneurysms, arteritis, transient ischemic episodes (TIAs), closed head injury, history of migraine headaches, prior intracranial trauma, increased intracranial pressure, and history of drug abuse.

In addition to providing a system and method for evaluating individuals with high risk factors, the present system and method also provides a mechanism for selecting patient groups for clinical trials and monitoring patient populations in specific clinical groups. For example, a patient population of individuals at high risk of stroke may be evaluated systematically over time to determine whether ongoing vascular changes may indicate an incipient cerebral vascular event, such as stroke. In this manner, it may be possible to predict the occurrence of a first stroke, thereby preventing the stroke. In another embodiment, the present invention provides a mechanism for monitoring individuals who have experienced a stroke.

In yet a further embodiment of the present invention, the vascular reactivity of an individual to various substances, including but not limited to drugs, nutrients, alcohol, nicotine, caffeine, hormones, cytokines and other substances, may be evaluated. Through the use of this system and method, research studies may be conducted using animals or humans to evaluate the effects of various substances on the vascular system. By performing the noninvasive, low cost and efficient tests of the present invention, valuable information concerning the potential vascular effects of a substance may be collected and assessed before the substance is medically prescribed. Furthermore, vascular effects of dosages of individual substances and combinations of substances at different dosages may be evaluated in selected clinical populations using the system and method of the present invention. Accordingly, the present invention provides a system and method for performing non-invasive clinical research studies to evaluate potential vascular effects of substances, or combinations of substances, at selected dosages and in selected patient populations.

In another embodiment, the present invention may be applied to specific populations of individuals who have had specific illnesses to determine whether application of a substance may produce undesirable effects in that population. For example, a population of diabetic individuals may react differently to a specific substance such as a drug than a non-diabetic population. Further, a population of hypertensive individuals may react differently to a specific substance, such as a catecholaminergic agonist drug or an ephedrine-containing natural extract, than a non-hypertensive population. The use of the present invention permits an assessment of vascular reactivity in any individual or any population, whether it be a population of individuals with specific diseases, conditions or prior exposures to various therapies.

By means of the present invention, a method of assessing vascular health in a human or an animal is provided. In one embodiment, this assessment method comprises the steps of obtaining information concerning flow velocity within a vessel; calculating a mean flow velocity value for the vessel; calculating a systolic acceleration value for the vessel; and inserting the mean flow velocity value and the systolic acceleration value into a schema for further analysis of the calculated values. Such schema can consist of multiple arrangements of such values, including but not limited to diagrams, graphs, nomograms, spreadsheets and databases, thereby permitting operations such as mathematical calculations, comparisons and ordering to be performed that include the calculated values.

In one embodiment, the assessment method may further comprise calculating a pulsatility index. With the pulsatility index calculated, the assessment method of is able to plot the pulsatility index, the systolic acceleration value, and the mean flow velocity value for the vessel in a 3-dimensional space, wherein the plot of the pulsatility index, the systolic acceleration value, and the mean flow velocity value in 3-dimensional space produce a first characteristic value for the vessel. This first characteristic value for the vessel may then be compared to other first characteristic values obtained from measurements of flow velocity collected from similar vessels from other humans or animals to determine whether the vessel is in an auto-regulation mode.

The assessment method may further comprise collecting information concerning an additional variable, transforming the information into a value, and plotting the value in n-dimensional space together with the pulsatility index, the systolic acceleration value, and the mean flow velocity value to produce a second characteristic value for the vessel. The second characteristic value can then be compared to second characteristic values obtained from measurements of flow velocities collected from similar vessels from other humans or animals to determine whether the vessel is in an auto-regulation mode.

The vessel of the assessment method as described above can be an intracranical vessel. Further, the vessel can be an artery. The artery can be one that supplies the central nervous system. Further, the artery can be selected from the group consisting of the common carotid, internal carotid, external carotid, middle cerebral, anterior cerebral, posterior cerebral, anterior communicating, posterior communicating, vertebral, basilar, ophthalmic, and branches thereof.

The information collected in the assessment method described above concerning flow velocity can be gathered using ultrasound energy. This gathering of flow velocity information can further be gathered by use of a Doppler probe.

The effects of a substance on a vessel can be determined by applying the assessment method as described above both before and after administering the substance. This substance can be a drug. The drug may be a vasoactive drug. The substance may be suspected of having vascular activity.

The assessment method described above may be utilized in the instance wherein the human or the animal is suspected of having or has a vascular disease or a condition that affects vascular function. The human or the animal can be analyzed at a time of normal and at a time of abnormal health.

The present invention further provides for a method of assessing vascular effects of a treatment in a human or an animal. This method includes the steps of collecting a first set of information concerning flow velocity within a vessel; administering the drug; collecting a second set of information concerning flow velocity within the vessel; calculating a mean flow velocity value for the vessel; calculating a systolic acceleration value for the vessel; and inserting the mean flow velocity value and the systolic acceleration value into a schema for analysis of the calculated values.

The step of administering a treatment in the vascular effects assessment method can be selected from the group consisting of administering a drug, conducting a procedure, and carrying out a therapy. When the administration comprises administering a drug, the drug may include a statin. The statin administered can include Atorvastatin calcium.

The steps of collecting the first set of information and collecting the second set of information in the vascular assessment method described above can be performed using ultrasound energy. More specifically, the collection steps can be performed using a Doppler probe.

The present invention further provides for a method of assessing vascular effects of a treatment in a human or an animal. The treatment can include conducting a procedure, carrying out a therapy, and administering a drug. This method includes the steps of collecting a first set of information concerning flow velocity within a vessel; obtaining a first mean flow velocity value before administration of the treatment; obtaining a first systolic acceleration value before administration of the treatment; administering the treatment; collecting a second set of information concerning flow velocity within the vessel; obtaining a second mean flow velocity value following administration of the treatment; obtaining a second systolic acceleration value after administration of the treatment; comparing the first mean flow velocity value and the second mean flow velocity value; and comparing the first systolic acceleration value and the second systolic acceleration value to determine if the treatment had a vascular effect.

The method of assessing the vascular effects of a treatment as described above may further include the steps of calculating a first pulsatility index from the first set of information; calculating a second pulsatility index from the second set of information; plotting the first pulsatility index, the first mean flow velocity value, and the first systolic acceleration value to produce a first characteristic value for the vessel; plotting the second pulsatility index, the second mean flow velocity value and the second systolic acceleration value to produce a second characteristic value for the vessel; and comparing the first characteristic value and the second characteristic value to determine if the drug had a vascular effect.

The step of administering a treatment in the method of assessing vascular effects of a treatment as described above can be selected from the group consisting of administering a drug, conducting a procedure, and carrying out a therapy. When the administration includes administering a drug, the drug can include a statin. When a statin is administered, the statin can include Atorvastatin calcium.

The steps of collecting the first set of information and collecting the second set of information in the method of assessing vascular effects of a treatment as described above can be performed using ultrasound energy. More specifically, the collection can be performed by means of a Doppler probe.

The method of assessing vascular effects of a treatment as described above may be used when the human or the animal has a risk factor for a stroke. The human or the animal may have received at least one medication before collecting the first set of information.

The method of assessing vascular effects of a treatment as described above may be used to determine if the drug may cause undesirable vascular effects in the human or the animal receiving the medication.

The method of assessing vascular effects of a drug as described above can be used when the human or the animal has a vascular disease or a condition that affects vascular function.

In another embodiment of the present invention, a method of assessing vascular effects of a treatment in humans or animals is provided. The method of accessing the vascular effects includes assigning individual humans or animals to different groups for each human or animal by performing the steps of obtaining a first set of information concerning flow velocity within a vessel; obtaining a first mean flow velocity value before administration of the drug; obtaining a first systolic acceleration value before administration of the treatment; administering the treatment; obtaining a second set of information concerning flow velocity within the vessel; obtaining a second mean flow velocity value following administration of the treatment; obtaining a second systolic acceleration value after administration of the treatment; comparing the first mean flow velocity value and the second mean flow velocity value; comparing the first systolic acceleration value and the second systolic acceleration value to determine if the treatment had a vascular effect; and statistically analyzing data for each individual before and after administration of the treatment.

The administration of the treatment in the method of assessing vascular effects of a treatment by assigning individual humans or animals to different groups as described above can be selected from the group consisting of administering a drug, conducting a procedure, and carrying out a therapy. When the administration of a drug is selected, the drug may include a statin. The statin can be Atorvastatin calcium.

The data collection step in the method of assessing vascular effects of a treatment by assigning individual humans or animals to different groups as described above can be performed using ultrasound energy. Further, the data collection step can be performed using a Doppler probe.

The method of assessing vascular effects of a treatment by assigning individual humans or animals to different groups as described above can further include statistically analyzing data within each group before and after administration of the treatment.

In one embodiment, the present invention further provides for a method of screening for adverse effects of a treatment. The screening method includes the steps of applying the treatment to a number of individuals; monitoring the cerebrovascular blood flow of such individuals after applying the treatment; and identifying adverse effects to cerebrovascular blood flow in such individuals arising after applying the treatment.

The data regarding cerebrovascular health status obtained by the screening method of the present invention can include both the mean flow velocity value for intracranial blood vessels of the individuals and systolic acceleration value for intracranial blood vessels of the individuals. The intracranial vessels can be arteries. The arteries can be selected from the group consisting of is the common carotid, internal carotid, external carotid, middle cerebral, anterior cerebral, posterior cerebral, anterior communicating, posterior communicating, vertebral, basilar, and branches thereof. The data obtained may also include a pulsatility index.

The screening method permits quantitative data regarding the cerebrovascular blood flow of a number of individuals to be obtained. The quantitative data obtained may be collected by the use of ultrasound energy. Further, a Doppler probe can be used to collect the data regarding cerebrovascular health status.

The screening method treatment applied can include at least one treatment selected from the group consisting of administering a drug, conducting a procedure, and carrying out a therapy.

When the treatment selected is administration of a drug, the drug or substance can be a vasoactive drug, or a drug suspected of having vascular activity The screening method for adverse effects of a treatment on a vessel as described above may be applied both before and after administration of the treatment.

The screening method for adverse effects of a treatment on a vessel as described above may be applied on individuals suspected of having or actually having a vascular disease or a condition that affects vascular function.

The present invention comprises measurements of parameters of vascular function. Specifically, the present invention uses energy including, but not limited to, sound energy and any form of electromagnetic energy, to determine the rate of movement of cells through vessels. While not wanting to be bound by the following statement, it is believed that red blood cells account for the majority of cells detected with this technique. In a preferred embodiment, ultrasound energy is utilized.

According to the present invention, a sample volume of red blood cells is measured utilizing sound energy. Because not all blood cells in the sample volume are moving at the same speed, a range or spectrum of Doppler shifted frequencies are reflected back to the probe. Thus, the signal from the probe may be converted to digital form by an analog-to-digital converter, with the spectral content of the sampled Doppler signal then calculated by computer or digital signal processor using a fast Fourier transform method. This processing method produces a velocity profile of the blood flow, which varies over the period of a heartbeat. The process is repeated to produce a beat-to-beat flow pattern, or sonogram, on a video display. The instrument can be configured to analyze multiple separate frequency ranges within the spectrum of Doppler signals. Color coding may be used to show the intensity of the signal at different points on the spectral line. The intensity of the signal represents the proportion of blood cells flowing within that particular velocity range. The information displayed on the video screen can be used by a trained observer to determine blood flow characteristics at particular positions within the brain of the individual being tested, and can be used to detect anomalies in that blood flow such as the presence of a blockage or restriction, or the passage of an embolus through the artery, which introduces a transient distortion of the displayed information. The instrument can also include a processing option that provides a maximum frequency follower or envelope curve displayed on the video screen as the white outline of the flow spectrum.

In another preferred embodiment, coherent light in the form of lasers may be employed. In yet another embodiment, infrared or ultraviolet radiation may be employed.

In one preferred embodiment, the system and method of the present invention permits a determination of vascular health based on an analysis of two blood flow parameters, mean flow velocity and systolic acceleration.

Earlier studies have analyzed how blood velocity correlates with blood flow to the brain. Flow is a concept different from velocity; flow is the quantity per unit time delivered to a certain region of the brain. This is partially dependent on velocity. Accordingly, the earlier studies demonstrate a one-to-one relationship between flow and velocity. Therefore, mean flow velocity is a very good indicator of cerebral blood flow. Thus, conventionally, this theory has been relied upon to determine blood flow to the brain. There is a second calculated number called the pulsatility index, which is the resistance of blood flow downstream, which others have also measured. Still, there is a need to examine any combination of flow parameters to assess vascular health or auto-regulation.

In a more preferred embodiment of the present invention, transcranial Doppler is used to obtain the velocity measurements described above. Application of a selected form of energy to cells within the vessels permits a calculation of the flow rate of the cells within the vessels. By measuring specific parameters involved in the flow of cells through vessels, a data analysis may be performed.

One parameter of relevance to the present invention is mean blood flow velocity ($V_m$). The value of this parameter is given by the equation $$V_m = \frac{V_s - V_d}{3} + V_d$$

where
$V_s$=peak systolic velocity, and
$V_d$=end diastolic velocity.

A second parameter of relevance to the present invention is the pulsatility index ($P_i$). The value of this parameter is given by the equation $$P_i = \frac{V_s - V_d}{V_m}$$

where
$V_m$=mean blood flow velocity
$V_s$=peak systolic velocity, and
$V_d$=end diastolic velocity.

Another parameter of relevance to the present invention is systolic acceleration. This variable is determined by measuring the flow velocity at the end of diastole, measuring the flow velocity at peak systole, and then dividing the difference between these measures by the length of time between the end of diastole and the time of peak systolic velocity. This is an index of systolic acceleration. The value of this parameter is given by the equation—

$$A = \frac{V_s - V_d}{t_s - t_d}$$

where
$t_s$=time at $V_s$ and $t_d$=time at $V_d$
$V_s$=peak systolic velocity, and
$V_d$=end diastolic velocity.

In one preferred embodiment of the present invention, a characteristic signature for each vessel is defined by plotting the systolic acceleration against the mean flow velocity. With mean flow velocity plotted on the y-axis and systolic acceleration plotted on the x-axis, a vessel may be represented as a point on this graph.

The present invention reveals that vessels are in a state of normal auto-regulation when their vascular state values fall within the auto-regulating regions of the above described graph. A point on the graph represents a vascular state of a vessel. It has also been determined that when the value for an individual vessel falls within other regions of the graph outside the zone of auto-regulation, serious problems have either occurred or may be ongoing. Accordingly, the present invention permits not only a determination of the location of each individual vessel on such a graph, but also provides insight into the vascular health of a vessel in view of its deviation in distance and/or direction from what may be considered within the normal range of such vessels.

In another preferred embodiment of the present invention, another characteristic signature for each vessel is defined by plotting the systolic acceleration relative to the mean flow velocity and the pulsatility index. With mean flow velocity plotted on the y-axis, pulsatility index plotted on the z-axis, and systolic acceleration plotted on the x-axis, a vessel may be represented as a point in this 3-dimensional space.

The present invention further reveals that vessels are in a state of normal auto-regulation when their values fall in certain regions of this 3-dimensional space. The 3-dimensional plot provides a characteristic shape representing a cluster of points, wherein each point represents the centroid from an individual's specific vessel. It has further been determined that when the value for an individual vessel falls in other regions of the 3-dimensional space outside the zone of auto-regulation, serious problems have either occurred or may be ongoing. Accordingly, the present invention permits not only a determination of the location of each individual vessel on such a graph, but also provides insight into the vascular health of a vessel in view of its deviation, either in distance and/or direction, from what may be considered within the normal range of such vessels.

By means of the present invention, it has been determined that each cerebral vessel has a characteristic state and signature represented in a 3-dimensional graph. The characteristic state and signature for one vessel of an individual can be represented as a point in the vascular state diagram, and the characteristic states and signatures for a population of the same vessel type can be represented by a set of points described as a mathematical centroid. This value for the centroid is obtained through those analyses described above. The present invention reveals that individual vessels, especially individual cerebral vessels, display a clustering of points in 3-dimensional space that defines a shape.

It is to be understood that other variables may be employed in addition to systolic acceleration, mean flow velocity, and pulsatility index to provide additional information concerning specific vessels. When additional variables are employed, the data may then be plotted in a 4-dimensional or more dimensional space. Analysis of a specific centroid value for a vessel from an individual, in terms of its distance from the mean value for centroids for the same named vessel taken from other individuals, provides a basis for assessing the significance of differences between normal and abnormal vessels and enables predictions of abnormality. Accordingly, the present invention is not limited to 3-dimensional space. Further, individual vessels may be represented in n-dimensional space, wherein each dimension may be a relevant clinical parameter. For example, additional dimensions or variables may include, but are not limited to, age, clinical history or prior stroke, risk factors such as obesity, smoking, alcohol consumption, caffeine consumption, hypertension, closed head injury, history of migraine headaches, vasculitis, TIAs, prior intracranial trauma, increased intracranial pressure, history of drug abuse, steroid administration including estrogen and/or progesterone, lipid deposition, hyperlipidemia, parathyroid disease, abnormal electrolyte levels, adrenal cortical disease, atherosclerosis, arteriosclerosis, calcification, diabetes, renal disease, prior administration of therapeutic agents with vascular effects, prior administration of therapeutic agents with effects on the release or reuptake of norepinephrine at postganglionic sympathetic nerve endings, prior administration of therapeutic agents with effects on the release or reuptake of acetylcholine at postganglionic parasympathetic nerve endings, vascular denervation, shock, electrolyte levels, pH, $pO_2$, $pCO_2$, or any combination thereof.

The present invention permits analysis of all the vessels of an individual. These analytical methods provide an index of the vascular health of the individuals, especially the compliance of individual vessels. In a preferred embodiment, the present invention permits analysis of a vessel's ability to auto-regulate. Any such vessel may be analyzed provided it can be located with the device used to analyze blood flow. Both arteries and veins may be analyzed with the system and method of the present invention. Regarding arteries, both cerebral and non-cerebral vessels may be analyzed. For example, the common carotid, internal carotid artery, external carotid artery and other extracranial arteries may be evaluated. Further, analysis of the cerebral vessels of an individual can be performed with the system and method of the present invention, including the vessels contributing to the great arterial circle and their primary branches. The present invention further permits analysis of individual cerebral vessels from individuals in different groups, for example, groups within specific age ranges or at specific ages, groups considered healthy, groups which may fall into a clinically defined group, such as diabetics, groups of individuals who share common risk factors such as obesity, groups of individuals exposed to similar substances, such as nicotine, or pharmaceuticals, such as beta blockers.

The present invention includes a system having the capability for a variety of communication mechanisms such as access to the Internet that provides accurate prediction of the future occurrence of vascular disease, vascular disease diagnosis, determination of the severity of vascular disease, and/or vascular disease prognosis. The present invention provides one or more highly sophisticated computer-based databases trained to diagnose, prognose, determine the severity of and predict the future occurrence of vascular disease, and provide increased accuracy of diagnosis and prognosis.

The system of the present invention can operate by receiving patient vascular data from another location through a receiver or data receiving means, transmitting the data into a computer or through several computers containing vascular data for that specific vessel or numerous vessels in normal and/or diseased states, comparing the patient's vascular data to the database to produce one or more results, and transmitting the one or more results to another location. The other location may be a computer in a remote location, or other data receiving means.

In one embodiment of an automated decision support system for interpreting the values of various parameters of blood flow in one or more vessels in assessing the vascular health of an individual according to the present invention, at least three different modules are presented, each interactive with the other. These modules include a module for accessing data, a module for interfacing with a user, and module for processing patient data, or reasoning module.

The data access module provides access and storage methods for transcranial Doppler and clinical data inputted by a user, and for inferences from the reasoning engine. This data may be stored by any method known to those skilled in the art, including but not limited to storage on a network server, or storage in a file on a personal computer. The data access module is able to respond to a variety of commands, including but not limited to a command to initialize the module, one to retrieve patient data, a command to save patient data and/or graphs, a command to delete patient data and/or graphs, a command to retrieve a list of patients, and a command to query the database.

The user interface module performs various functions, including but not limited to processing user input to be sent to the data access module, running commands for the reasoning module, querying about patient data for the data access module, and querying about inference results from the reasoning module. The user interface module may further be designed to display patient data for at least one patient received from the data access module and concept instances received from the reasoning module. The user interface module can also be designed to display clinical and demographic data for a patient, raw transcranial Doppler velocimetry data, and an analysis of a patient's hemodynamic state. The analysis of the patient's hemodynamic state includes, but is not limited to the condition of each artery, any global conditions detected, and an assessment of the patient's risk for stroke. The user interface preferably provides a user the ability to drill down from a patient's assessment of the risk for stroke in order to determine how conclusions were reached.

The reasoning interface module performs various functions, including but not limited to accepting commands to process patient data for inferred concepts, searching for instances of particular concepts or evidence of a given concept instance in a concept graph, and saving the concept graph or loading an old concept graph. The reasoning interface can be further broken down into at least two other modules—an analysis module for performing analysis of the data inputted, including but not limited to any user input, saved concepts and/or data, clinical data, and transcranial Doppler data; and an interface module for hiding the details of the interaction of the analysis module with the other modules. The interface module allows other modules to access data and concept graphs residing in the analysis module without exposure to the analysis interface. Preferably, those files created by the reasoning module are stored by the data access module.

According to the present invention, patient data includes all data derived from transcranial Doppler readings and all clinical data. Preferably, patient data is accessed and stored as a single block of data for each patient, referenced by a unique patient ID.

In one embodiment of the present invention, transcranial Doppler data and clinical data is inputted by a user at the user interface. Once the input has been completed, the user can either save the data to a file for later access, or can immediately analyze the data before saving it. In either instance, patient data is retrieved by the reasoning module from the data access module. Both modules retrieve patient data based on patient ID. Preferably, a user is able to retrieve a list of all patients saved in a file in order to be able to select a particular patient's data to view, edit, or analyze. Preferably, although not necessary, the set of parameters sent to the data access module includes a user ID.

The analysis module is able to provide one or more classes of service. For example, the module includes methods for commanding the analysis module, including commands for initializing, starting, running and stopping the module. Another class of service provided by the module may include methods for setting and/or retrieving concept attribute values.

As defined by the above described modules, the present invention is able to provide the sequences for an automated decision support system for interpreting the values of various parameters of blood flow in one or more vessels in assessing the vascular health of an individual. These sequences include but are not limited to saving patient data, analyzing patient data, loading an analysis to an analysis page, and retrieving evidence from a concept graph.

By means of the above described modules, the present invention is able to provide the software design for an automated decision support system for interpreting the values of various parameters of blood flow in one or more vessels in assessing the vascular health of an individual.

With the use of the above described modules, the present invention is able to provide the use cases for an operational prototype for an automated decision support system for interpreting the values of various parameters of blood flow in one or more vessels in assessing the vascular health of an individual. These use cases, or user interface commands, include but are not limited to entering new patient data, loading existing patient data, viewing clinical data, viewing transcranial Doppler velocimetry, analyzing patient data, viewing analyses, and gathering the evidence behind an analysis.

In a preferred embodiment of the present invention, there is provided a process by which the vascular health assessment can be carried out remotely, allowing for interrogation of a patient's vascular health at one location, while processing the patient's data information obtained by ultrasound measurements of the cerebral vascular health state from various flow parameters is done at another location. This process is preferably managed in a stepwise fashion using a decision matrix developed to obtain the appropriate data set given the patient's particular situation at the time. Therefore, the process can be remotely managed and the data can be remotely processed.

For example, a technician or physician would assist a patient by applying to the patient's head an appropriate device that would obtain the necessary transcranial Doppler data, or alternatively, a probe would be placed at appropriate windows on the skull to obtain the Doppler data. The vascular health data would then be collected and transmitted to another device that would perform the vascular health assessment. The data would then be processed and an interpretation generated, as well as potential recommendations for additional measurements. The assessment process itself could be done one test at a time in batch mode, or it could be done continuously on an online system. The interpretation and potential recommendations can then be relayed to another location, this location can be any of several choices, including the location of the patient, the location of the health care provider, or the location where the diagnosis will be communicated.

In executing the analysis, the analyst, e.g., a computer or assessor, would perform the analysis and, preferably, do a comparison to a reference population. The reference population could be the group of patients evaluated that day or it could be the population that is appropriate in some other respect. In any case, it is important to consider the reference population and to have a current data set on the reference population because the predictive value would be affected by the underlying prevalence of individuals in that particular reference group.

It will be appreciated that the transmission of the vascular health information from the measurement device to the vascular health assessor and the transmission of the interpretation of vascular health to a communication location can be accomplished through a variety of communication links, including, modem, cable modem, DSL, T1, and wireless transmission. The transmissions could be batch or continuous.

It will be appreciated that in a client-server informatics embodiment, some assessment functions might reside on the client side while others would reside on the server side, the ratio of what is placed on each being a function of optimal bandwidth, computer speed and memory. Other considerations include remote transmission of the data, either in stepwise manner or in a batch mode, through a computational device attached to the ultrasound probe.

The present invention further includes a system, combined with access to the Internet and other communication mechanisms, that provides substantially accurate prediction of the future occurrence of vascular disease, vascular disease diagnosis, determination of the severity of vascular disease, and/or vascular disease prognosis. The present invention further provides one or more highly sophisticated computer-based databases trained to interrogate, diagnose, prognose, determine the severity of and predict the future occurrence of vascular disease, and provide increased accuracy of diagnosis and prognosis. The present invention also provides a sensitive tool to assess subtle differences in flow characteristics following exposure to substances such as drugs in a clinical environment.

The present invention may also be combined with a file system, such as an electronic file system, so that the individual patient's vascular data file, the results from the analysis of vascular flow characteristics, may be stored in the patient file. In this manner, the health care provider or patient may have rapid access to information in the patient file. Changes in vascular health since previous visits to the health care provider may be determined quickly, thereby indicating whether vascular disease progression has changed or, if recommended, interventional strategies or therapeutics are effective. The present invention also provides physicians with the ability to rapidly advise patients concerning recommended additional diagnostic testing and available treatment options following receipt of information from the computer-based database about the prediction of the future occurrence of vascular disease, disease diagnosis, determination of the severity of vascular disease, and/or vascular disease prognosis.

It is therefore an object of the present invention to provide a new method for assessing vascular health.

It is further an object of the present invention to provide a method for routine evaluation of cerebral vascular health.

Yet another object of the present invention is to evaluate the vascular health of individuals at risk for disease.

Still another object of the present invention is to provide a method for monitoring patients who have experienced a vascular problem, such as stroke.

Another object of the present invention is to provide a method for evaluating the response of vessels to treatment(s), including conducting procedures, carrying out therapies, and administering substances.

A specific object of the present invention is to evaluate the vascular response to substances in individuals at risk of cerebral vascular pathology.

Yet another object of the present invention is to evaluate the vascular response to treatment(s), including conducting procedures, carrying out therapies, and administering drugs which may be used in a therapeutic manner.

Another object of the present invention is to provide ongoing evaluation of the vascular health of patients following stroke, closed head injury, contra coup lesions, blunt force trauma, transient ischemic attacks, migraine, intracranial bleeding, arteritis, hydrocephalus, syncope, sympathectomy, postural hypotension, carotid sinus irritability, hypovolemia, reduced cardiac output, cardiac arrhythmias, anxiety attacks, hysterical fainting, hypoxia, sleep apnea, increased intracranial pressure, anemia, altered blood gas levels, hypoglycemia, partial or complete carotid occlusion, atherosclerotic thrombosis, embolic infarction, carotid endarterectomy, oral contraceptives, hormone replacement therapy, drug therapy, treatment with blood thinners including coumadin, warfarin, and antiplatelet drugs, treatment with excitatory amino acid antagonists, brain edema, arterial amyloidosis, aneurysm, ruptured aneurysm, arteriovenous malformations, or any other conditions which may affect cerebral vessels. In addition, changes in vascular flow following aneurysm rupture can also be monitored.

It is another object of the present invention to evaluate drugs or other substances suspected to have vascular activity.

Yet another object of the present invention is to evaluate drugs with suspected vascular activity in individuals known to be at risk of vascular disease.

Another object of the present invention is to evaluate substances, such as drugs, suspected of having vascular activity in individuals following stroke.

Yet other object of the present invention is to provide a non-invasive method to evaluate substances, such as drugs, suspected of have vascular activity in individuals with no apparent vascular problems.

Another object of the present invention is to provide a non-invasive method to evaluate different dosages of substances, such as drugs, suspected of have vascular activity in individuals.

Still another object of the present invention is to provide a non-invasive method to evaluate different combinations of substances, such as drugs, suspected of have vascular activity in individuals.

Yet another object of the present invention is to provide a non-invasive method to evaluate different combinations of selected dosages of substances, such as drugs, suspected of have vascular activity in individuals.

A further object of the present invention is to evaluate the vascular health of specific vessels or vascular beds following vascular insult in another region of the cerebral vasculature. In this manner, the capacity of other vessels to properly autoregulate and distribute collateral blood flow may be assessed.

An advantage of the present invention is that it is not invasive.

A further advantage of the present invention is that it is rapid and inexpensive to perform.

Another advantage of the present invention is that the characteristics of each cerebral vessel may be established as a baseline in order to monitor the vascular health of the individual over time, especially during routine physical examination, following a vascular insult or injury, or exposure to drugs.

Yet another advantage of the present invention is that analysis of individual vessels and their deviation from a normal value for a corresponding vessel in another individual may indicate specific medical conditions. Treatment of those medical conditions may then be evaluated with the present invention to determine whether the treatment was effective on the specific vessel being evaluated.

Accordingly, it is an object of the present invention to provide a system for efficient delivery of information concerning the vascular health of an individual.

Yet another object of the present invention is to provide a system which health care providers can utilize to provide more precise and accurate prediction of the future occurrence of vascular disease, diagnosis of vascular disease, determination of the severity of vascular disease and prognosis of vascular disease.

An object of the present invention is to provide a system which health care providers can utilize to provide more precise and accurate prediction, diagnosis and prognosis of vascular diseases, and associated treatment options, such diseases including, but not limited to, cerebrovascular disease.

It is further an object of the present invention to provide a computer-based database that may receive vascular flow data from an input device, interpret the vascular flow data in view of existing data for the same vessel or vessels in normal or disease states, produce a value(s) that provides useful information concerning vascular health and then optionally transmit the information to another location.

It is yet another object of the present invention to provide a system that delivers to the health care provider a complete patient report within a short time interval.

It is another object of the present invention to provide point-of-care analytical capabilities linked through communication means to local or remote computers containing a computer-based database that may receive vascular flow data from an input device, interpret the vascular flow data in view of existing data for the same vessel or vessels in normal or disease states, produce a value that provides useful information concerning vascular health, and then optionally transmit the information to another location. Such output values may be transmitted to a variety of locations including the point-of-care in the health care provider's office that transmitted results from the point-of-care flow measuring device. The present invention provides accurate, efficient and complete information to health care providers using in order to enhance affordable and quality health care delivery to patients.

These and other objects, features and advantages of the present invention will become apparent after a review of the following detailed description of the disclosed embodiments.

BRIEF DESCRIPTION OF THE FIGURES

FIG. 26 is an illustration of a transcranial Doppler data window of a preferred embodiment of the invention;

DETAILED DESCRIPTION OF THE INVENTION

Figure 1:
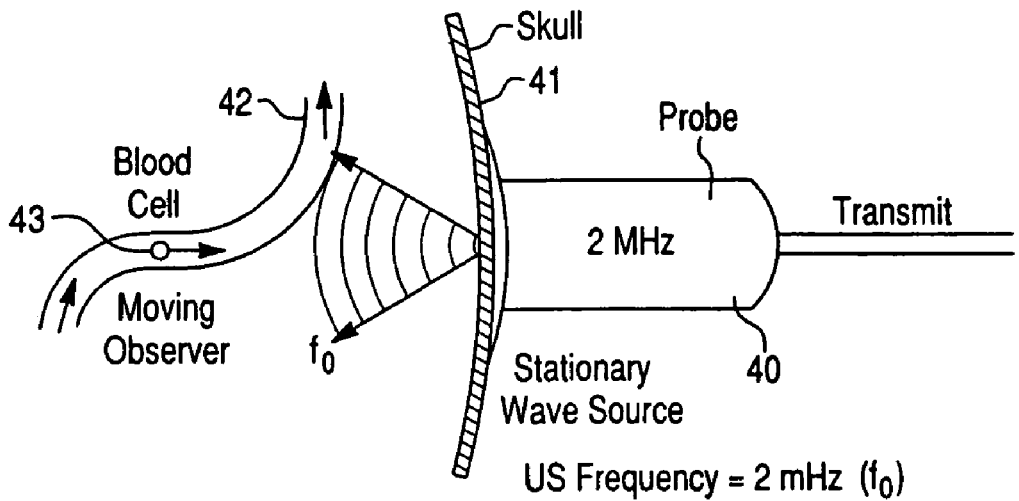
FIGS. 1 to 4 are illustrative views showing the manner in which ultrasonic pulses are applied to the head of an individual to obtain information on the velocity of blood flowing in an intracranial blood vessel.
Figure 2:
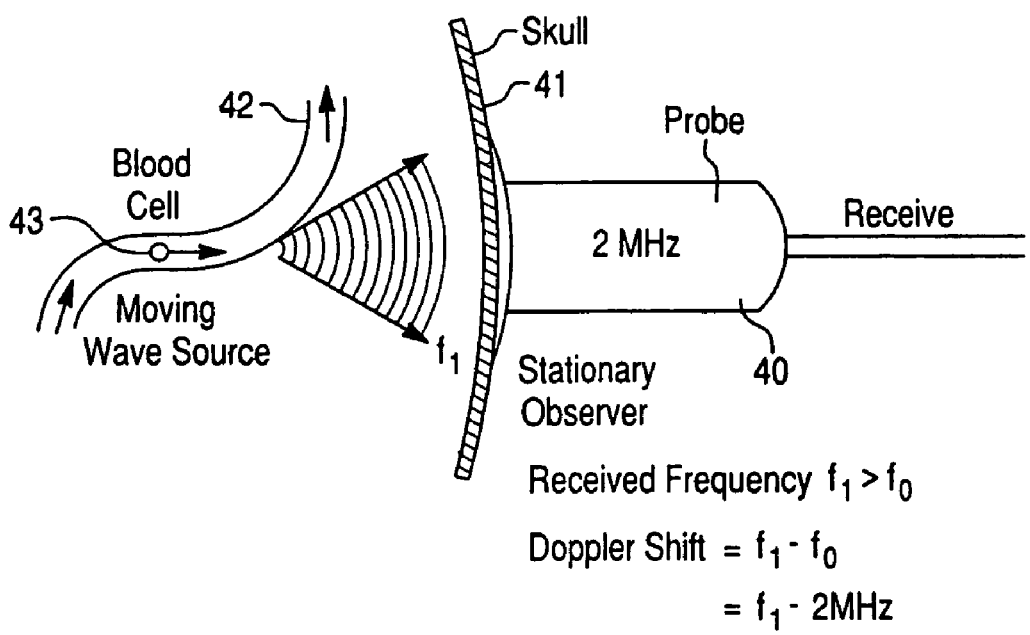
Figure 3:
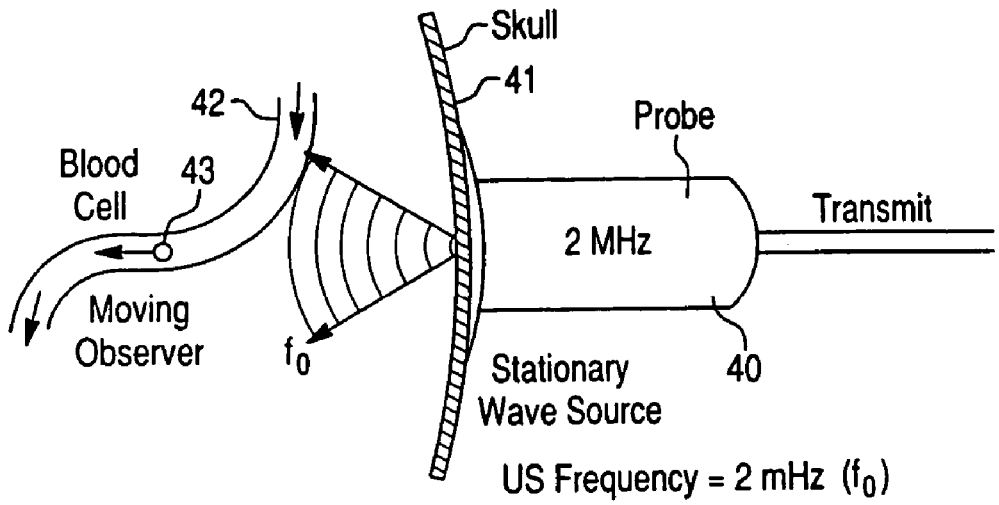
Figure 4:
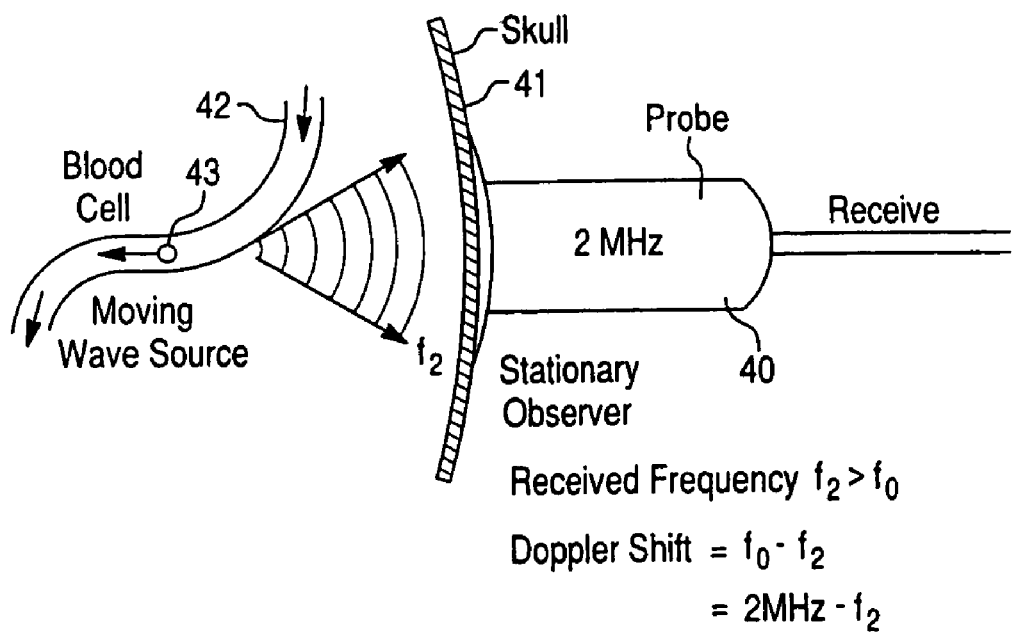

This application expressly incorporates herein by reference in their entirety co-pending and commonly assigned U.S. patent applications Ser. Nos. 09/966,368, 09/966,360, and 09/966,359, all filed on Oct. 1, 2001.

The present invention provides a novel system and method for evaluating vascular health. This invention may be used to evaluate individuals for risk of cerebral vascular disease. The invention may also be used for evaluating vascular health in individuals following a vascular insult or stroke. The present invention may also be used for assessing the effects of individual substances and combinations of substances on cerebral vessels.

As noted above, the present invention comprises measurements of parameters of vascular function. Specifically, the present invention uses energy including, but not limited to, sound energy or any form of electromagnetic energy, to determine the rate of movement of cells through vessels. In a preferred embodiment, ultrasound energy is utilized.

Description of Flow Data Acquisition and Analysis

According to the system and method of the present invention, a noninvasive instrument is utilized to obtain measurements of blood velocity in intracranial arteries and veins using Doppler principles. Since body movements such as vessel wall contractions are detected as "noise" in the Doppler signal scattering ultrasound, a high pass filter is used to reduce these low frequency, high amplitude signals. The high pass filter typically can be adjusted to have a passband above a cutoff frequency selectable between 0 and, e.g., 488 Hz.

Because not all blood cells in the sample volume are moving at the same speed, a range or spectrum of Doppler-shifted frequencies are reflected back to the probe. Thus, the signal from the probe may be converted to digital form by an analog-to-digital converter, and the spectral content of the sampled Doppler signal calculated by a computer or digital signal processor using a fast Fourier transform method. This processing method produces a velocity profile of the blood flow, which varies over the period of a heartbeat. The process is repeated to produce a beat-to-beat flow pattern, or sonogram, on a video display. The instrument can be configured to analyze multiple separate frequency ranges within the spectrum of Doppler signals. Color coding may be used to show the intensity of the signal at different points on the spectral line. The intensity of the signal will represent the proportion of blood cells flowing within that particular velocity range. The information displayed on the video screen can be used by a trained observer to determine blood flow characteristics at particular positions within the brain of the individual being tested, and can detect anomalies in such blood flow, for example, the possible presence of a blockage or restriction, or the passage of an embolus through the artery which introduces a transient distortion of the displayed information. The instrument can also include a processing option which provides a maximum frequency follower or envelope curve which is displayed on the video screen as the white outline of the flow spectrum.

Figure 5A:
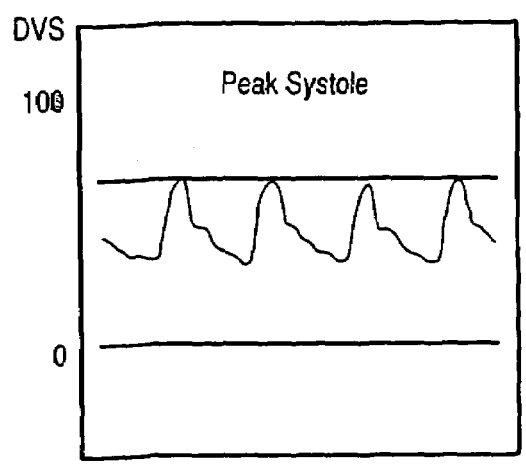
FIGS. 5a to 5d provide schematic representations of transcranial Doppler ultrasound analyses in which velocity is indicated on the y-axis and time is provided on the x-axis.

FIGS. 5a to 5d illustrate Doppler waveform definitions provided by a system according to the present invention. FIG. 5a is a graph, providing the results of a transcranial Doppler ultrasound analysis in which velocity is indicated on the y-axis and time is provided on the x-axis. The peak systole velocity is indicated in the Figure.

Figure 5B:
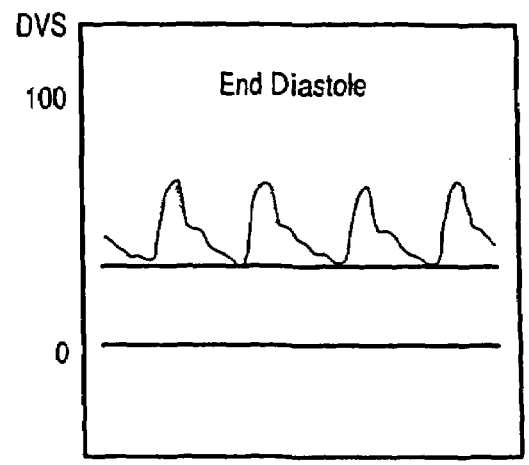

FIG. 5b is a graph providing the results of a transcranial Doppler ultrasound analysis in which velocity is indicated on the y-axis and time is provided on the x-axis. The end diastole velocity is indicated in the Figure.

Figure 5C:
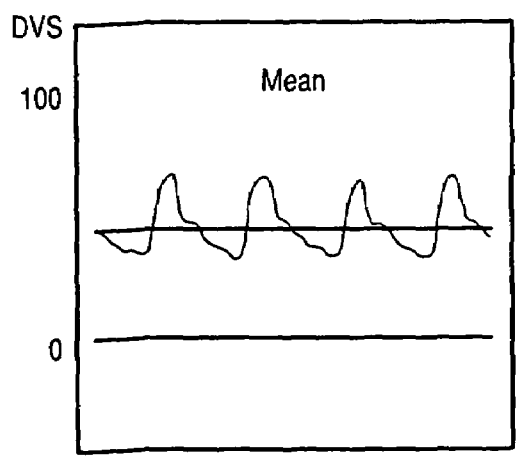

FIG. 5c is a graph providing the results of a transcranial Doppler ultrasound analysis in which velocity is indicated on the y-axis and time is provided on the x-axis. The mean flow velocity is indicated in the Figure.

Figure 5D:
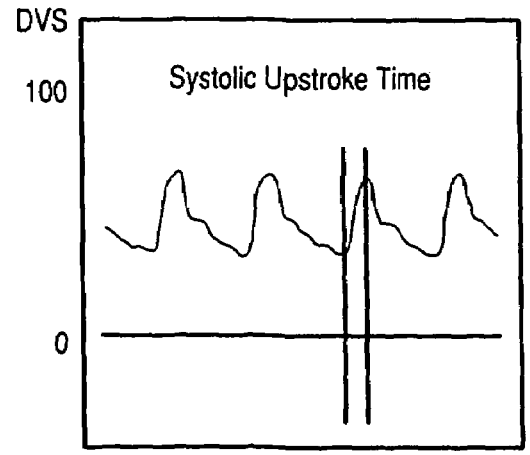

FIG. 5d is a graph providing the results of a transcranial Doppler ultrasound analysis in which velocity is indicated on the y-axis and time is provided on the x-axis. The systolic upstroke time or acceleration is indicated in the Figure.

The present invention provides a plot on a two-dimensional graph of the systolic acceleration and mean flow velocity. Referring back to the auto-regulation model, one now finds that the auto-regulation curve more accurately describes the vascular health of a system. Addition of a third dimension, the pulsatility index, provides a three-dimensional plot, that gives a much more accurate look at how blood is flowing in that particular subsection of the vessel. Thus, the present invention combines different blood flow parameters to give a nomogram or a graphical representation of how blood is flowing within the brain itself.

The present invention permits the interrogation of cerebral vessels to determine the state of vascular health or disease by examining the flow parameters for a vessel and comparing then with a normal value. This also permits a clinical trial to be run since an entire population can be interrogated with this relatively quick and noninvasive technique, thereby obtaining readings not only for each individual patient, but also for the population. In addition, one can monitor the flow dynamics of the group as a whole over time and determine if either the non-treatment group becomes more diseased or if the treatment group stabilizes, improves, or has a lower rate of disease, all determined by clinical measurements. Thus, the present invention provides a very sensitive blood flow interrogation tool for the brain to determine whether a drug is going to be safe or effective for use in patients.

Using an ultrasound probe, one can determine the velocity of blood. The relationship of the velocity of blood at two separate points within the points will provide the flow parameters of the present invention. Analyzing the relationship of the three parameters in each individual segment in relationship to a normal population can determine the state of disease of that particular segment of vessel. Further, assessing all the segments of vessels in the brain as a whole, one can determine the interconnections and the states of abnormal flow into whole regions of the brain. The more regions of the brain at risk, the higher the stroke risk for the patient. Thus, the present invention permits one to quantitate stroke risk in patients.

Figure 6:
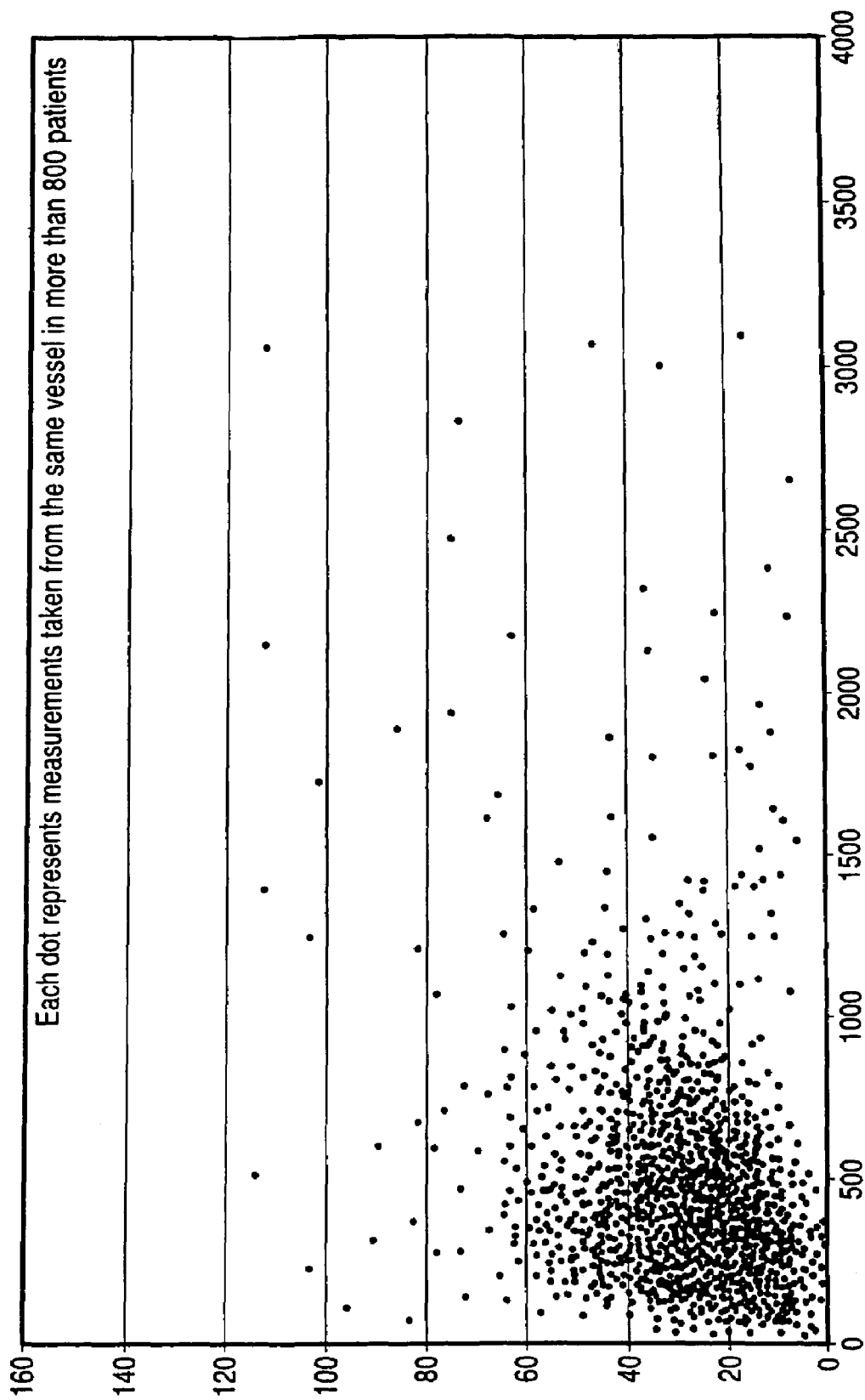
FIG. 6 is a schematic representation of a 2-dimensional nomogram in which mean flow velocity is indicated on the y-axis and systolic acceleration is provided on the x-axis.
Figure 7:
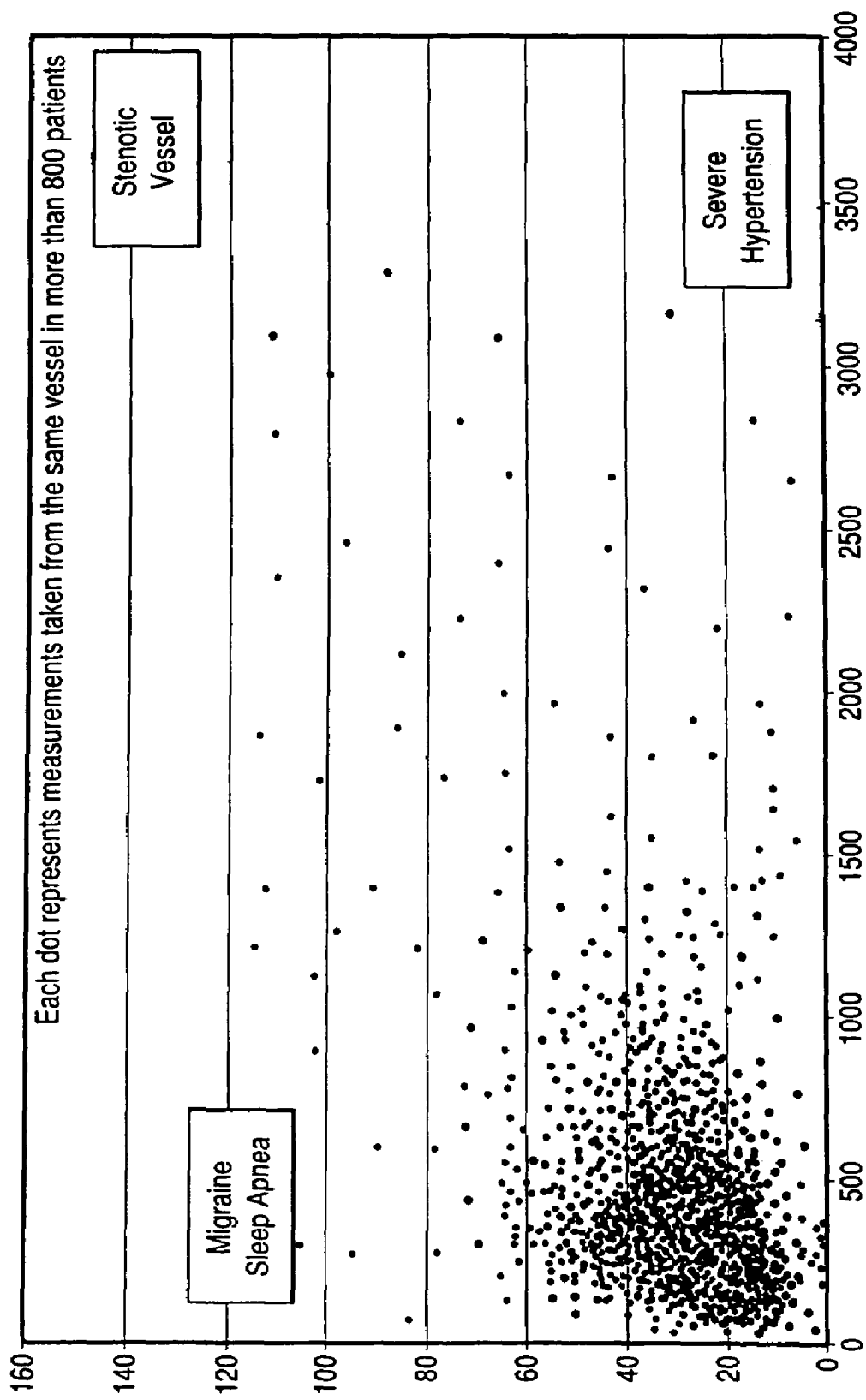
FIG. 7 shows the nomogram of FIG. 6, as well as areas of the nomogram which indicate deviations from normal, auto-regulatory conditions.

According to the present invention, values for various transcranial Doppler sonography measurements for a number of patients are collected into a database of the present invention. The database may further provide ranges of transcranial Doppler sonography measurements for various cerebral arteries. FIG. 6 provides a nomogram of the values for mean flow velocity on the y-axis and systolic acceleration on the x-axis for transcranial Doppler ultrasound analyses of the ophthalmic artery in a number of individuals. It will be appreciated that the majority of the data points are grouped in the lower left-hand side of the nomogram. These represent the values corresponding to vascular health. The aberrant points found in the upper left-hand portion of the nomogram correspond to a state of vascular disorder, specifically, vasodilation. In addition, the aberrant points found in the lower right-hand portion of the nomogram also correspond to a state of vascular disorder; however, here these points correspond to stenosis. These observations are provided in FIG. 7.

Figure 8:
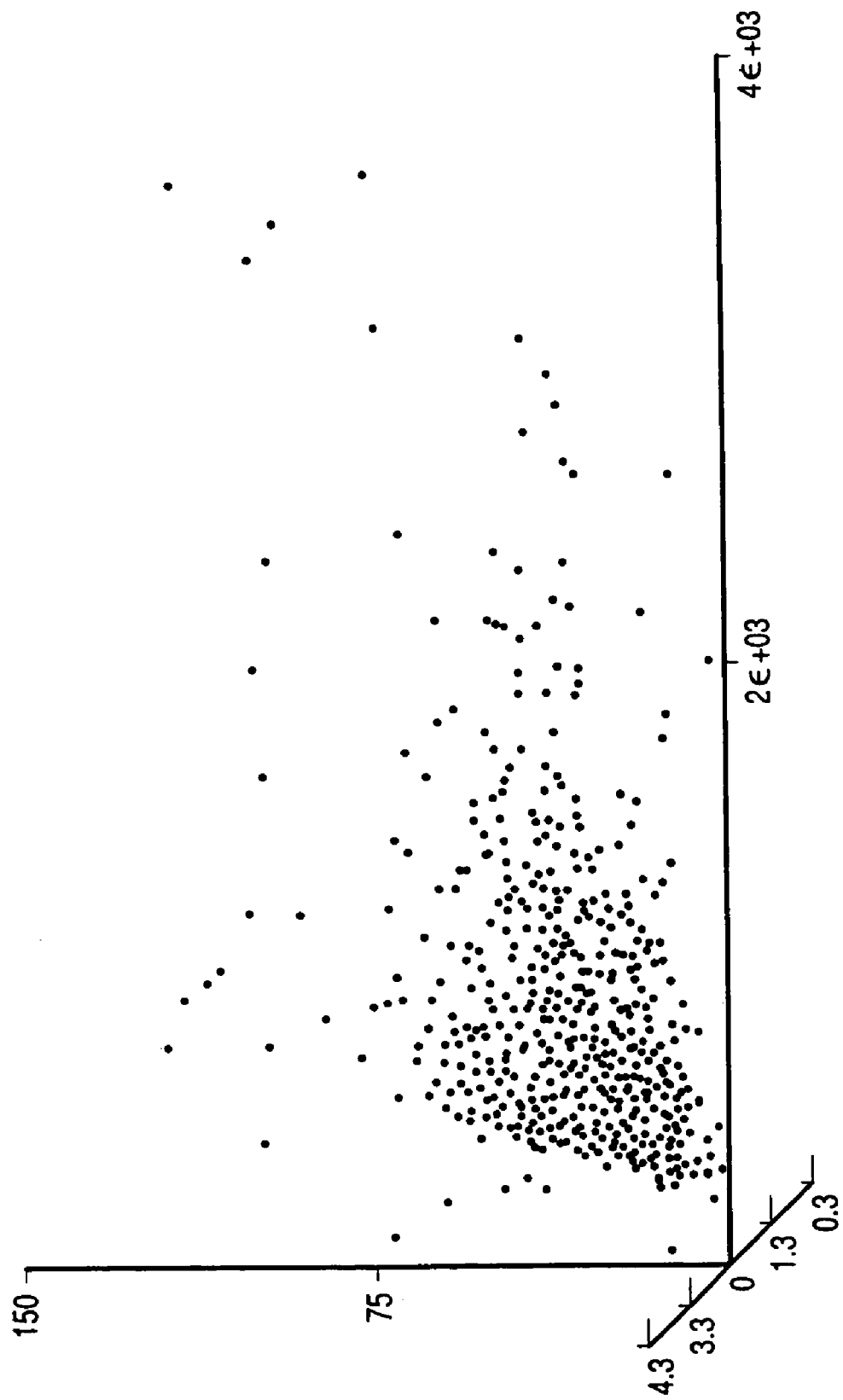
FIG. 8 shows a schematic representation of a 3-dimensional nomogram.

In another preferred embodiment, the system and method of the present invention permits a determination of vascular health based on an analysis of three blood flow parameters, mean flow velocity, systolic acceleration, and pulsatility index. For example, FIG. 8 provides a nomogram of the values for mean flow velocity on the y-axis, systolic acceleration on the x-axis, and pulsatility index on the z-axis for transcranial Doppler ultrasound analyses of a cerebral artery in a number of individuals. It will be appreciated that the majority of the data points are grouped in a centroid located in the first octant (x>0, y>0, z>0) close to the origin of the nomogram. If plotted as the logarithm of the value, these exhibit a normal distribution. The normal range of the log of these values represent the values corresponding to the vascular health of the reference population. Thus, the present invention permits the construction of any and all reference populations based on the data collected from the reference population. The data set is the ideal reference set because the reference population can be defined in any manner, e.g., those patients who are exhibiting a certain set of symptoms or desired characteristics.

The aberrant points found distal to the origin and having a large mean flow velocity (y value) in the nomogram correspond to a state of vascular disorder, specifically, vasodilation. In addition, the aberrant points found distal to the origin and having a large systolic acceleration (x value) in the nomogram also correspond to a state of vascular disorder; however, here these points correspond to stenosis.

The measurements, gathered on a substantial number of individuals to date, demonstrate that the observed values for a normal population show statistically normal distributions of values for the three parameters, mean blood flow, systolic acceleration, and pulsatility index. Scrutinized by means of standard multivariate statistical methods, such as tests of significance, multivariate distances, and cluster analysis, the observed values for all three parameters all show a statistically normal distribution.

An aspect of a preferred embodiment of the present invention is the collection of data by means of transcranial Doppler sonography. As discussed previously, instrumentation for conducting transcranial Doppler sonography is commonly a 2 MHz pulsed Doppler and a spectrum analyzer, in which the examiner interrogates the intracranial vessels without the aid of an image. Such a technique is referred to as freehand, blind, or non-imaging transcranial Doppler sonography. Recently, duplex ultrasound systems incorporating B-mode imaging and color and power Doppler have been employed to perform transcranial Doppler studies. However, despite advances in duplex ultrasound technology, freehand transcranial Doppler sonography is commonly performed because the technique can be equally accurate and the instrumentation less expensive and more portable when compared to the duplex ultrasound.

Although freehand transcranial Doppler sonography can be characterized as operator dependent, the technique is objective and reproducible. The operator, in conducting transcranial Doppler sonography, considers the relevant anatomy, natural cranial windows, and recognized examination techniques. Specifically, an understanding of the extracranial arterial circulation contributing to the intracranial flow, the intracranial arterial circulation, carotid arteries, vertebral arteries, basilar artery, and their common anatomical variations is a prerequisite.

Additionally, in conducting the examination the examiner must also identify the vessel. Such identification is often premised upon the acoustical window being utilized, the depth of the volume sample, the direction of the blood flow relative to the transducer, the relative velocity, and spatial relationships.

The examiner must also recognize that there are three acoustical windows or regions over the cranium where the bone is either thin enough or through which there are natural openings to allow sufficient ultrasound energy to be passed into and back out of the skull to permit performance of a transcranial Doppler examination, i.e., the signal-to-noise ratio is adequate at the "window." However, enhanced phase array detectors may provide sufficiently improved signal-to-noise ratio that a "window" may not be necessary. The three acoustical windows are the transtemporal window located superior to the zygomatic arch over the temporal bone; the transorbital window where the transducer is oriented directly over the closed eyelid in a direct anteroposterior direction with a slight angulation toward midline; and the transforamenal window located midline over the back of the neck approximately 1 inch below the palpable base of the skull. It is to be understood that other windows may be used for other approaches using sound or other electromotive forces for detection of cell movement within vessels. It will be recognized that many texts provide sufficient instruction to examiners so as to enable them to perform optimal transcranial Doppler sonography. One such text is L. Nonoshita-Karr and K. A. Fujioka, "Transcranial Doppler Sonography Freehand Examination Techniques," J. Vasc. Tech., 24, 9 (2000), which is incorporated herein by reference.

In another preferred embodiment of the present invention, ultrasound beam alignment is controlled rapidly and automatically in two dimensions. Devices that scan azimuth angle rapidly while varying elevation angle in small increments have been used for 3-dimensional image construction, but lack speed in controlling elevation. In the analogous area of laser scanning, it is common to steer a light beam in two dimensions using a pair of orthogonally-rotating mirrors driven by galvanometer movements. The double mirror approach does not work as well with ultrasound, however. The size and cumbersomeness of a pair of galvanometer driven mirrors is a disadvantage in medical applications, especially for limited space uses such as transesophageal and transrectal probes. Another design constraint is that the wavelengths of diagnostic ultrasound waves are much larger than optical wavelengths, of necessity, since attenuation of ultrasound waves rises steeply with decreasing wavelength. As a rule of thumb, ultrasound wavelength cannot be much less than 1% of the maximum depth to be imaged, with an even larger wavelength required for imaging through tissues with high attenuation. With relatively large wavelengths, diffraction effects make it impossible to produce very thin collimated beams that can be steered by small mirrors, as with lasers.

For sharp focusing of ultrasound, a relatively large aperture is needed to avoid angular dispersion by diffraction. A well focused near field ultrasound beam has the shape of a converging cone connecting to a diverging cone through a short focal neck, representing a small depth of near-optimum focus in the target area. Resolution approaching a practical minimum spot diameter of a little under two wavelengths at the focus demands an included cone angle on the order of 60°. If the originating end of the columnar beam is made smaller while maintaining a fixed focus depth, then diffraction causes the focal neck to become thicker, sacrificing resolution at optimum depth for an increased depth range of relatively good focus. To achieve fine focus with a double mirror apparatus, the mirrors must be comparatively large, increasing the difficulty of attaining fast angular response.

Typical electromechanical ultrasound image scanners employ multiple transducers on a rotating head, or an ultrasound mirror rotationally vibrating at an angular resonance—approaches that achieve desired azimuth scanning by sacrificing the possibility of precise angular servo-control in a non-scanning mode.

In radar, phased arrays permit rapid scanning and abrupt alignment changes in two dimensions from a fixed transmit/receive surface. A comparable approach is applicable to medical ultrasound. One dimensional ultrasound phased arrays are finding increasing use, and limited control of alignment in a second dimension is beginning to appear. In one preferred embodiment, a stepper motor is used to rotate the scanning plane of a one-dimensional phased array through small incremental steps in order to construct a 3-dimensional digital image. This approach requires that the target and the ultrasound scanner be mechanically stabilized so that frames of a slow scan are in precise registration. A phased array with dual sets of electrodes that permit beam steering in either of two selected scanning planes can be used. For example, a system that employs a one dimensional ultrasound array can achieve controllable alignment and focus depth in a plane, for use in range-gated pulsed Doppler to characterize the flow velocity profile over the cross-section of an artery. The device is also useful to quantify angular relationships, through comparing Doppler velocities at different axial locations along an artery, so that the relationship between Doppler frequency shift and flow velocity can be determined accurately.

In many emerging ultrasound applications, visual image scanning takes on a supporting role of identifying structures and defining their positions, in preparation for analytic measurements in a small region, which is concerned with measuring flow velocity profiles over the dimensions of an artery and over time, to characterize volumetric flow and to detect the flow disturbances caused by stenotic lesions. Using fixed alignment defocused beams or beams electromechanically aligned with respect to two axes, ultrasound can be used to track the time-varying positions of organ surfaces generating specular reflections, for the purposes of vibration tracking and diameter pulsation tracking, in a system to determine blood pressure, intraocular pressure and mechanical tissue properties. One preferred embodiment would consist a non-focusing 2-axis ultrasound aiming device, consisting of an ultrasound transducer disk stacked on a short magnet cylinder and the transducer-magnet pair mounted in a 2-axis gimbal bearing, consisting of pins and engaging bearing cups on the ring and the magnet, with flexible wires connecting the gimbaled part to fixed housing. Surrounding the gimbal is a torroidal ferromagnetic core in four sections, with four windings on the four 90° quadrants of the core. Opposite windings are interconnected, giving two electrical circuits that generate two orthogonal magnetic fields crossing the gimbaled transducer-magnet pair. The gimbaled part tilts in response to the two applied fields, aiming the ultrasound beam.

In this aiming device, the axially-poled center magnet is inherently unstable in its center alignment, being attracted to point across the torroid. To stabilize alignment, the torsional restoration of the connecting wires must overcome the magnetic instability. Alignment direction is determined open-loop by the balance of mechanical and magnetic forces, without direct sensing for servo-control. In an uncompensated open-loop control situation, if the net alignment restoration is weak, then settling is slow, and if restoration is made stronger, then the steady power needed to maintain off-center alignment becomes excessive. A compensated open-loop controller whose action takes into account the known dynamic properties of a particular design, i.e., inertia, angular spring coefficient, damping, and electromagnetic coupling strength, can speed response. The term "pole-zero compensation" is often applied to this kind of a controller, since LaPlace pole-zero analysis is commonly used to design the controller transfer function. To speed responses, the controller transfer function cancels electromechanical low frequency zeroes with poles and low frequency poles with zeroes, generally replacing the poles removed with new poles as far to the left of the origin as is practical within bandwidth constraints.

Something much needed and unavailable in existing designs is fast mechanical alignment capability together with alignment sensing and error feedback for rapid, fast settling changes in alignment. In areas of alignment tracking and analysis of echo features and their movements or velocities, particularly for extended monitoring in unanesthetized subjects, there is need for a combined ability to scan rapidly for image presentation and to fine-tune 2-dimensional beam alignment under continuous software control, to maintain alignment dynamically on a tissue structure subject to extended monitoring.

In the area of combined scanning and fixed beam alignment monitoring, a phased array device that switches readily between B-Mode image scanning and Doppler tracking at a specified alignment within the image plane can be employed. A device like this, with phased array speed, can alternate between scanning sweeps and brief periods of Doppler data gathering at a fixed alignment in a time-multiplexed mode, achieving relative continuity of both image and Doppler data. Electronic alignment control is restricted to a single axis, while manual control is needed for the second axis. One can also employ a dual beam ultrasound device, using one beam for tracking data from a fixed target and the other beam for ongoing scanning to aid the operator in maintaining alignment on the desired target. Again, the other axis of alignment is controlled manually.

For many applications it is advantageous to achieve a device small enough so that it can be affixed directly to the subject's body and ride body motions, rather than obtaining measurements in a clinical setting. The advantages of the present invention in fulfilling these and other needs will be seen in the following specification and claims.

Description of Data Telemetry

The present invention provides an integrated system which combines several unique technologies to assist physicians in the control, management and delivery of improved, efficient and timely medical care for patients. Key components of this integrated system include, but are not limited to, (1) a processor which may include, but is not limited to, a desktop personal computer, a laptop computer, or a multi-user server system; (2) an output device for displaying information from the processor, such as monitors, printers, liquid crystal displays, and other output devices known to one skilled in the art; and optionally including (3) analyzers for assessing a patient's clinical profile. Such analyzers may be used for analyzing flow characteristics of a vessel or number of vessels.

All patient data may be placed in a form, such as a digitized form or other computer readable and communication acceptable form, and transmitted to another location. In one embodiment, the computer-based database may be located in the office of the health care provider, perhaps in the computer in a physician's office. In another embodiment, the computer-based database may be located in a centralized hospital facility, in a emergency room/service, in a clinical chemistry laboratory, or in a facility dedicated solely to housing and maintaining the computer-based database. In yet another embodiment, the computer-based database may be located in a home computer. In a further embodiment, the computer-based database may be portable for uses such as on a battlefield, in rural areas and at events.

Another component in the system of the present invention includes a transmission device such as a modem or other communication device known to one of skill in the art. Such devices include, but are not limited to satellites, radios, telephones, cables, infrared devices, and any other mechanism known to one of skill in the art for transmitting information. The transmission device modem transmits information to the central computer-based database. In a preferred embodiment, modems are used for computer access to the Internet. Such communication means may be essential for transmission of patient information from assessment of vascular flow parameters, from the health care provider's point of care, such as an office, to another facility housing the computer-based database. It is to be understood that the facility housing the computer-based database may be located locally, in the same office, the same building, or across town, or at a remote location such as in another city, state, country, or on a ship, plane or satellite.

The computer-based system may be configured to take advantage of data communications technologies and distributed networks, which makes it possible to deliver data to virtually anywhere in the world in an efficient and timely manner. This system in accordance with the present invention is capable of transferring clinical vascular flow data from a remote source to a central server via one or more networks. The central server hosts the computer-based database and related components. Accordingly, the central server is operable to analyze the received laboratory and clinical vascular data using an expert system, in order to produce information related to diagnoses, prognoses, decision supports, clinical data analyses and interpretations. The resulting information may then be delivered from the central server to one or more remote client stations via one or more networks. The entire process of transferring data from a remote source to a central server, analyzing the data at the central server to produce information, and transferring the information to a remote client site may thus be performed on-line and in real time.

In automated decision support system for interpreting the values of various parameters of blood flow in one or more vessels in assessing the vascular health of an individual, the data which are collected on an individual vessel are analyzed individually for each patient and then are also analyzed as an ensemble over that patient. In other words, all the vessels and their respective parameters, their respective health states, are compared to one another and an overall system analysis is made. The points of data in n-dimension states describing the health state of a vessel are tracked over time so as to determine a starting point and a velocity. The velocity in this case would be a direction of change as well as a rate of change in n-dimensional space. In more conventional terms, if noncompliance was detected in a vessel as one of the dimensions in n-dimensional space, then after a treatment one might see that number which represents noncompliance, or a degree of noncompliance migrate in a certain direction—for example, toward compliance—as the vessel becomes more compliant with the treatment intended to make it more compliant. The significance of that change will be assessed by looking at the velocity of health state movement in dimensional space across all of the individual's cerebral vasculature.

The movement from the baseline of any single vessel point may be hard to assess for statistical significance. However, there are statistical tools which are appropriate for analyzing the movement of the health states of all of the vessel points simultaneously. An example of that would be the Wilcox Test, which allows comparison of a group of non-parametric values to ascertain whether the variables are statistically different from one another or not. Other tests may be appropriate given the data set. However, fundamentally the process is to quantitate the health state of each vessel of an individual in a n-dimensional space and determine the significance of change and the direction of change, such that if the directions and the degrees of change are, when considered together, significant, it can then be concluded that the treatment is effective. In an individual case it is also possible to stop treatment and confirm that the effect being observed was in fact due to the drug by observing a reversal of the same.

When comparing a clinical trial treatment group to a control group, the process can be similar to what is being done with the individual. There, it is a matter of assessing whether or not the numbers quantitating particular characteristics of the vessel health state with regard to each of the dimensions in dimensional space can be construed to be significant. A discussion of the statistical analysis employed here is found in Jerrold H. Zar, Biostatistical Analysis, Prentice Hall, Inc. N.J., pp. 153-161, which is incorporated herein by reference.

One way in which the system of the present invention is trained is one wherein the software quantitates the rationale being used by the expert. In such a system, during this process the expert and the system come to mirror each other. In the process the expert is very specific, concrete and quantitative regarding the data analysis. In its turn, the software maintains a detailed bookkeeping of the analytical process. Thus, the software system and the expert each begin to diversify their respective roles in the development of this knowledge. The purpose of the software is to capture the expert's analysis.

According to the expert system of the present invention, characteristics of various functions for an automated decision support system for interpreting the values of various parameters of blood flow in one or more vessels in assessing the vascular health of an individual are provided. These characteristics can be derived from various functions, for example, transcranial Doppler readings at a left anterior carotid artery or basal artery test point, flow parameters for various arteries, a summary of patient data, a summary of clinical test(s) performed on a patient, the presence of vasodilators and/or vasoconstrictors in a patient, a stenotic pattern or pattern indicating constriction of an artery at a particular test point, a vasodilation pattern or pattern indicating dilation of a blood vessel, a noncompliance pattern or pattern indicating loss of compliance in an artery such as in the example of hardening of the artery, a normal pattern or pattern indicating a blood vessel with normal radius, a global vasoconstriction or reversible stenosis of vessels in the brain, global vasodilation or dilation of all cranial blood vessels, a pseudo-normalized pattern of constriction or dilation at an arterial test point, a pseudo-normalized pattern of loss of compliance in an artery, stenosis of a vessel due to blockage, dilation of an artery to compensate for loss of flow elsewhere, permanent dilation of an artery, noncompliance or a state in which a vessel's walls have lost flexibility, collateral flow through an artery or via reversal of flow, and/or patient risk assessment for any type of stroke.

Parameters for determining the various functions can include, but are not limited to, identification of the person taking the Doppler reading, the date of the reading, patient identification, a patient's sex, a patient's ethnic group, a patient's date of birth, a patient's drug usage including specific drugs, Doppler values, Doppler times, acceleration, flow direction, reading depth, the mean and/or standard deviation of the flow velocity in a vessel, the mean and/or standard deviation of the systolic acceleration in a vessel, the pulsatility index of a vessel. These parameters can be static values, inputted or retained within a database, or calculated ones. Other calculated parameters may include the calculation of the belief of whether there are vasodilators or vasoconstrictors present in the patient, which may be based upon the presence of vasoactive substances such as caffeine and/or methylxanthine. An example of another calculated parameter may include the belief of the severity of the constriction of an artery at a particular test point, which may be characterized as none, minimal, moderate or severe. An example of another calculated parameter of the present invention may include the belief of dilation of a blood vessel, which may be characterized as none, hyperemic, normal or pathological. An example of another calculated parameter of the present invention may include the belief of loss of compliance in an artery, which may be characterized as none, normal or pathological. An example of another calculated parameter of the present invention may include the belief of a blood vessel with normal radius, which may be characterized as none, hyperemic, normal or pathological. An example of another calculated parameter of the present invention may include the belief of a blood vessel with a high pulsatility index, or wherein the pulsatility index of one vessel is higher than another, which may be characterized as true or false. As can be seen from the above examples, various beliefs may be calculated according to the expert system of the present invention based upon the function studied.

An automated decision support system according to the present invention provides a domain ontology for interpreting the values of various parameters of blood flow in one or more vessels in assessing the vascular health of an individual. These parameters may be determined by means of a transcranial Doppler velocimetry technique, which is a noninvasive technique for measuring blood flow in the brain. According to this technique, an ultrasound beam from a transducer is directed through one of three natural acoustical windows in the skull to produce a waveform of blood flow in the arteries using Doppler sonography. The data collected to determine the blood flow may include values such as the pulse cycle, blood flow velocity, end diastolic velocity, peak systolic velocity, mean flow velocity, total volume of cerebral blood flow, flow acceleration, the mean blood pressure in an artery, and the pulsatility index, or impedance to flow through a vessel. From this data, the condition of an artery may be derived, those conditions including stenosis, vasoconstriction, irreversible stenosis, vasodilation, compensatory vasodilation, hyperemic vasodilation, vascular failure, compliance, breakthrough, and pseudo-normalization.

In order to best analyze a patient's risk of stroke, additional patient data is utilized by the automated decision support system according to the present invention. This data may include personal data, such as date of birth, ethnic group, sex, physical activity level, and address. The data may further include clinical data such as a visit identification, height, weight, date of visit, age, blood pressure, pulse rate, respiration rate, and so forth. The data may further include data collected from blood work, such as the antinuclear antibody panel, B-vitamin deficiency, C-reactive protein value, calcium level, cholesterol levels, entidal $CO_2$, fibromogin, amount of folic acid, glucose level, hematocrit percentage, H-pylori antibodies, hemocysteine level, hypercapnia, magnesium level, methyl maloric acid level, platelets count, potassium level, sedrate (ESR), serum osmolality, sodium level, zinc level, and so forth. The data may further include the health history data of the patient, including alcohol intake, autoimmune diseases, caffeine intake, carbohydrate intake, carotid artery disease, coronary disease, diabetes, drug abuse, fainting, glaucoma, head injury, hypertension, lupus, medications, smoking, stroke, family history of stroke, surgery history, and so forth.

The automated decision support system according to the present invention further considers related pathologies in analyzing a patient's risk of stroke, including but not limited to gastritis, increased intracranial pressure, sleep disorders, small vessel disease, and vasculitis. In a preferred embodiment, the invention includes a decision support system and method for screening potential participants in a drug trial. General references detailing principles and terms known to those skilled in the art of decision support systems include (1) Schank, R. C. and Abelson, R., Scripts, Plans Goals and Understanding, Hillsdale, N.J.: Lawrence Erlbaum Associates (1977); (2) Schank, R. C. and Riesbeck, C. K., Inside Computer Understanding, Hillsdale, N.J.: Lawrence Erlbaum Associates (1981); (3) Sacerdoti, E. D., A Structure for Plans and Behaviors, New York: Elsevier (1978); (4) Rinnooy Kan, A. H. G., Machine Scheduling Problems, The Hague: Martinus Nijhoff (1976); and (5) Charniak, E., Riesbeck, C. K. and McDermott, D., Artificial Intelligence Programming, Hillsdale, NJ: Lawrence Erlbaum Associates (1980).

Several terms used in disclosure of the present invention are described generally by the following definitions accepted by those skilled in the art—

Concept Graph: a knowledge representation of the dependencies between observable data values and higher level computations and assertions made about the data. A concept graph can be implemented as a directed acyclic graph of concept nodes that is a particular type of augmented transition network (ATN).

Decision Support System: a computer program that uses a knowledge base to assist in solving problems. Most expert systems use an inference engine to derive new facts and beliefs using a knowledge base.

Inference Engine: a computer program that infers new facts or beliefs from known facts or beliefs using a knowledge base and a set of logical operations.

Knowledge Base: a collection of knowledge (e.g., objects, concepts, relationships, facts, rules, etc.) expressed in a manner such that it can be used by an inference engine. For example, a knowledge base may include rules and facts or assertions as in traditional expert systems.

Figure 10:
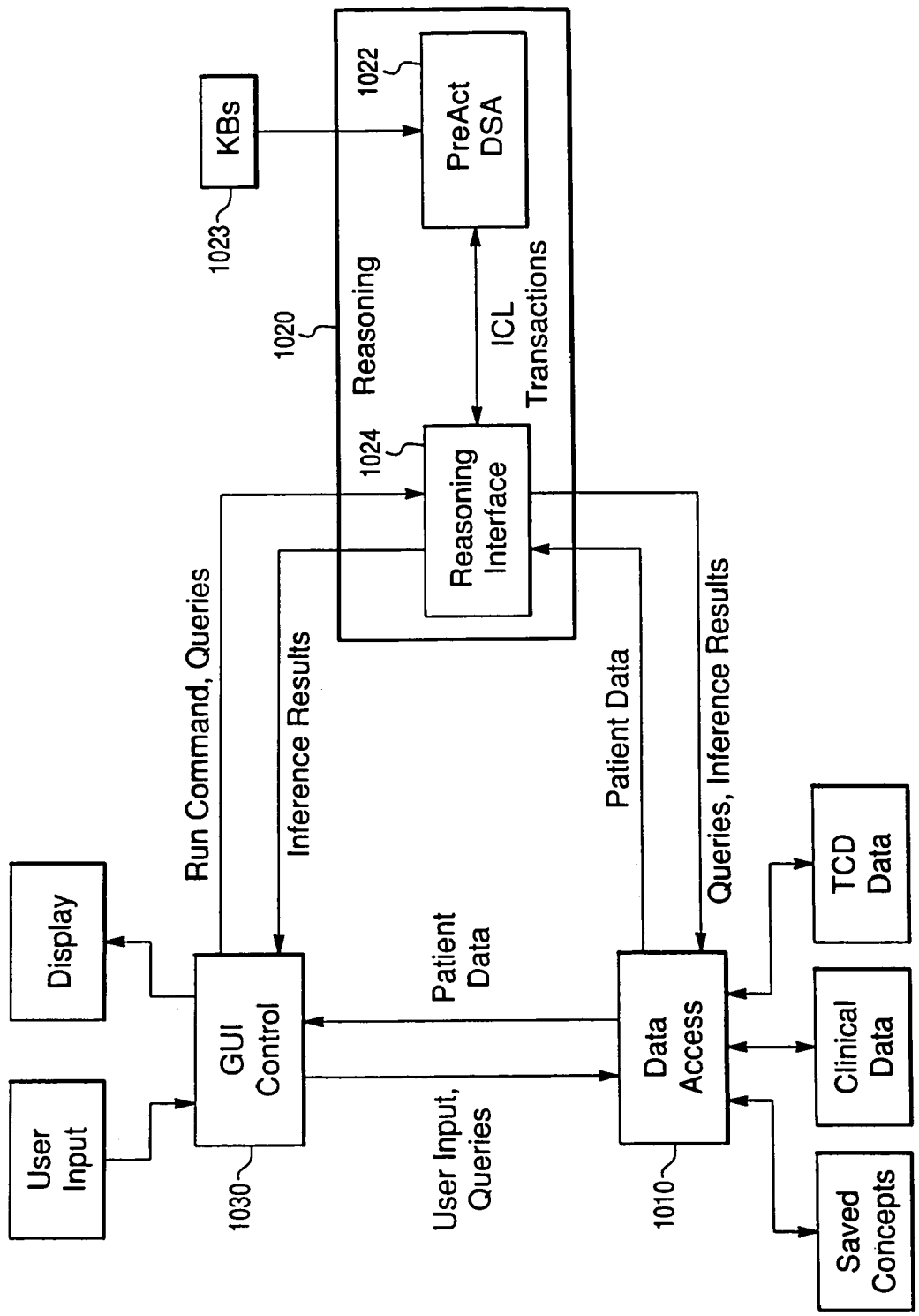
FIG. 10 is a block diagram of an illustrative system architecture of a preferred embodiment of the invention.
Figure 11:
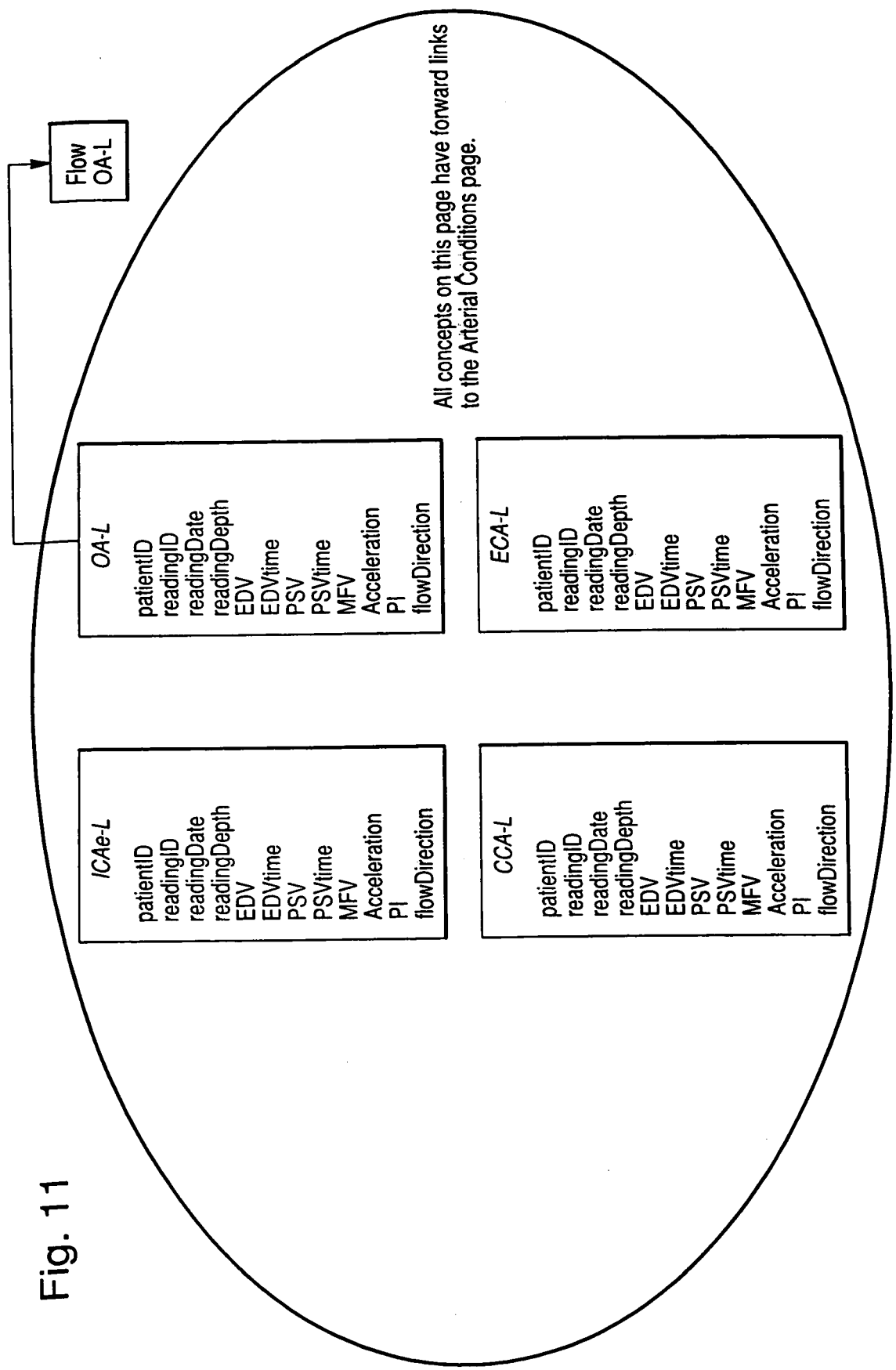
FIG. 11 is a concept graph of left extracranial frontal artery concepts of a preferred embodiment of the invention.
Figure 12:
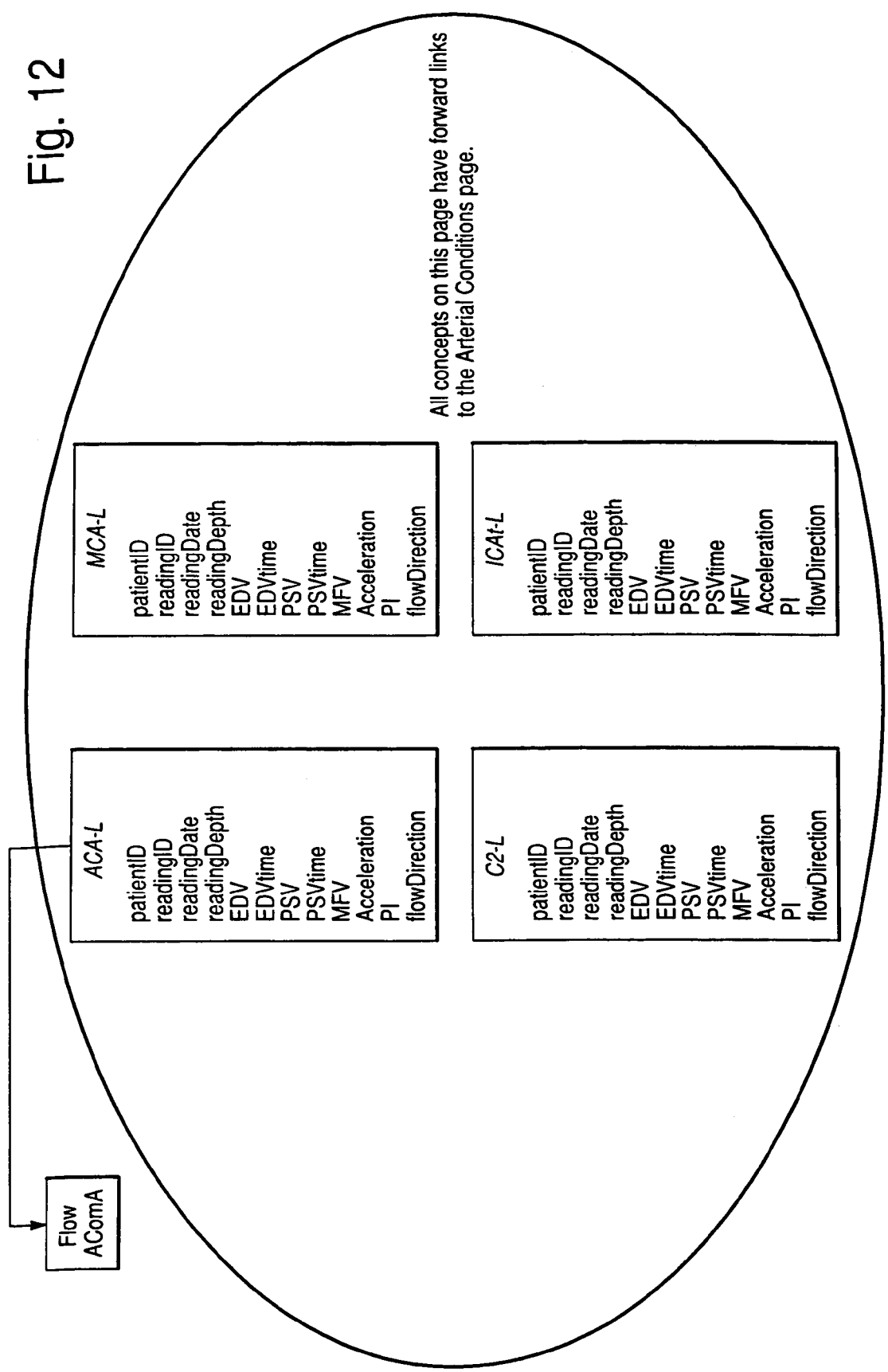
FIG. 12 is a concept graph of left intracranial frontal artery concepts of a preferred embodiment of the invention.
Figure 13:
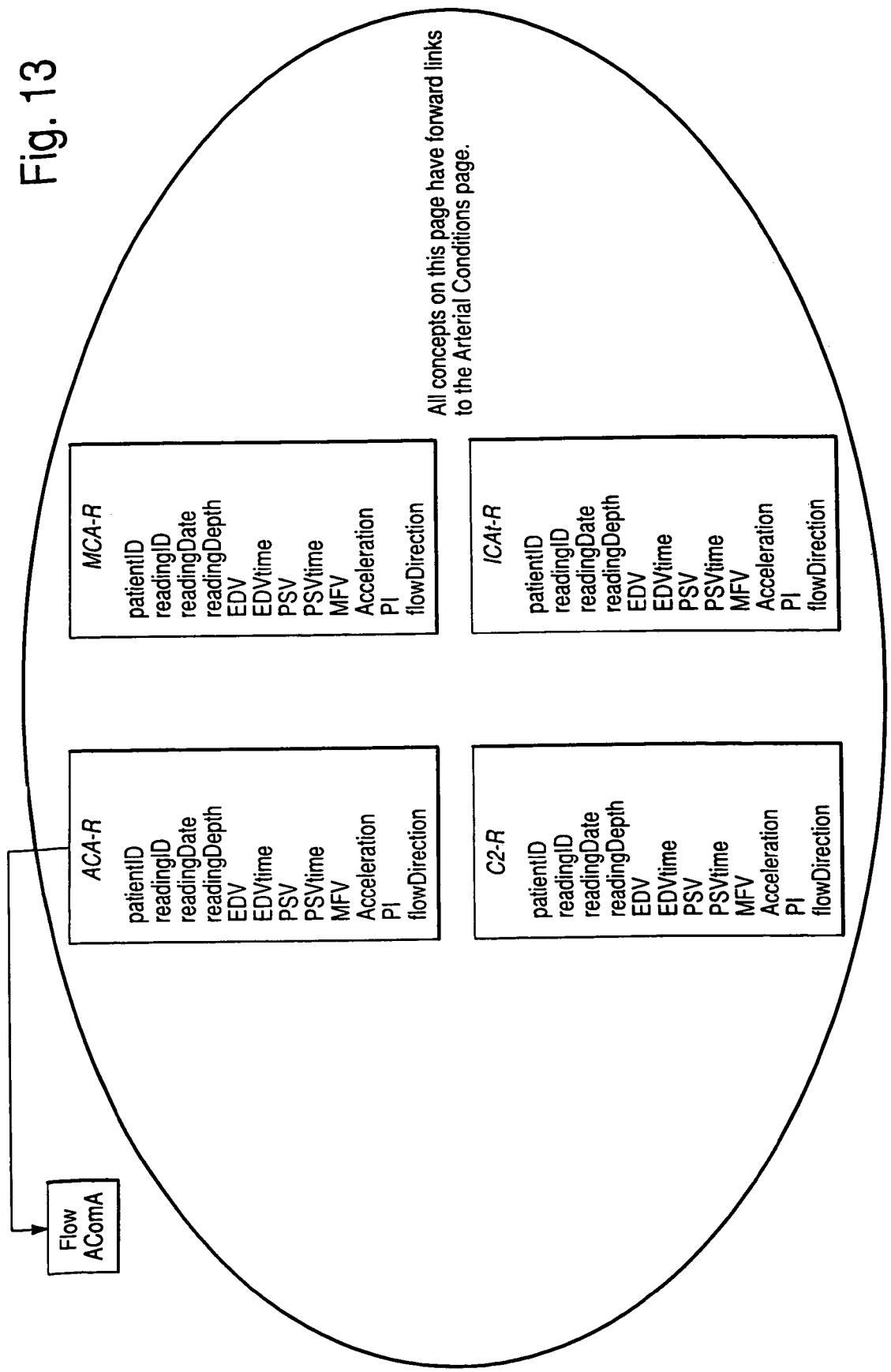
FIG. 13 is a concept graph of right intracranial frontal artery concepts of a preferred embodiment of the invention.
Figure 14:
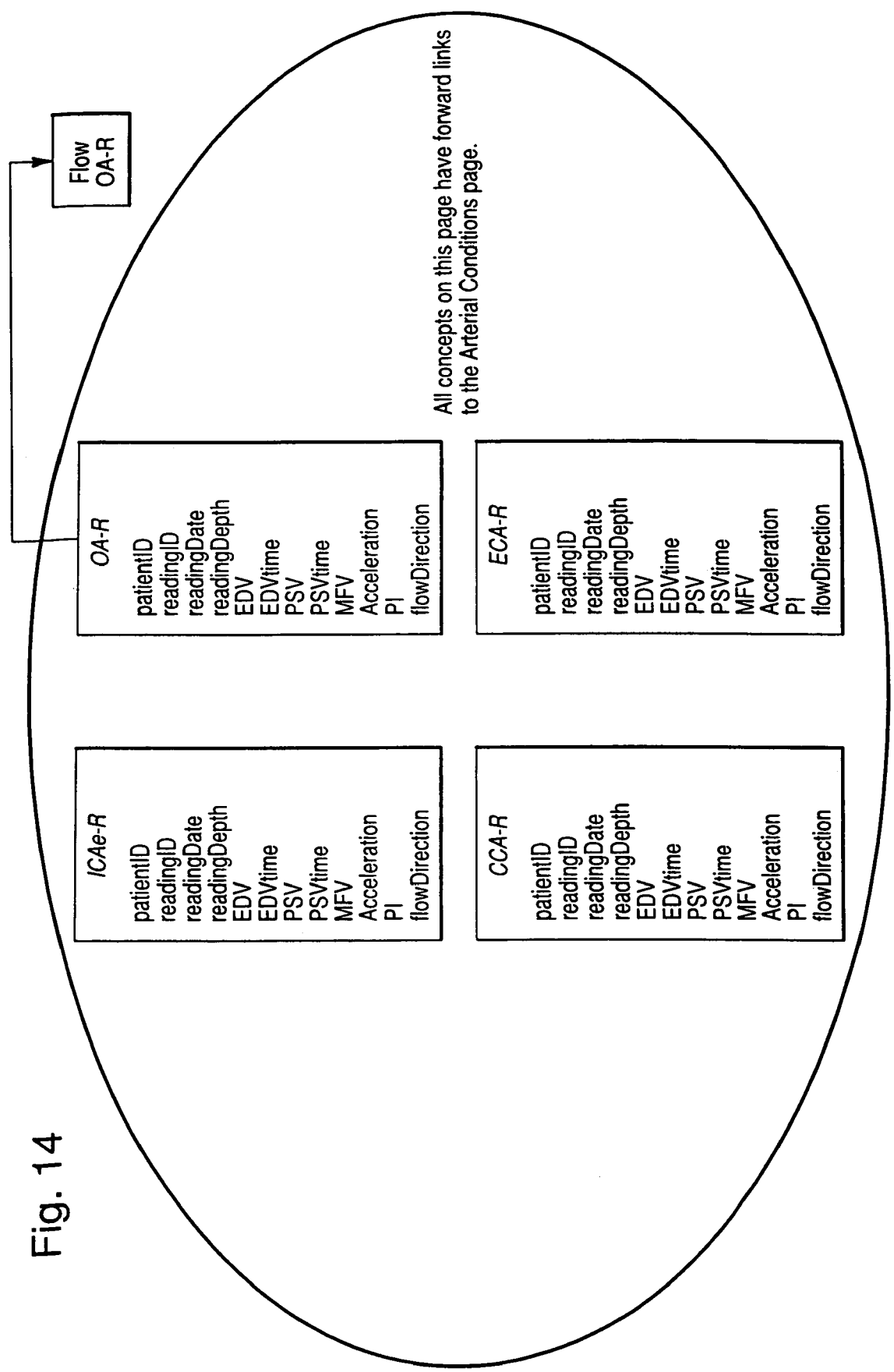
FIG. 14 is a concept graph of right extracranial frontal artery concepts of a preferred embodiment of the invention.
Figure 15:
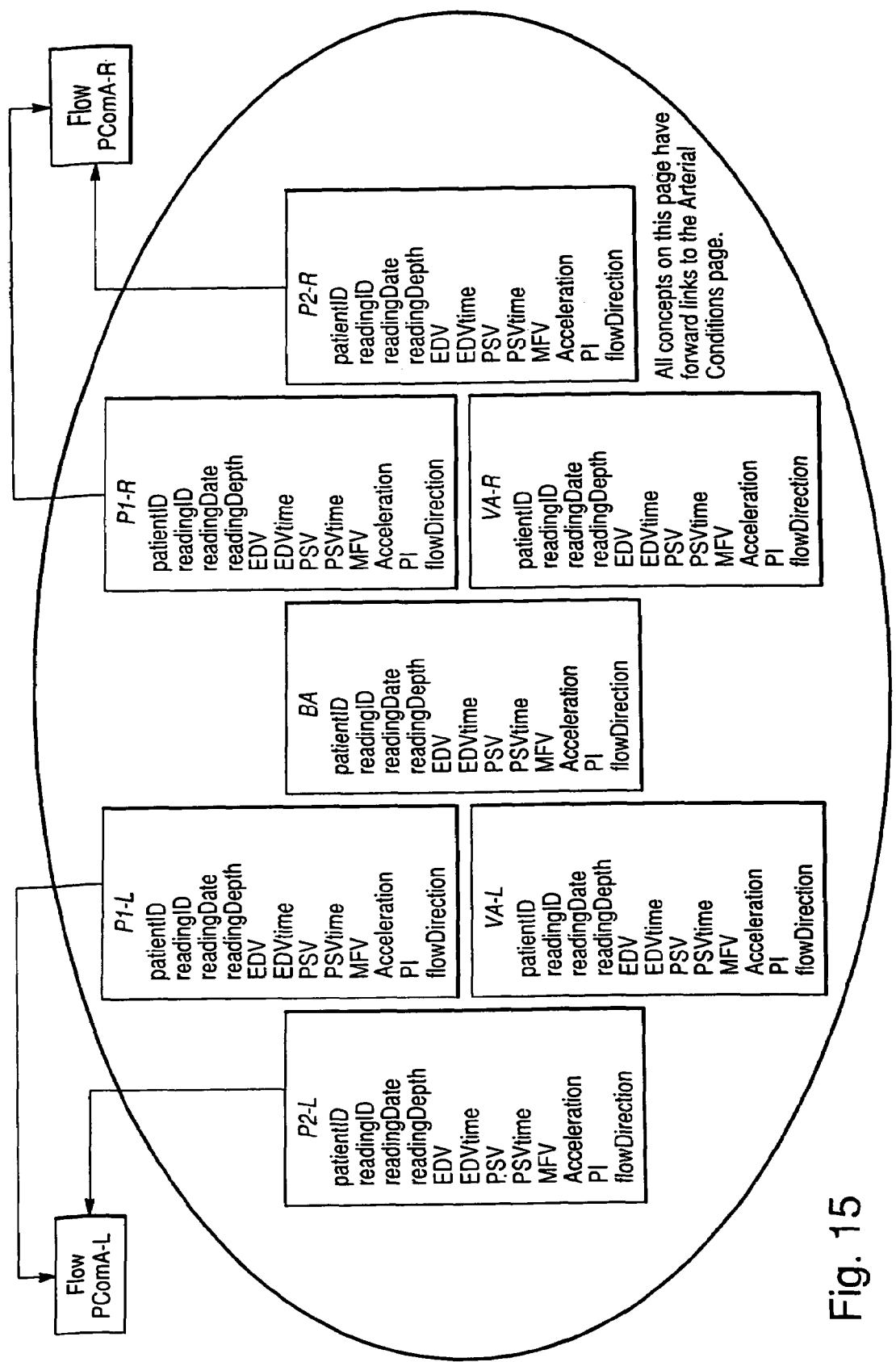
FIG. 15 is a concept graph of posterior artery concepts of a preferred embodiment of the invention.
Figure 16:
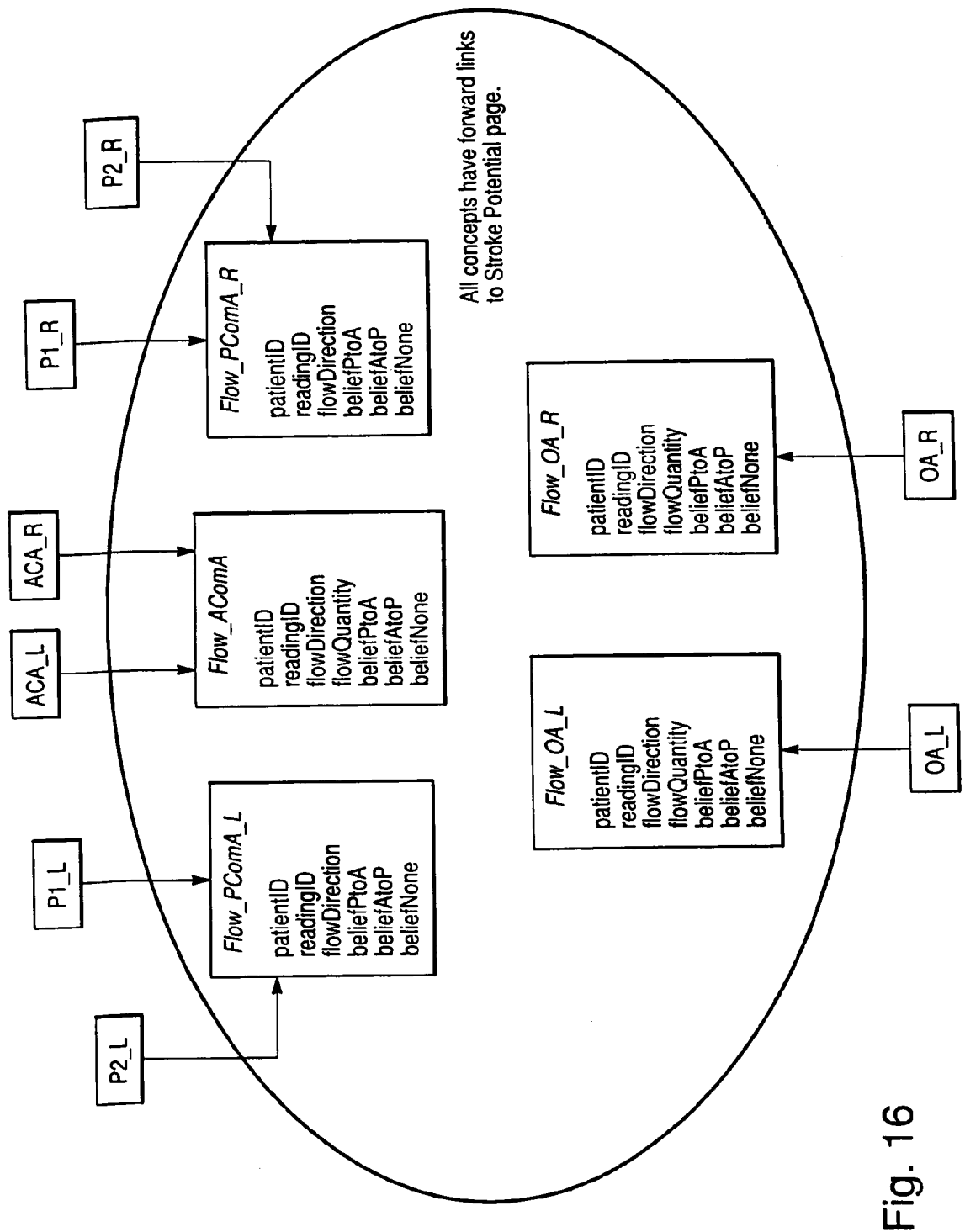
FIG. 16 is a concept graph of collateral flow concepts of a preferred embodiment of the invention.
Figure 17:
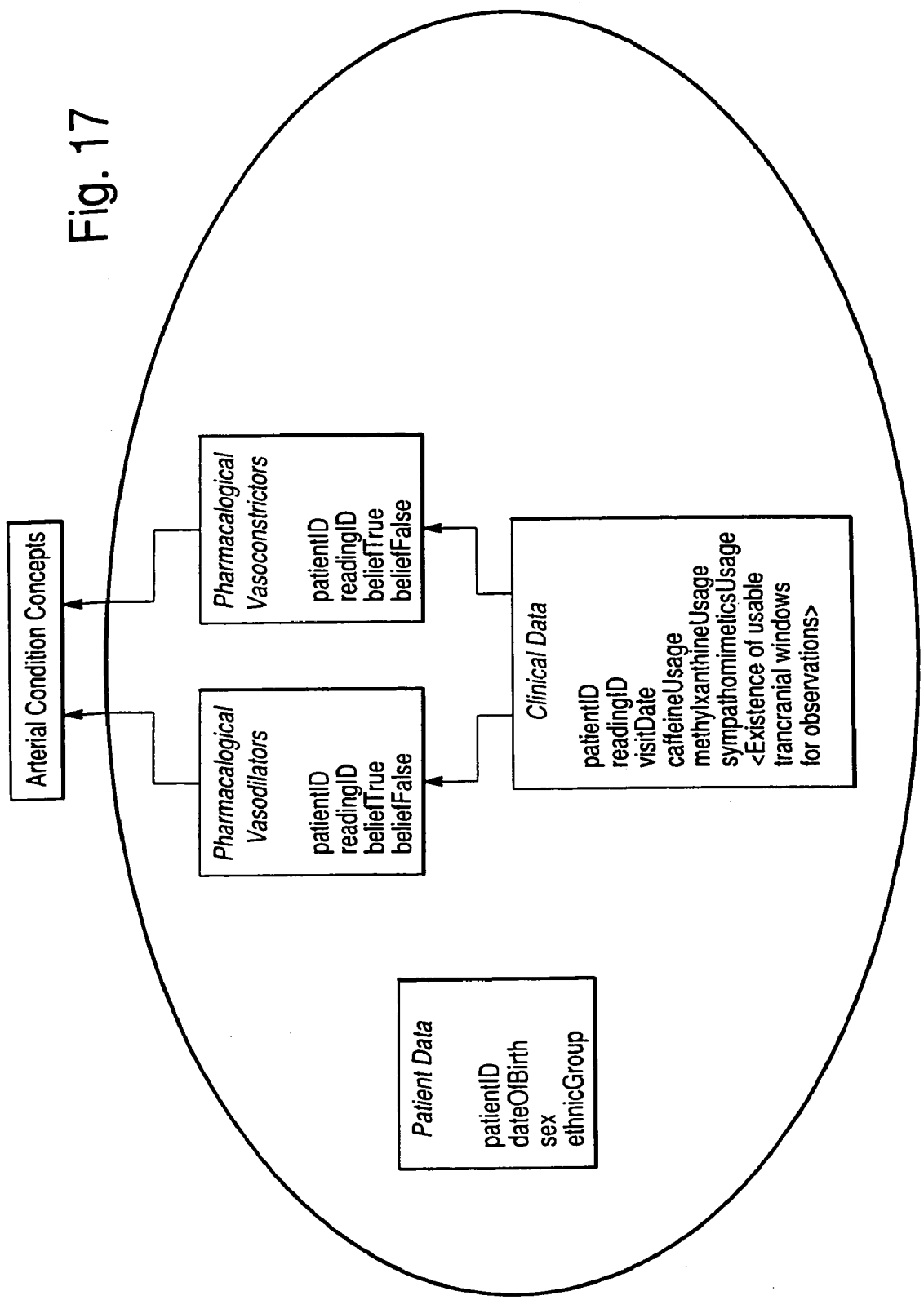
FIG. 17 is a concept graph of parameter concepts of a preferred embodiment of the invention.
Figure 18:
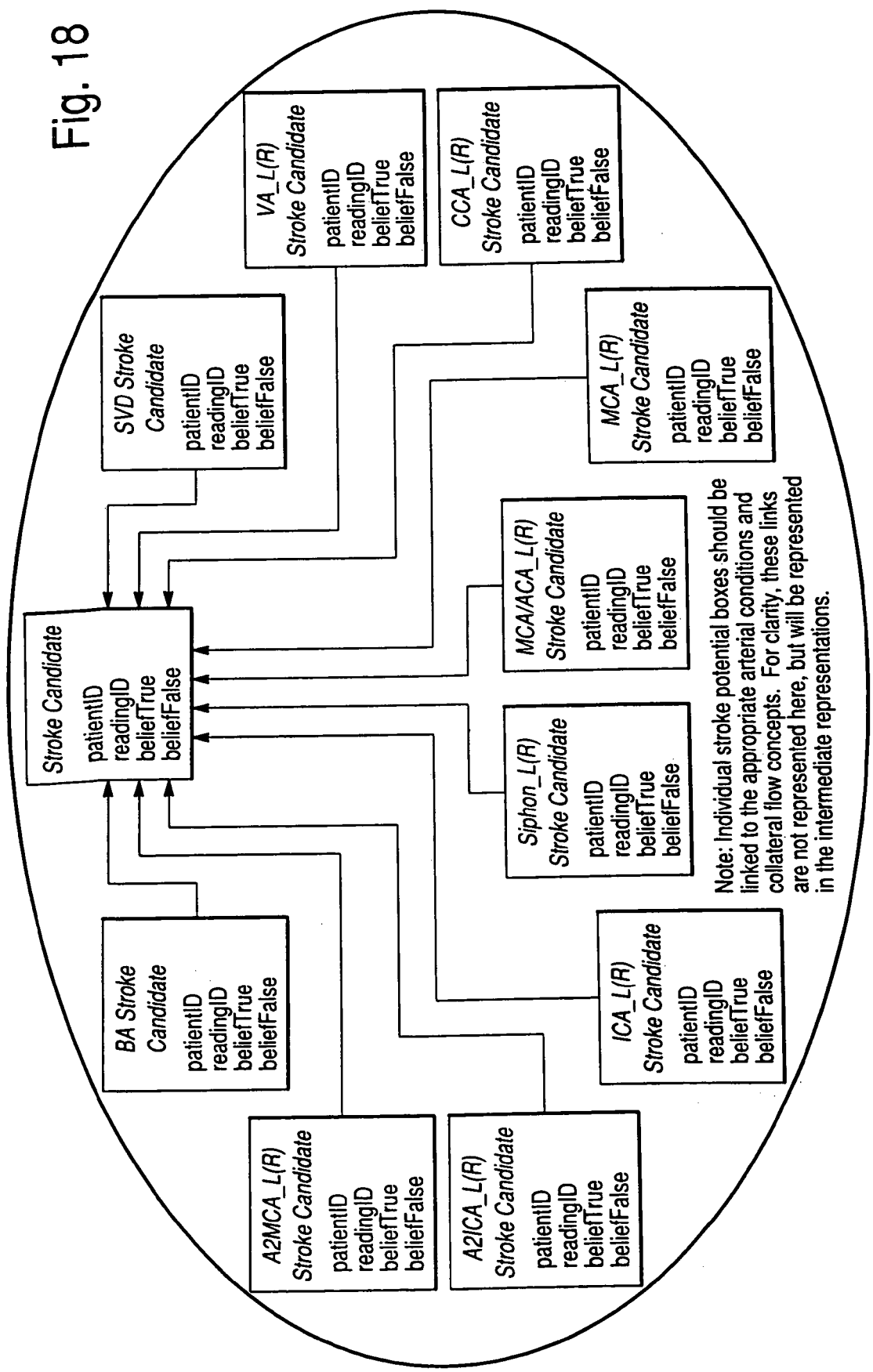
FIG. 18 is a concept graph of stroke candidate concepts of a preferred embodiment of the invention.
Figure 19:
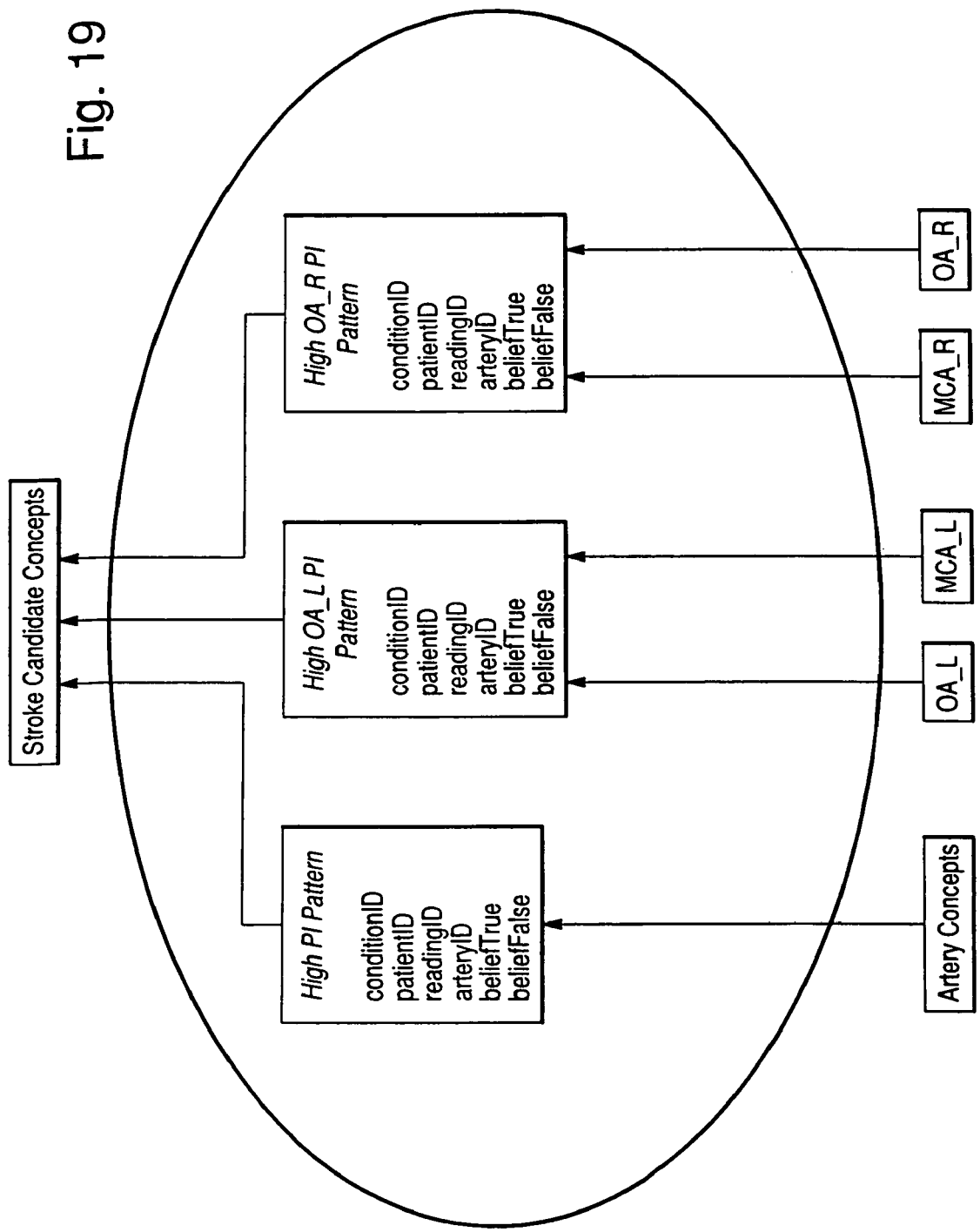
FIG. 19 is a concept graph of small vessel disease concepts of a preferred embodiment of the invention.
Figure 20:
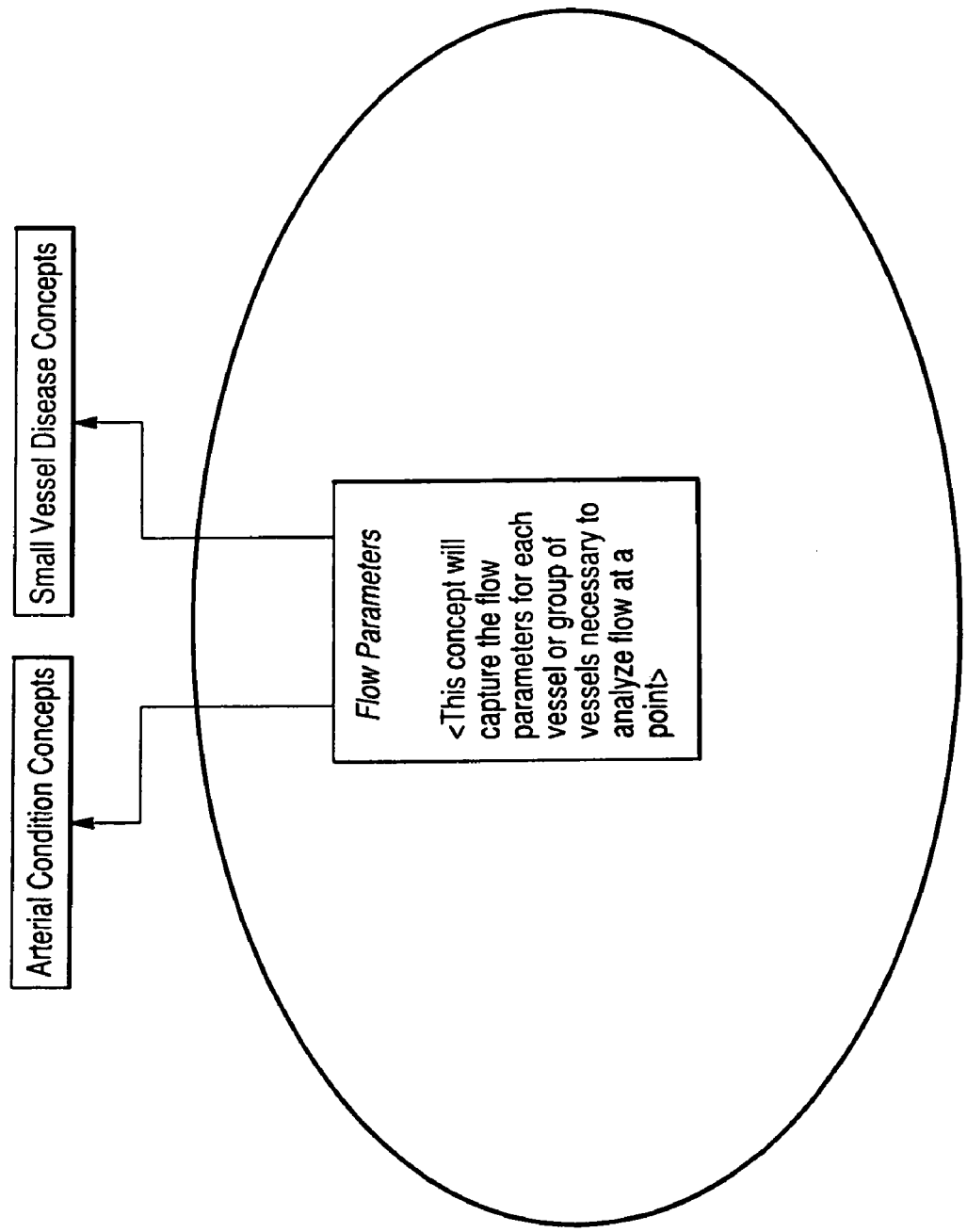
FIG. 20 is a concept graph of data concepts of a preferred embodiment of the invention.
Figure 21:
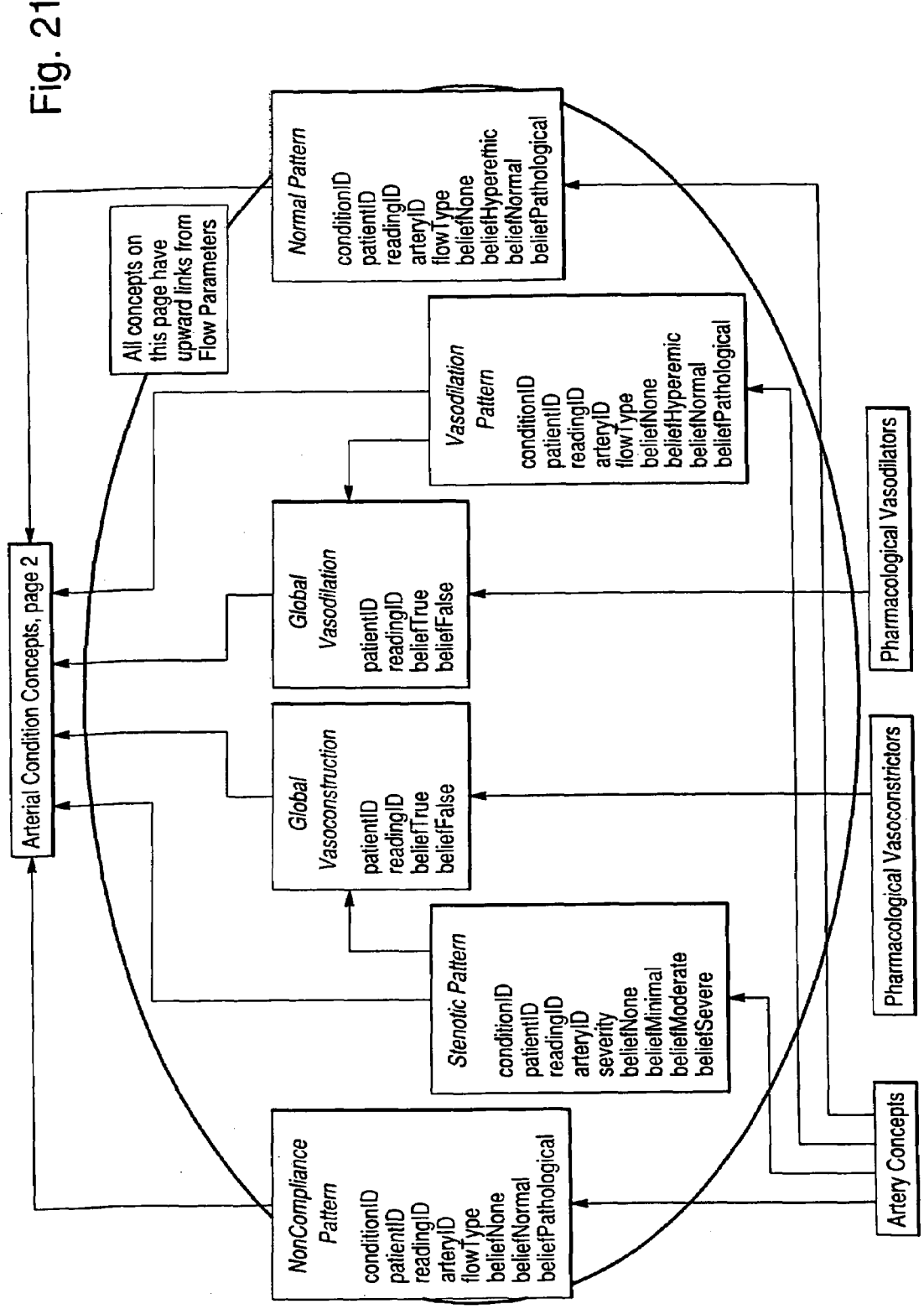
FIG. 21 is a concept graph of arterial condition concepts of a preferred embodiment of the invention.
Figure 22:
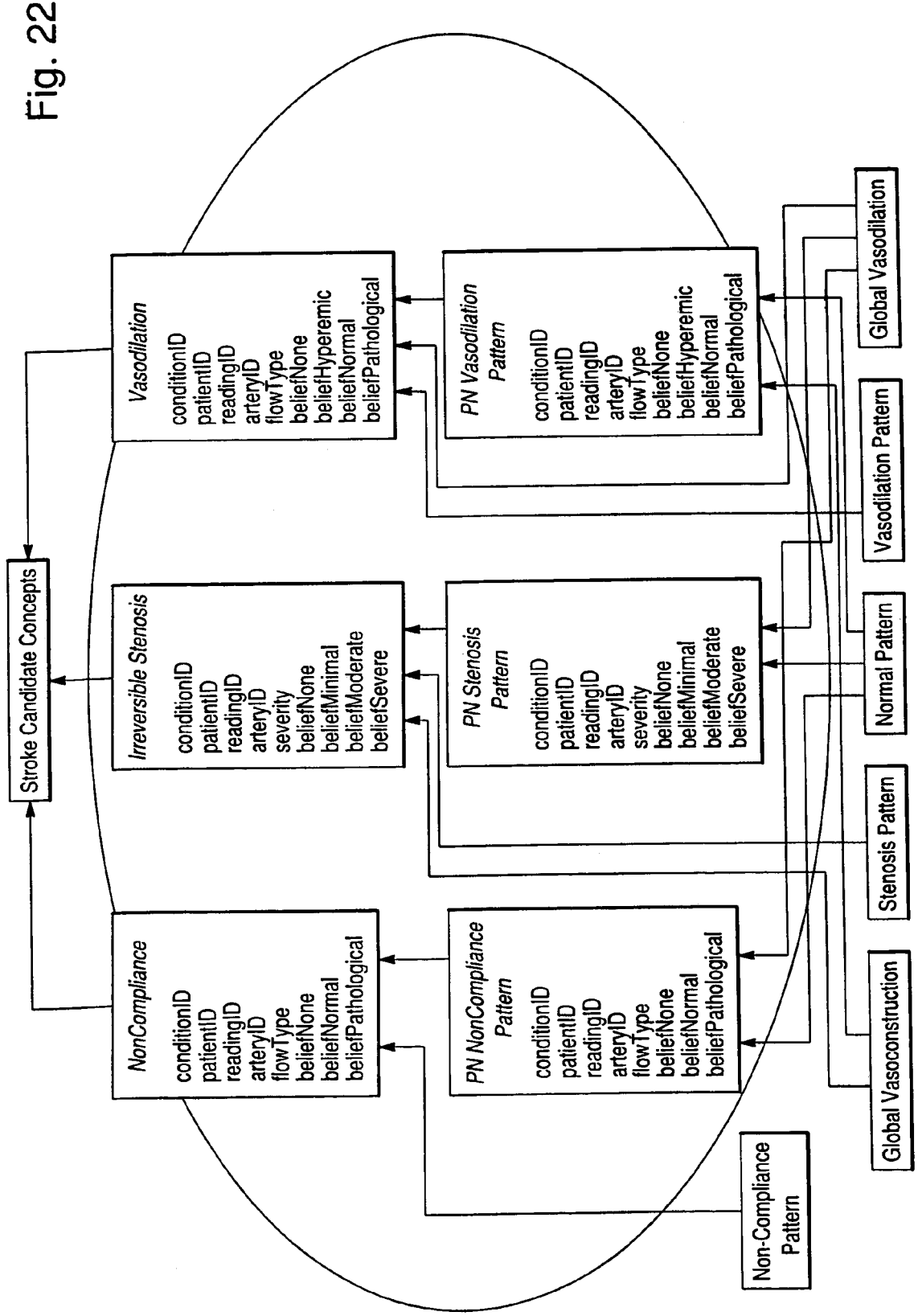
FIG. 22 is a concept graph of arterial condition concepts of a preferred embodiment of the invention.

One preferred embodiment of a decision support system of the present invention includes the ability to assess the hemodynamic state of a subject's cerebrovasculature through the use of transcranial Doppler measurements. Referring to FIG. 10 the embodiment consists of three software modules: a Data Access 1010 module, a Reasoning 1020 module, and a Graphical User Interface (GUI) module 1030. The Reasoning 1020 module consists of two sub-modules: a situation assessment module comprising the PreAct DSA 1022 sub-module from Applied System Intelligence, Inc., including the domain knowledge base 2362; and Reasoning Interface 1024 sub-module. Cognitive engines, other than DSA, may be used. The Reasoning Interface 1024 sub-module serves to hide the details of interacting with the DSA 1022 sub-module from other objects. In this embodiment, these modules run sequentially as part of the same process, with one instance of each module.

The Data Access 1010 module provides access and storage methods for TCD measurement/data, clinical data, and inferences from the Reasoning 1020 module. In a preferred laptop personal computer configuration this collection of data is stored in a file.

The GUI 1030 module processes user input to be sent to the Data Access 1010 module, runs commands for the Reasoning 1020 module, queries about patient data for the Data Access 1010 module, and queries about inference results for the Reasoning 1020 module. The GUI 1030 module also displays patient data received from the Data Access 1010 module and concept instances, related to the concept graph instances received from the Reasoning 1020 module.

The PreAct DSA 1022 sub-module accepts leaf-level concepts representing patient data and processes them for inferred concepts such as disease. The current concept graph may be queried for all instances of a particular concept pattern or for evidence supporting a particular instance. The current graph may be saved for future queries and saved concept graphs may be reloaded for querying. The DSA 1022 sub-module also has access to the underlying knowledge base 2362. The Reasoning Interface 1024 sub-module accepts commands to process patient data for inferred concepts, to search for instances of particular concepts or evidence for a given concept instance in the active concept graph, and to save the current concept graph or load a saved concept graph. The Reasoning Interface 1024 sub-module converts these commands into a command language understood by the DSA 1022 sub-module.

This preferred embodiment makes use of the data structures found in Table 1.

TABLE 1

| DATA | DEFINITION |
|---|---|
| Patient ID | Uniquely identifies each patient |
| Group ID | Uniquely identifies each group of patients in the |
| Patient data block | Contains TCD data and clinical data for a patient. This includes: Data and measurement times for each vessel test point; Demographic data, e.g., date of birth, ethnic group; Clinical data, e.g., vital signs, test results |
| Filename | Name of a concept graph file |
| Concept pattern ID | Unique identifier of a concept pattern |
| Concept key ID | Unique key of a concept in stance |
| Concept instance | Concept instance from a concept graph. Derived |
| List of concept | List of concept instances from a concept graph |
| List of concept | List of keys for instances of a certain pattern |

Patient data consists of data derived from TCD measurements and clinical data. This data is used to fill in the leaf-level concepts in the concept graph. Patient data is accessed and stored as a single block of data for each patient, referenced by a unique patient ID.

TCD measurements and data may be input in a streaming fashion via a network or direct connection or as a file. Clinical data may be input as a file or manually through the GUI 1030 module. After completing data input, the user may elect to save the data or file for later access or to analyze the data. In either case, the Reasoning 1020 module retrieves patient data via the Data Access 1010 module. For this purpose, the GUI 1030 module stores data in a file. Both modules retrieve patient data by patient ID. Additionally, in order to allow a user to select a patient's data to view, edit, or analyze, the interface allows the GUI 1030 module to retrieve a list of all patients saved in a file. In preferred embodiments, the set of parameters passed to Data Access 1010 module functions includes a user ID.

Inference data includes concept instances in the concept graph for a particular patient. The DSA 1022 sub-module provides its own accessors for loading a concept graph from a text file and saving a concept graph to a text file. The Data Access 1010 sub-module is responsible for storing the file created by the Reasoning 1020 module. Table 2 identifies commands used by the Data Access 1010 module.

TABLE 2

| COMMAND | USED BY | PARAMETERS | RETURN |
|---|---|---|---|
| Initialize Module | System layer | None | Success/failure |
| Retrieve Patient Data | GUI control, Reasoning | Patient ID, user ID | Patient data block |
| Save Patient Data | GUI control | Patient ID, user ID | Success/failure |

TABLE 2-continued

| COMMAND | USED BY | PARAMETERS | RETURN |
|---|---|---|---|
| Delete Patient Data and Concept Graph | GUI control | Patient ID, user ID | Success/failure |
| Retrieve List of Patients | GUI control | User ID | List of patient IDs |
| Store Patient Concept Graph | Reasoning | Patient ID, user ID, filename accessible by Data Access Module | Success/failure |
| Retrieve Patient Concept Graph | Reasoning, GUI | Patient ID, user ID | Filename accessible by Reasoning Module |
| Query Database | GUI | SQL Query | Query result |

The GUI 1030 module accepts input from the user, converts the user's input in to data and commands for other modules, and displays the values returned on the screen or in a printout. The GUI 1030 module provides for display of clinical and demographic data for a patient, raw TCD data and measurements, and an analysis of a patient's hemodynamic state. The analysis of a patient's hemodynamic state includes the condition of each artery for which TCD measurements are available, any global conditions found, and an assessment of the patient's risk for stroke. The GUI 1030 also allows a user to drill down from a patient's risk for stroke to determine how that conclusion was reached.

The Reasoning Interface 1024 sub-module allows other modules to access the concept stored in the DSA 1022 sub-module without being exposed to all the details of the DSA 1022's interface. Reasoning Interface 1024 sub-module commands include those in Table 3.

TABLE 3

| COMMAND | USED BY | PARAMETER | RETURN |
|---|---|---|---|
| Initialize module | System layer | None | Success/failure |
| Run module with a patient's data | GUI control | Patient ID, user ID | Success/failure |
| Get concept instances | GUI control | Concept pattern ID | List of concepts |
| Get concept instance | GUI control | Concept pattern ID, concept key ID | Concept |
| Get concept evidence | GUI control | Concept pattern ID, concept key ID | List of concepts |
| Load a patient's concept graph | GUI control | Patient ID, user ID | Success/failure |
| Save a patient's concept graph | GUI control | Patient ID, user ID | Success/failure |

The DSA 1022 sub-module includes methods for commanding the sub-modules, including commands for initializing, starting, running, and stopping. The DSA 1022 sub-module also includes services for setting and retrieving concept attribute values.

Requests for DSA 1022 sub-module data are responded to with one of three values: 1—data found correctly; 0—data not found but no critical error occurred; and—1—critical error, see exception log file. In addition to requesting the value of a particular attribute in a known concept instance, the invention can request both an index of concepts and a deep copy of a particular concept instance. The system also responds to: a user request for a list of all child concept instances of a particular concept instance; a user request to clear all concept instances from the concept graph (patterns will remain loaded); a user request to save a concept graph to a specified file name (in preferred embodiments, this file will be saved as an XML file); and a user request to load a saved concept graph from a specified file name.

In a broad sense, this preferred embodiment allows as user to enter new patient data through the GUI 1030 and save the data; load existing patient data from a database; view raw data, e.g., clinical data and TCD data; analyze patient data for inferences about the patient's hemodynamic state; view results of an analysis; and view the evidence used to reach a particular inference.

Upon initialization, a main program instantiates and initializes the modules and sub-modules in the following order: Data Access 1010, Reasoning Interface 1024 (which will initialize the DSA 1022), and GUI 1030. After initialization is complete, control is passed to the GUI 1030. Control remains with the GUI 1030 until the user signs out, at which point the main program shuts down the modules in the reverse order of initialization. The Reasoning Interface 1024 module shuts down the DSA 1022.

Specific operation of the GUI 1030 module can include being initialized by one or more external commands. Operation of the GUI 1030 can further include accepting a user commands to sign in to the system; change the group of patients currently being processed (contingent upon authority of that user to have access to the data for the new group); create a new group; sign out of the system; create a new patient record; process a patient's data for inferences; edit data for a new or existing patient; save a patient's data; display a list of subjects in the specified group (including an indication of whether or not a hemodynamic analysis has been done on the patient's data; display patient data for an existing patient; display patient's overall risk of stroke; display an explanation of a patient's stroke risk, including concepts used as evidence and the ability to drill down in to evidence for further detailed display; and display the status of arterial flow in all the patient/subject's arteries for which data is available, including flow characteristics at each test point, global characterizations of blood flow, and the direction of blood flow.

Specific operation of the Data Access 1010 module can include serving as an interface to an existing relational database management system; accepting commands for initialization, shutdown, creation of a new patient record, retrieval of the patient data block for a specified patient, update of a patient's data, deletion of a record, retrieval of a concept graph, update of a concept graph, deletion of a concept graph; and accepting a query for a list of all patients in the database.

Specific operation of the Reasoning Interface 1024 sub-module can include initialization by one or more external commands; accepting commands for processing a patient's data, saving the analysis of the current patient's data, loading a saved analysis, and stop processing; and accepting queries for instances of particular concept patterns in the concept graph, a particular concept instance, and further explanation of a concept instance.

Specific operation of the DSA 1022 sub-module can include initialization by one or more external commands; and use of knowledge bases to store concept patterns and knowledge base algorithms used to infer concepts from leaf-level data provided, with the basis for the inferences being the TCD data and clinical data. The algorithms infer the concepts in several intermediate steps, each represented in the concept graph, such that it is sufficient for one skilled in the art of the problem domain to follow the chain of reasoning. The conditions represented in the concept graph include, but are not limited to, vasodilation, hyperemic vasodilation, pathological vasodilation, non-compliance, and irreversible stenosis. The concept graphs provide a path for following a chain of reasoning backwards from a conclusion. The algorithms use a plurality of reasoning techniques, e.g., Bayesian reasoning, to look for supporting data in related concepts. Further operation of the DSA 1022 sub-module can include loading knowledge bases; accepting patient data to be processed through transactions; allowing the user to save the concepts resulting from an inference and load saves concepts; and querying for instances of particular concept patterns in the current concept graph, particular concept instances, and further explanation of a concept instance. This querying can include accepting a clear command, and in response, clearing all concept instances from the current graph; concept patterns remain loaded; accepting a kill command to release all allocated memory and terminate; and writing non-fatal errors to a log file.

In another preferred embodiment, the invention is a networked based system and method for analyzing the hemodynamic state of a subject based on TCD measurements. When using this embodiment, a user submits data to a centralized system for analysis similar to that described in the previous embodiment.

Figure 23:
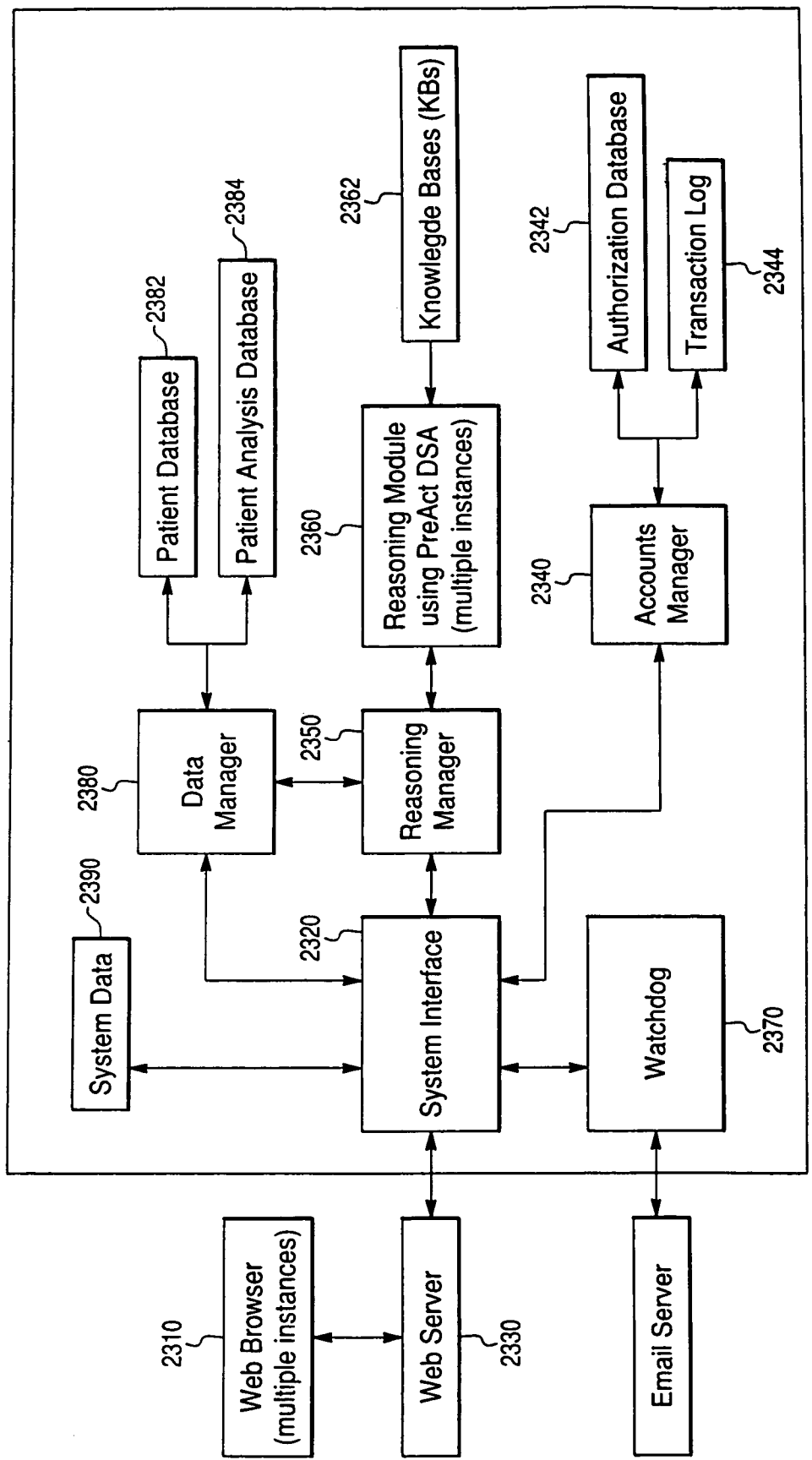
FIG. 23 is a block diagram for an application service provider architecture of a preferred embodiment of the invention.

Referring to FIG. 23 a block diagram illustrating the context and relationship between modules for the preferred Application Service Provider (ASP) embodiment is shown. The modules run in separate process spaces. The user interface (one or more instances of a Web Browser 2310) and System Interface 2320 are connected via a network, in this case the Internet, using connection protocols known to those skilled in the art of computing. The System Interface 2320 Manager provides an adaptive layer between the web server and the remainder of the system. The Accounts Manager 2340 maintains authorization and accounting data for each user account. The Reasoning Manager 2350 manages requests for analysis of data and queries of existing analyses. It also maintains connections to one or more instances of the Reasoning Module 2360. The Reasoning Module 2360 encapsulates a DSA component in a fashion similar to the earlier described embodiment. The DSA component uses the invention's knowledge base to analyze TCD data and provide access to results. The Reasoning Module 2360 provides translations to and from the interface language use by the DSA component. The Watchdog 2370 monitors invention performance for functioning within acceptable parameters.

Figure 24:
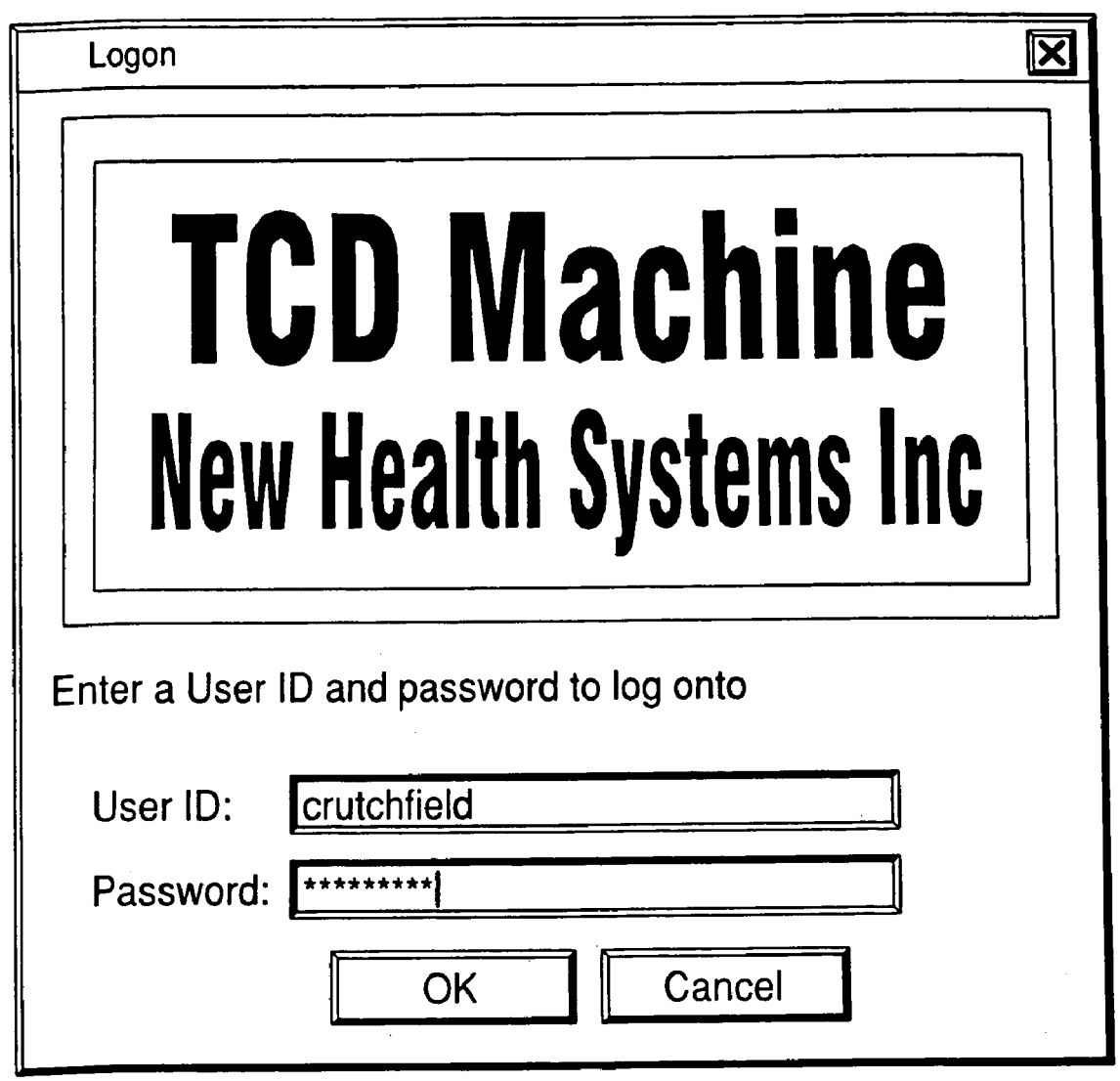
FIG. 24 is an illustration of a logon page of a preferred embodiment of the invention.
Figure 25:
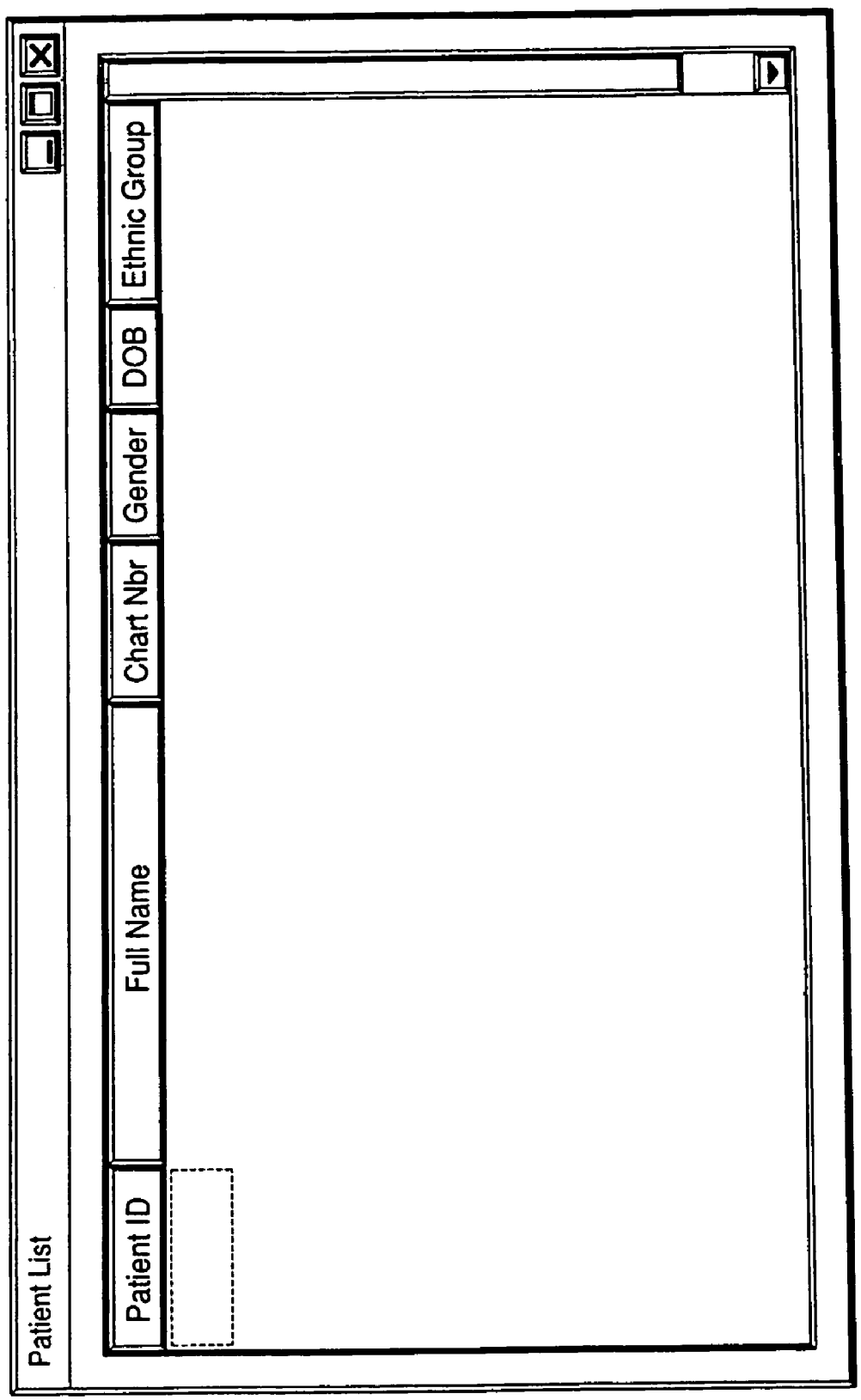
FIG. 25 is an illustration of a user startup window of a preferred embodiment of the invention.
Figure 27:
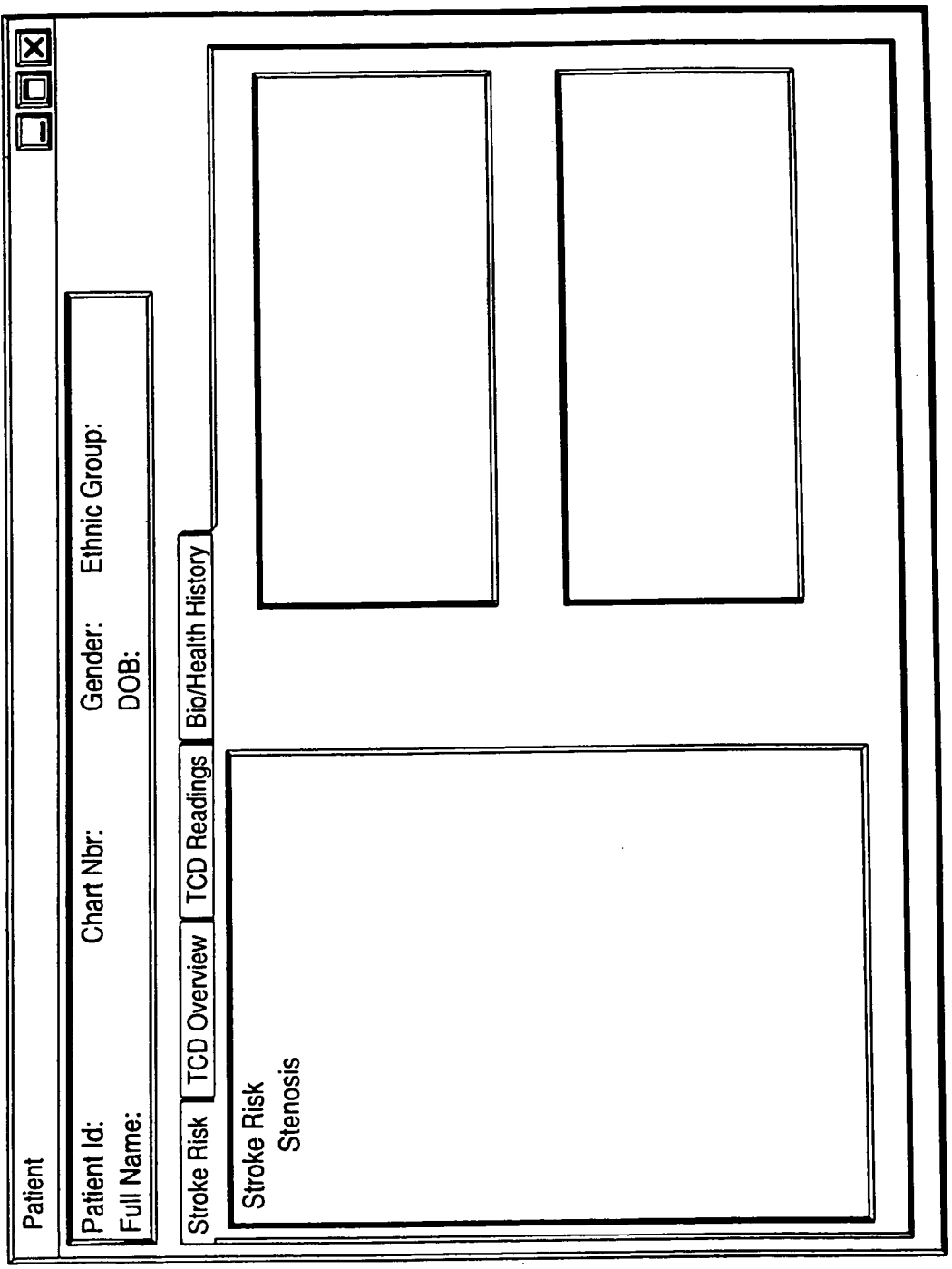
FIG. 27 is an illustration of a hemodynamic analysis window of a preferred embodiment of the invention.
Figure 28A:
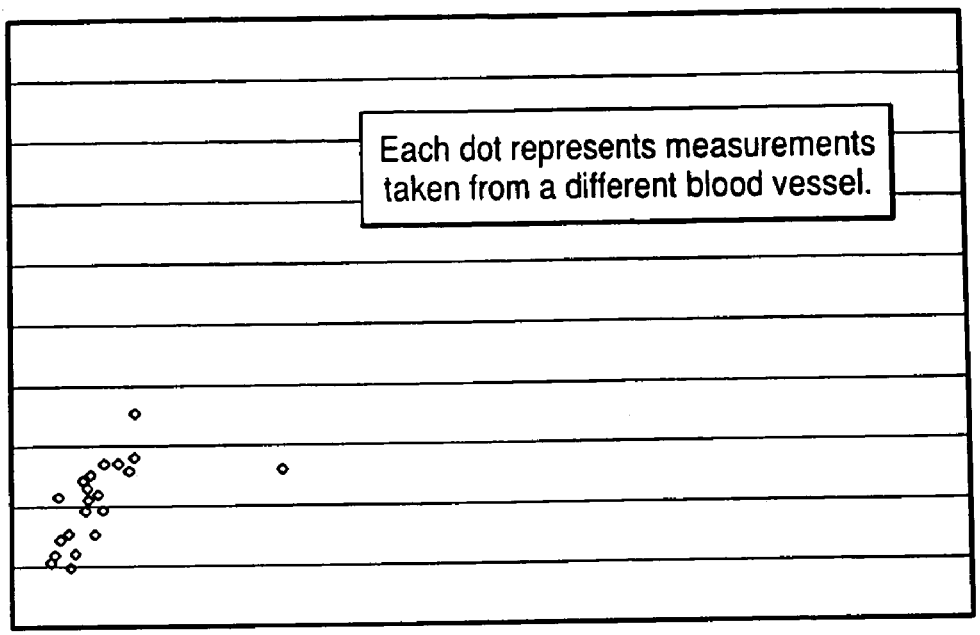
FIG. 28A depicts the global vascular status of a subject based on data from a number of vessel at the initial onset of symptoms associated with an increase of intracranial pressure.
Figure 28B:
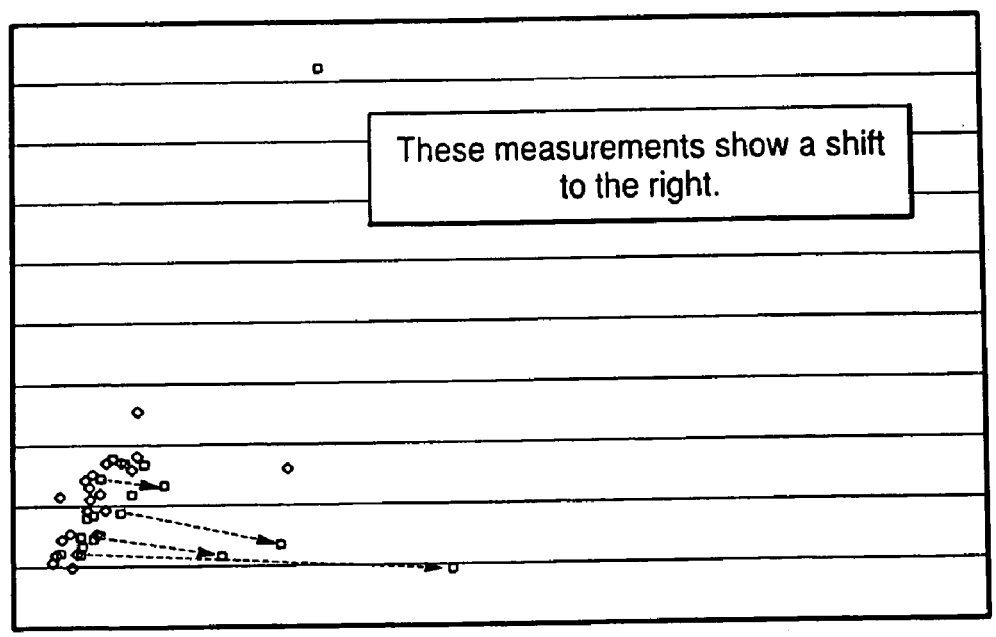
FIG. 28B depicts a shift in vascular status in individual vessels as the subject's symptoms have progressively worsened.
Figure 28C:
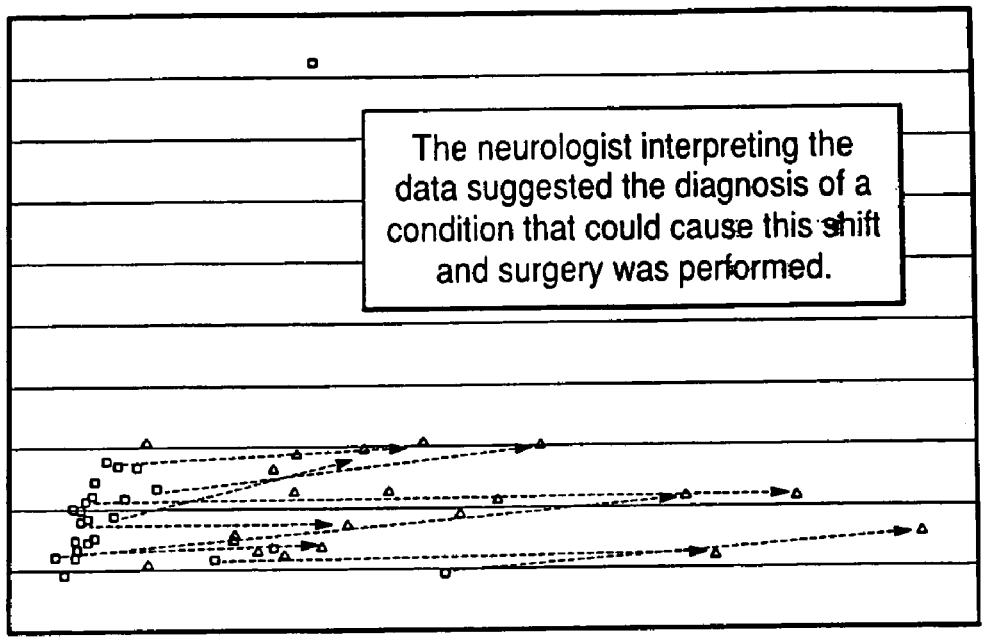
FIG. 28C depicts a dramatic globalized shift in vascular status of individual vessels after the subject's symptoms have increase to the point of requiring hospitalization.
Figure 28D:
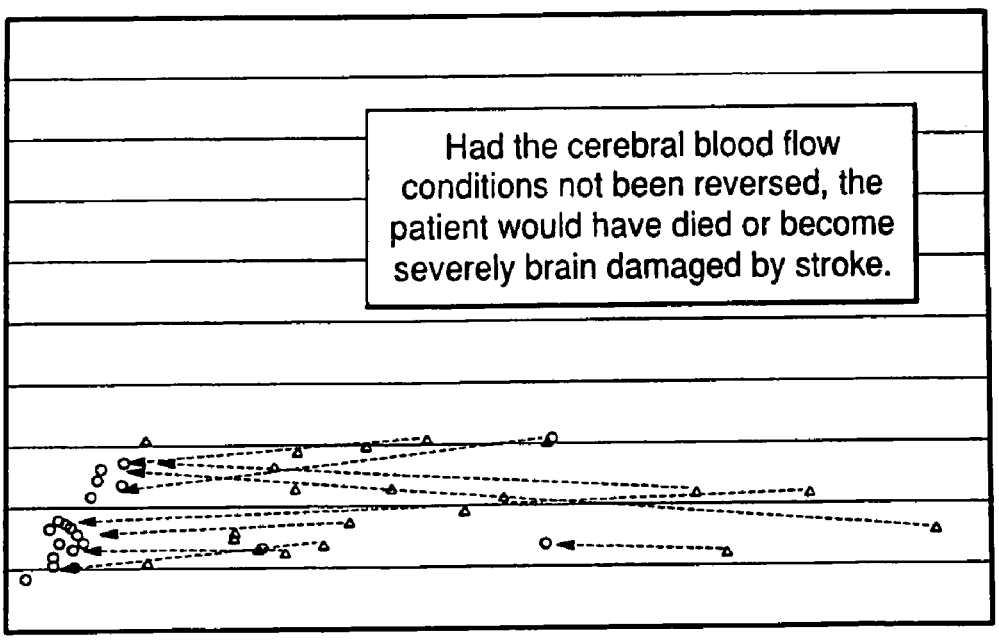
FIG. 28D depicts a return of vascular status to a near normal state after treatment to decrease intracranial pressure.
Figure 29:
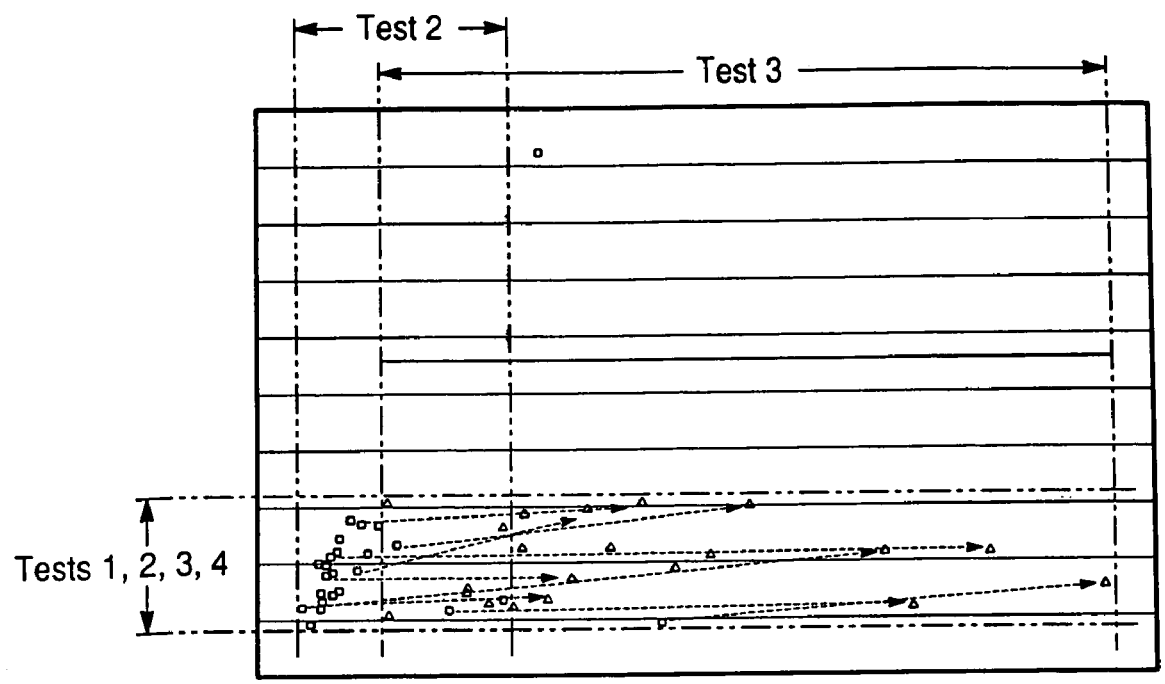
FIG. 29 demonstrates that traditional blood flow tests would not detect the intracranial pressure changes occurring in the subject that were observable using transcranial based dynamic vascular assessment.
Figure 30:
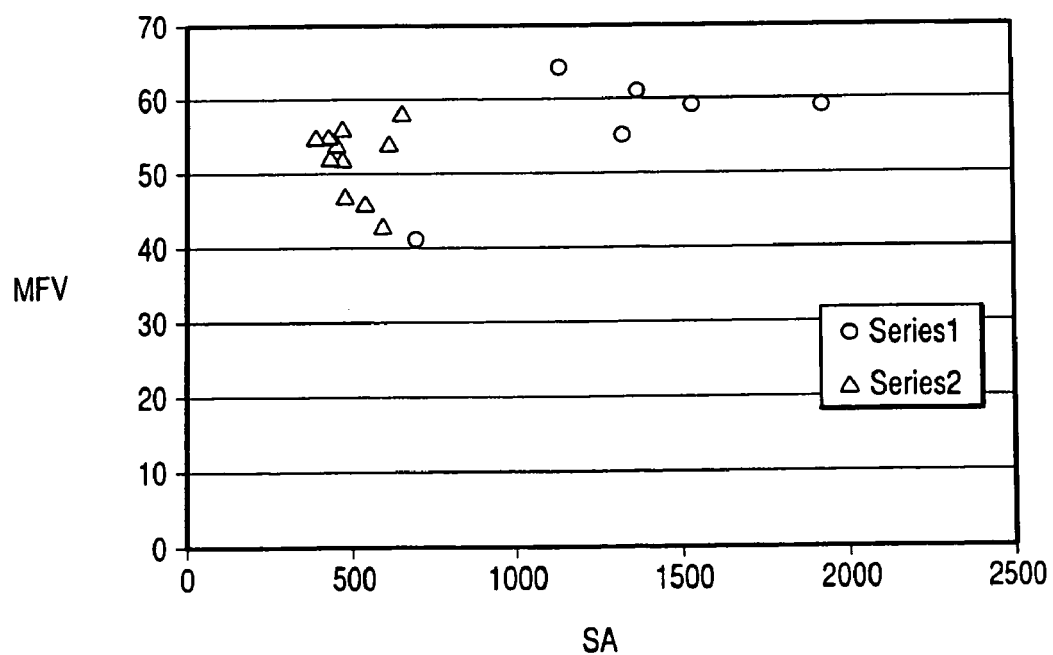
FIG. 30 is a schematic representation of correlated MFV and SA data from the two series of subjects presented in Table 8.
Figure 31:
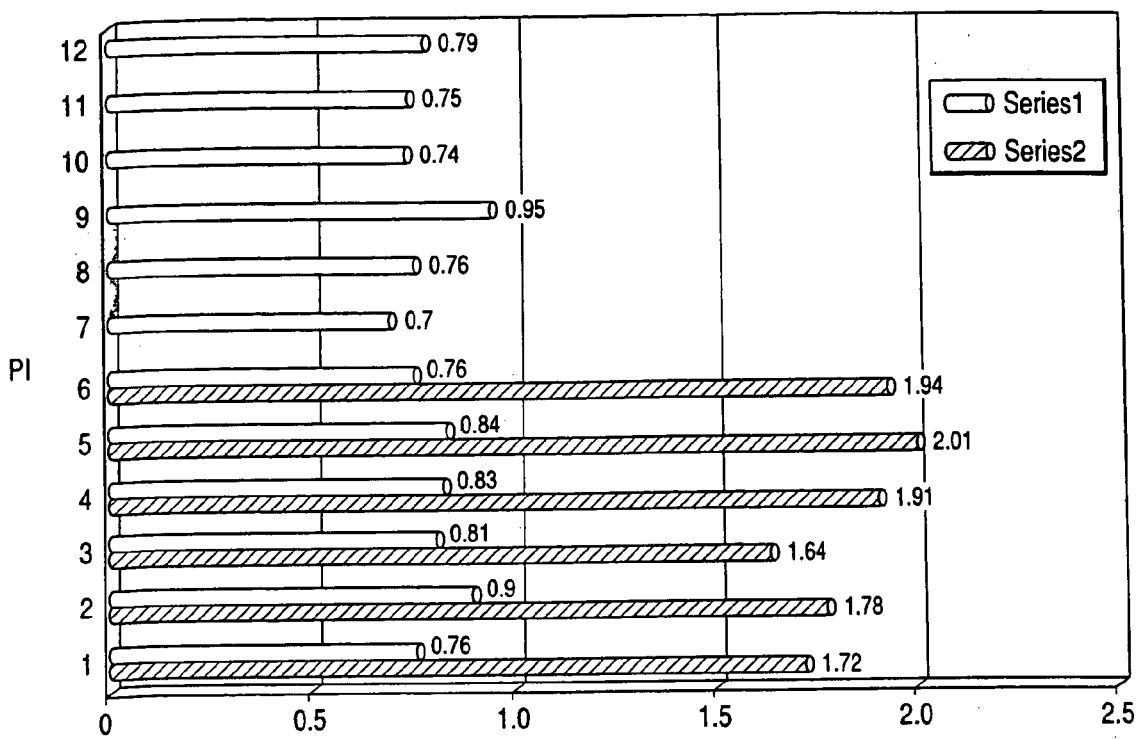
FIG. 31 is a bar graph of Trendelenberg PI data for the two series of subjects from Table 8.
Figure 32:
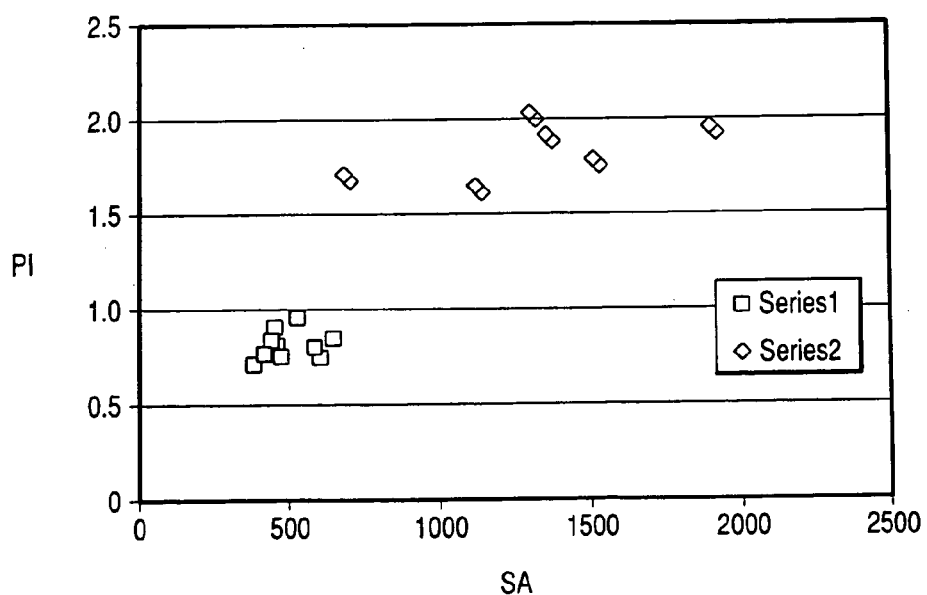
FIG. 32 is a schematic representation of correlated PI and SA data from the two series of subjects presented in Table 8.

The invention is accessed via the Internet through a web site, using a standard browser 2310. FIGS. 24 through 27 illustrate the data available through typical pages displayed at the browser in response to appropriate user actions. The system is entered through a login page, an example of which is illustrated in FIG. 24. In this embodiment, the same login page is used by both users and administrators. Based on the identity of the account, the invention will present either the administrator startup page or the user startup page. The administrator startup page provides an administrator with access to administration functionality described below. The user startup page, illustrated in FIG. 25, lists those patients that are associated with the user. From this point, the user may add new patient data, edit existing patient data or delete patient data.

The patient data page, illustrated in FIG. 26, displays clinical data on a patient and allows a user to edit this data. The patient data page also provides access to the TCD data tab for that patient. The TCD data tab for a patient, provides access to TCD measurements. The user may add new TCD measurements, view existing measurements, edit, or delete measurements. This page provides further access to the hemodynamic analysis tab, illustrated in FIG. 27, for the patient. The hemodynamic analysis tab displays the result of an analysis of a patient's TCD data. If no analysis has been performed on a set of TCD readings, the user may request that such analysis be performed from this page.

The Knowledge base 2362 maintains the knowledge for TCD analysis. The inventions analytical techniques may be modified by changing these Knowledge base 2362 files. The Patient database 2382 stores data about a patient pertinent to analysis of his TCD data. Each patient is assigned a unique ID by the user of the system. Information contained in the Patient database 2382 includes that shown in Table 4.

TABLE 4

| ITEM | DESCRIPTION |
|---|---|
| User ID | Unique identifier for the user of the system |
| Patient ID | Unique identifier for this patient within this user's patients |
| Date of birth | Patient's date of birth |
| Sex | Patient's generic sex |
| Ethnic group | Patient's ethnic group |
| For each set of TCD readings for this patient: | |
| Reading date | Date of reading |
| For each reading within a set of TCD readings | |
| Segment ID | Arterial segment from which the reading was taken |
| Depth | Depth of the reading (mm) |
| PSV | Peak systolic velocity |
| PSVTime | Timestamp of PSV reading (sec) |
| EDV | End diastolic velocity |
| EDVTime | Timestamp of EDV reading (sec) |

The Patient Analysis Database 2384 stores the Reasoning 1020 module's analysis of a set of TCD data. The analysis is stored as a file in a format that can be read into the Reasoning 1020 module, e.g., an extensible Markup Language (XML) file. Information contained in an entry in the Patient Analysis Database 2384 includes the information in Table 5.

TABLE 5

| ITEM | DESCRIPTION |
|---|---|
| User ID | Unique identifier for the user of the system |
| Patient ID | Unique identifier for this patient within this user's patients |
| Reading | Patient's date of birth |
| Analysis | Output file from the patient's concept graph |

The Authorization Database 2342 stores the IDs and passwords of authorized users and administrators. Information contained in an entry in the Authorization Database 2342 includes the information in Table 6.

TABLE 6

| ITEM | DESCRIPTION |
|---|---|
| User ID | Unique identifier for the user of the system |
| Password | Encrypted password for the user |
| Account | User or Administrator |

The Transaction Log 2344 records activity of users and administrators in the system, Information contained in the Transaction Log 2344 includes the types found in Table 7.

TABLE 7

| TRANSACTION NAME | TRANSACTION FIELDS |
|---|---|
| Log in | User ID |
| | Timestamp |
| Failed log in | User ID |
| | Invalid password |
| | Timestamp |
| Log out | User ID |
| | Timestamp |
| Add new patient | User ID |
| | Patient ID |
| | Timestamp |
| Edit patient data | User ID |
| | Patient ID |
| | Timestamp |
| Delete patient | User ID |
| | Patient ID |
| | Timestamp |
| Analyze patient | User ID |
| | Patient ID |
| | Reading ID |
| | Timestamp |
| Display patient list | User ID |
| | Timestamp |
| Display patient | User ID |
| | Patient ID |
| | Timestamp |
| Create new account | Administrator ID |
| | New account ID |
| | Account type (user or administrator) |
| | Timestamp |
| Delete account | Administrator ID |
| | Account ID |
| | Timestamp |
| Download Transaction Log | Administrator ID |
| | Timestamp |
| Download Authorization Database | Administrator ID |
| | Timestamp |
| | Timestamp |

System Database 2390 stores data used to provision the application's process. Examples include parameters for the IPC connections and the location of the data files specified in the above description.

Knowledge structures are defined and developed over the lifecycle of the invention; both for this embodiment and for other preferred embodiments. The knowledge structures identify broad functionality to envision the invention's behavior. Preferred embodiment of the present invention use a concept graph (CNG) for knowledge representation. The CNG, see FIGS. 11 through 22, contain input data to the system and inferred states form the input data. Arrows in the concept graph represent the direction of inference. The inferences culminate in the top-level Stroke Risk concept.

The system provides various functionality to authorized users, including logging in using an existing account; setting up a new patient record; editing an existing patient record; requesting and obtaining an analysis of a previously entered set of patient TCD readings; requesting and obtaining a list of all patients for which that user has entered data, with the existence of an analysis indicated; requesting and obtaining a display of previously entered data and, if available the analysis of that data; deleting patient data entered by that user; deleting a TCD reading set; and logging off.

The system provides various functionality to authorized system administrators, including logging in; creating a new account; listing all existing accounts; deleting an existing account; downloading transaction data; changing the e-mail address to which notifications are sent by the Watchdog 2370; and logging off.

Upon initialization, a main program instantiates and initializes the modules in the following order: Watchdog 2370, System Interface 2320, Accounts Manager 2340, Data Manager 2380, Reasoning Manager 2350. These modules run in separate process spaces from the main program. Upon shutdown, a main program shuts down the modules in the following order: Reasoning 1020 module, Data Manager 2380, Accounts Manager 2340, System Interface 2320, Watchdog 2370.

The System Interface 2320 is initialized by external command. It converts data submitted in hypertext markup language (HTML) into commands for other system modules, and conversely, reformats data from other system modules into outbound HTML pages for presentation to a user. The System Interface 2320 module maintains a list of users currently logged into the system and automatically logs a user off after some time of inactivity. The System Interface 2320 accepts a shutdown command accepts requests for system data from other modules.

The Data Manager 2380 can be initialized by an external command, and maintains data in persistent storage. The Data Manager 2380 is able to accept and respond to various commands, such as retrieve the IDs of patients entered by a particular user; set up a new patient record; retrieve a patient's data; modify a patient's data; store the analysis of a particular TCDV reading; retrieve the analysis of a particular TCDV reading; delete a patient's records; and shut down.

The Accounts Manager 2340 can be initialized by external command, and can accept transactions to be recorded in a Transaction Log 2344. The Accounts Manager 2340 can accept and respond to commands such as create a new account; delete an existing account; validate an account ID and password (if the account ID and password are valid, the Accounts Manager 2340 can indicate in the reply whether this account is a regular user or an administrator); download the Transaction Log 2344; download the Authorization Database 2342; and shut down.

The Reasoning Manager 2350 can be initialized by an external command. Upon initialization, the Reasoning Manager 2350 initializes one instance of the Reasoning 1020 module. The Reasoning Manager 2350 maintains connections to all existing instances of the Reasoning 1020 module. The Reasoning 1020 modules run in a separate process space from the Reasoning Manager 2350. The Reasoning Manager 2350 initialize additional instances of the Reasoning 1020 module or delete instances of the Reasoning 1020 module as necessary to optimize the system load.

The Reasoning Manager 2350 is able to accept and respond to various commands such as analyze a patient's data. The patient's data is assumed to be accessible through the Data Manager. The Reasoning Manager 2350 retrieves the data from the Data Manager, loads it into a particular Reasoning 1020 module, and issues a command to the Reasoning 1020 module to analyze the data. The Reasoning Manager 2350 is further able to accept and respond to other various commands such as query a patient's analysis for a particular concept instance. In this instance, the Reasoning Manager 2350 loads the analysis into a Reasoning 1020 module, if necessary, and sends a query to the Reasoning 1020 module. The Reasoning Manager 2350 is further able to accept and respond to other various commands such as query a patient's analysis for all instances of a particular concept pattern. In this instance, the Reasoning Manager 2350 loads the analysis into a Reasoning 1020 module, if necessary, and sends a query to the Reasoning 1020 module. The Reasoning Manager 2350 is further able to accept and respond to other various commands such as query a patient's analysis for further explanation of a concept instance. If necessary, the Reasoning Manager 2350 loads the analysis into a Reasoning 1020 module and sends a query to the Reasoning 1020 module. The Reasoning Manager 2350 is further able to accept and respond to other various commands such as shut down. When shutting down, the Reasoning Manager 2350 preferably shuts down all instances of the Reasoning 1020 module.

Reasoning 1020 module is initialized by an external command. No other commands are processed until the module is initialized. The Reasoning 1020 module Applied System Intelligence, Inc.'s PreAct DSA 1022 module to store and analyze data using a concept graph. The Reasoning 1020 module uses a knowledge bases independent of the PreAct library to store the concept patterns and necessary algorithms. These knowledge base 2362$s$ are loaded after the module is initialized. The algorithms use various reasoning techniques, e.g., Bayesian reasoning, to propagate belief values through the graph. Sample concept graphs can be found at FIGS. 11 through 22. The Reasoning Module 2360 provides accessors to input patient data into the concept graph.

The Reasoning Module 2360 accepts and responds to various commands such as clear the current concept graph; analyze a patient's data (preferably, the module sends a notification when the analysis is complete); save the analysis of the current patient's data (preferably, the module sends a notification when the save is complete); load a saved patient analysis; and stop.

The Reasoning 1020 module can accept and respond to one or more queries for all instances of a particular concept pattern in the concept graph; a particular concept instance; and further explanation of a concept instance. The Reasoning 1020 module is further able to write non-fatal errors to a log file.

The Watchdog 2370 includes an off-the-shelf module chosen to be initialized by an external command which will set all necessary parameters; to send a notification to a specified set of e-mail addresses when the available disk space drops below a preset level; to send a notification to a specified set of e-mail addresses when the system load exceeds a preset level; and to accept and respond to a command to change the set of e-mail addresses to which notifications are sent.

An exemplary network architecture of an exemplary system in accordance with the present invention is described below. The exemplary system comprises one or more client stations, a central server and a communications link. The one or more client stations function as remote access points to the central server. A client station may be located in a laboratory, a physician office and/or at any other appropriate site. A client station may be configured for transmitting and/or receiving information to or from the central server in either an interactive mode or a batch mode.

Client stations may comprise any type of computer-like device that is capable of sending and/or receiving data. For example, a client station may comprise a desktop computer, a laptop computer, a hand-held device, or the like. A client station may also comprise a laboratory instrument having functionality for collecting raw data (such as patient vascular data), and for transferring that raw data to the central server via the communications link. A client station may also comprise a device for receiving raw data from a laboratory instrument, such as a flow analytical device, or a device holding data transmitted from a flow analytical device, and then passing that data to the central server via the communications link. These and other examples of client station configurations will be apparent to those of ordinary skill in the art.

A first client station may be configured to transmit raw data to the central server via the communications link and a second client station may be configured to receive processed data (results) from the central server via the communications link. A client station may implement various user interfaces, printing and/or other data management tasks and may have the ability to store data at least temporarily.

The communications link may comprise a dedicated communications link, such as a dedicated leased line or a modem dial up connection. Alternately, the communications link may comprise a network, such as a computer network, a telecommunications network, a cable network, a satellite network, or the like, or any combination thereof. The communications link may thus comprise a distributed network and/or one or more interconnected networks. In an exemplary embodiment, the communications link may comprise the Internet. As should be apparent to those of skill in the art, the communications link may be land-line based and/or wireless. Communications over the communication link between the client station and the central server may be carried out using any well-known method for data transmission, such as e-mail, facsimile, FTP, HTTP, and any other data transmission protocol.

The central server comprises the computer-based database of vascular information. The central server implements analytic and interpretive algorithms. It will be apparent to those of skill in the art, however, that the communication station and the computation station may be implemented in a single computer. The configuration of an exemplary central server will be described in greater detail below.

A system in accordance with an exemplary embodiment of the present invention may operate in an interactive mode or a batch mode. In the interactive operating mode, data samples are processed one by one interactively. For example, in an interactive processing mode, a user connects to the central server through a client station. A data sample to be processed is then sent from the client station to the central server. The processed data (result file) is returned from the central server to the client station, where it may be printed and/or archived. After the result file is received at the client station, a subsequent data sample may then be transmitted from the client station to the central server.

An exemplary system configured for an interactive processing mode is now described. A client station may be configured for execution of a communication browser program module and one or more printing and/or archiving program modules. As is known in the art, a convenient and effective communication link for facilitating interactive operations is the Internet. Communication browsers are also known as World Wide Web browsers or Internet browsers.

The components of the central server may be distributed among two stations, a communications station and a computation station. Configured for an interactive processing mode, the communications station may comprise a communications server, such as a standard http server, for interacting with the communication browser executed at the client station. Communications between the communications server and the communication browser may occur using html pages and computer graphics interface (CGI) programs transferred by way of TCP/IP.

Substances

In one preferred embodiment of the present invention, vascular reactivity to substances may be evaluated. Substances include, but are not limited to, alcohol, nicotine, foodstuffs, extracts of plants, nutraceuticals, and drugs. Many drugs are known to have effects on the vascular system. A non-limiting list of classes of drugs and drugs known to have affects on the vascular system includes the following: beta adrenoreceptor antagonists; calcium channel antagonists; angiotensin I converting enzyme inhibitors; alpha adrenoreceptor antagonists; cholesterol antagonists; angiotensin II 1 antagonists; HMGCoA reductase inhibitors; thrombin inhibitors; adrenoreceptor antagonists; endothelin A receptor antagonists; NMDA antagonists; platelet aggregation antagonists; NMDA antagonists; platelet aggregation antagonists; sodium channel antagonists; 5-hydroxytrypltamine 1a agonists; AMPA receptor antagonists; GPIIb IIIa receptor antagonists; lipase clearing factor stimulants; potassium channel agonists; potassium channel antagonists; 5-alpha reductase inhibitors; acetylcholine agonists; dopaminergic agonists; endopeptidase inhibitors; estrogen antagonists; GABA receptor agonists; glutamate antagonists; peroxisome proliferator-activated receptor agonists; plasminogen activator stimulants; platelet-derived growth factor receptor kinase inhibitors; prostacyclin agonists; sodium/hydrogen exchange inhibitors; vasopressin 1 antagonists; 15-lipoxygenase inhibitors; acetyl CoA transferase inhibitors; adenosine A1 receptor agonists; aldose reductase inhibitors; aldosterone antagonists; angiogenesis stimulants; apoptosis antagonists; atrial peptide antagonist; beta tubulin antagonists; bone formation stimulants caspase inhibitors; CC chemokine receptor 2 antagonists; CD 18 antagonists; cholesterol ester transfer protein antagonists; complement factor inhibitors; cyclooxygenase inhibitors; diuretics; DNA topoisomerase ATP hydrolyzing inhibitors; elastase inhibitors; endothelial growth factor agonists; enkephalinase inhibitors; excitatory amino acid antagonists; factor Xa inhibitors; fibrinogen antagonists; free radical scavengers; glycosylation antagonists; growth factor agonists; guanylate cyclase stimulants; imidazoline I1 receptor agonists; immunostimulants; immunosuppressants; interleukin 1-beta converting enzyme inhibitors; interleukin 8 antagonists; LDL receptor function stimulants; MCP-1 antagonists; melanocortin MC-4 antagonists; mineralocorticoid antagonists; nerve growth factor agonists; neuropeptide Y antagonists; oxygen scavengers; phosphodiesterase inhibitors; potassium sparing diuretics; proline hydroxylase inhibitors; prostaglandin E1 agonists; purinoreceptor P2T antagonists; reducing agents; thromboxane A2 antagonists; thyroid hormone function agonists; transcription factor inhibitors; vasopressin 2 antagonists; and vitronectin antagonists, among others.

In addition, other agents are suspected of having vascular activity. These agents are include, but are not limited to, danaparoid sodium, nitric acid scavengers, clomethiazole, remacemide, TP10, cerivastatin, nimodipine, nitrendipine, BMS-204352, BIII-890, dipyridamole+ASA, fradafiban, irampanel hydrochloride, lefradafiban, aptiganel, sipatrigine, NRTs, cromfiban, eptifibatide, nematode anticoagulant protein NAPc2, UK-279276, Flocor, DMP-647, ASA, GPI-6150, dermatan sulfate, NOS inhibitors, ancrod, PARP inhibitors, tinzaparin sodium, NOX-100, LDP-01, argatroban, fosphenyloin, tirilazad mesylate, dexanabinol, CPC-211, CPC-111, bosentan, clopidogrel hydrogen sulfate, nadroparin, ticlopidine, NS-1209, ADNF III, vinconate, ONO-2506, cilostazol, SUN-N4057, SR-67029i, nicardipine, YM-337, and YM-872.

The present invention may be utilized following administration of the drug through acceptable methods of administration to evaluate the effects on vessels. It is to be understood that the present invention may be practiced with regard to different vessels, including but not limited to, vessels in the extremities, in the coronary circulation, and extracranial and intracranial cerebral vessels. In a preferred embodiment, the extracranial and intracranial cerebral vessels are examined with the present invention.

Measurements may be taken before administration of the drug, and at specific times following administration of the drug to determine the effect of the drug on vascular reactivity. In this manner, each individual subject and each individual vessel acts as its own control to assess the effects of that drug on that specific vessel.

All cerebral vessels may be analyzed to determine whether the drug has differential effects on different cerebral vessels. By performing such an analysis over numerous individuals, valuable data may be obtained concerning the vascular effects of a specific drug. Furthermore, by choosing individuals from different groups, such as (a) individuals with no known pathology, (b) individuals with no known pathology in specific age groups, (c) individuals with known pathology in a specific disease group, (d) individuals with known pathology in a specific disease group in a specific age range or in a specific stage of the progression of the disease, and (e) individuals in a specific disease group currently receiving specific therapeutic mediations.

Through application of the present invention to individuals from the desired group, valuable information may be obtained concerning the effects of different disease processes, or prior or co-administration of other drugs, on the vascular effects of the test drug in different individuals, at different ages, and in different conditions.

It will be appreciated that a preferred embodiment of the present invention allows for the assaying of the efficacy of a treatment comprising collecting data regarding cerebrovascular health status of a number of individuals serving as patients in the clinical trial; grouping the patients into at least two groups of patients such that patients with a similar cerebrovascular health status are grouped together; applying the treatment to the at least two groups of patients; monitoring outcomes of the treatment for each of the at least two groups of patients; and determining the efficacy of the treatment based on the outcomes of the treatment for each of the at least two groups of patients. In a preferred embodiment of the present invention, the data regarding cerebrovascular health status comprises mean flow velocity value for at least three cerebrovascular vessels of the individuals and systolic acceleration value for at least three cerebrovascular vessel s of the individuals. In another preferred embodiment of the invention, the data regarding cerebrovascular health status further comprises calculating a pulsatility index.

Another preferred embodiment of the present invention provides a method of screening for adverse effects of a treatment comprising: applying the treatment to a number of individuals; monitoring the cerebrovascular blood flow of such individuals after applying the treatment; and identifying adverse effects to cerebrovascular blood flow in such individuals arising after applying the treatment. In a preferred embodiment, quantitative data regarding the cerebrovascular blood flow of a number of individuals is obtained. In a still further preferred embodiment of the present invention, the data regarding cerebrovascular health status comprises mean flow velocity value for at least three cerebrovascular vessels of the individuals and systolic acceleration value for at least three cerebrovascular vessels of the individuals. In still a further preferred embodiment, the data regarding cerebrovascular health status further comprises calculating a pulsatility index.

It will be appreciated that the present invention allows for the creation of matched groups with a suite of blood vessel issues, e.g., plaque and general vasculitis, among others. The present invention also provides for the creation of matched groups with a particular circulatory problem, e.g., stenosis in a particular vessel, inadequate profusion of small blood vessels in posterior of brain, migraines, and apnea, among others.

Under conventional approaches to clinical trials, one cannot identify participants with such problems, much less match participants wherein both groups have essentially the same severity and incidence of the pathology being examined. Thus, the conventional approach to clinical trials (1) address much less specific conditions, e.g., overall stroke risk, rather than the precise severity and incidence of the pathology being examined, (2) include individuals who show no disease/deterioration, and (3) include individuals who are likely to suffer immediate catastrophic failure. Despite numerous attempts to conduct clinical trials related to primary stroke prevention where there is no previous history of stroke or acute cardiac event, this problem has remained unsolved until now.

EXAMPLE 1

Effects of Propranolol on Vascular Reactivity

Propranolol, also known as Inderal, is prescribed routinely for individuals with hypertension, one of the major risk factors for stroke. In order to assess the effects of propranolol on vascular reactivity, a transcranial Doppler analysis was performed on the cerebral vessels of a 46 year old hypertensive man. Propranolol was then administered at an oral dosage of about 40 mg. Another transcranial Doppler analysis was performed approximately two hours after administration of the propranolol. Changes in specific vessels were compared to pre-administration readings. By analyzing pre- and post-administration vessel dynamics, an indication of the effect of the beta adrenergic blocker, propranolol, on dynamics of flow in specific cerebral vessels is obtained.

EXAMPLE 2

Analysis of the Effects of Plavix on Cerebral Vessels

Plavix is a member of a class of drugs known as blood thinners or anti-platelet drugs. Plavix is often prescribed following stroke to minimize platelet aggregation and clot formation. However, one of the major dangers of Plavix is intracranial hemorrhage. Therefore, when using Plavix to prevent or minimize the possibility of a stroke due to infarction, one may increase the possibility of a hemorrhagic stroke. Accordingly, properly selecting the appropriate patient for Plavix is critical for maintenance of vascular health.

A 63 year old male with a history of hypertension experiences a first stroke in the left middle cerebral artery resulting in deficits in the right hand, leg, and some deficits in motor speech. These are the symptoms upon presentation in the neurological clinic. Transcranial Doppler analysis of all cerebral vessels is performed in addition to analyzing the common carotid artery and the internal carotid artery. The analysis reveals alterations in vascular flow in the internal carotid artery just distal to the bifurcation of the common carotid artery. A stenotic area is observed. Further, additional flow abnormalities are detected in the left middle cerebral artery, consistent with the patient's presentation of right-sided motor paralysis. Transcranial Doppler analysis reveals excellent collateral flow to the contralateral hemisphere and no deficits in the left anterior cerebral and left posterior cerebral arteries.

The physician considers prescription of Plavix together with a calcium channel blocker. Transcranial Doppler analysis was performed at monthly intervals. By analyzing changes in the individual cerebral vessels as a function of Plavix +/− calcium channel blocker administration, the physician observes no effect on the cerebral vessels. The physician subsequently administers a higher dose. Again, transcranial Doppler analysis is performed on all cerebral vessels. The physician observes marked changes in the vascular dynamics of the vessel studied as the pulsatility index decreases and the auto-regulation curve left-shifts toward normal. The physician, based on these results, determined a proper dosage of the vasoactive medication for the patient.

The patient is then monitored on a monthly basis after the initial prescription of Plavix in order to determine whether vascular changes are occurring which necessitate alteration in the therapy.

EXAMPLE 3

Assessment of Cerebral Vascular Status During Battlefield Situations

A 21 year old paratrooper jumps from an airplane to reach the battlefield below. While parachuting to the surface, his parachute becomes entangled in the branches of a large tree. The serviceman hears gunfire in the vicinity of his location and, in an attempt to free himself, cuts one of the lines connecting the parachute to his harness. He falls to the earth but his head strikes a major branch of the tree during descent. The serviceman is found unconscious by a field medic. After determining that no cervical fracture is present, the medic removes the serviceman to a field hospital. Transcranial Doppler is performed by the medic trained in such techniques. The data is acquired and transmitted by an uplink satellite communication to a battlefield command center hospital. Prior data on the serviceman is compiled during routine physical examination at the time of induction into the service. The new transcranial Doppler data is compared to the prior data. The results indicate dramatic changes in auto-regulation of the left anterior cerebral artery. This is caused by vasospasm due to a subarachnoid hemorrhage from blunt force trauma at the fronto-parietal suture. There is also a subdural hematoma. The field physician suspects this possibility in view of the contusions evident in the region of this suture. The results of the comparative analysis of the cerebral vessels are transmitted to the field physician who then performs an emergency craniotomy in the region of the left fronto-parietal suture. Following release of pressure on the brain and stabilization of the patient, a transcranial Doppler analysis is performed immediately post surgery, and at 12 and 24 hours thereafter. The results indicate that the left anterior cerebral artery flow dynamics are changing and the characteristic of this vessel moves from the lower right quadrant on the plot of flow velocity versus systolic acceleration toward the region of normal auto-regulation.

Another scenario is development of spasm or post-traumatic hyperemia at 24° C. with clinical deterioration. Transcranial Doppler analysis was performed at the field hospital. Worsening vasospasm was found and the treatment altered in response.

EXAMPLE 4

Application of Transcranial Doppler Analysis in the Emergency Room

A 23 year old is admitted into the emergency room in a state of extreme agitation and mania. While the medical staff is attempting to obtain a blood workup and waits for the results of the analysis, the patient suddenly falls unconscious. Blood pressure is observed to drop precipitously. Transcranial Doppler analysis is performed on the cerebral vessels of the patient. The results indicate a shifting to the lower left of the normal regulation curve for the left middle cerebral artery. Electrocardiagraphic analysis reveals atrial fibrillation. Blood chemistry reveals that the patient took a large dosage of cocaine together with amphetamine. The results of the transcranial Doppler analysis are consistent with induction of cerebral vascular failure which was secondary to a heart attack due to extreme vessel constriction of the coronary vasculature.

EXAMPLE 5

Case Study of a Female Who Presented With Unsteady Gait

Figure 9A:
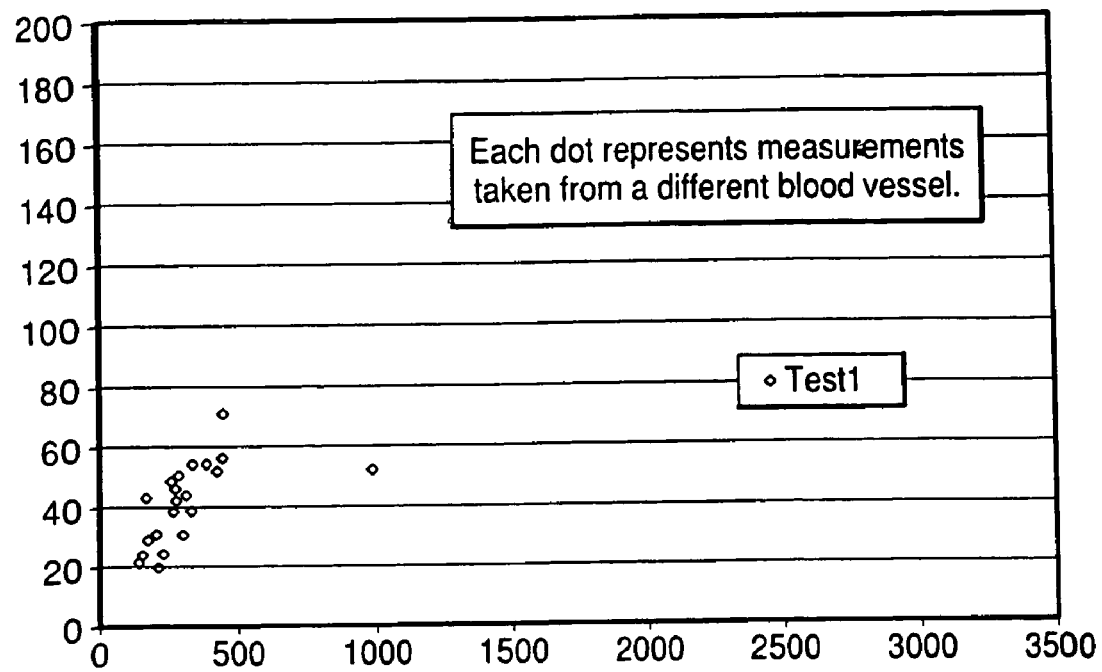
FIGS. 9a to 9d show schematic representations of a 2-dimensional nomogram in which mean flow velocity is indicated on the y-axis and systolic acceleration is provided on the x-axis of a patient who presented with slight feelings of unsteadiness.
Figure 9B:
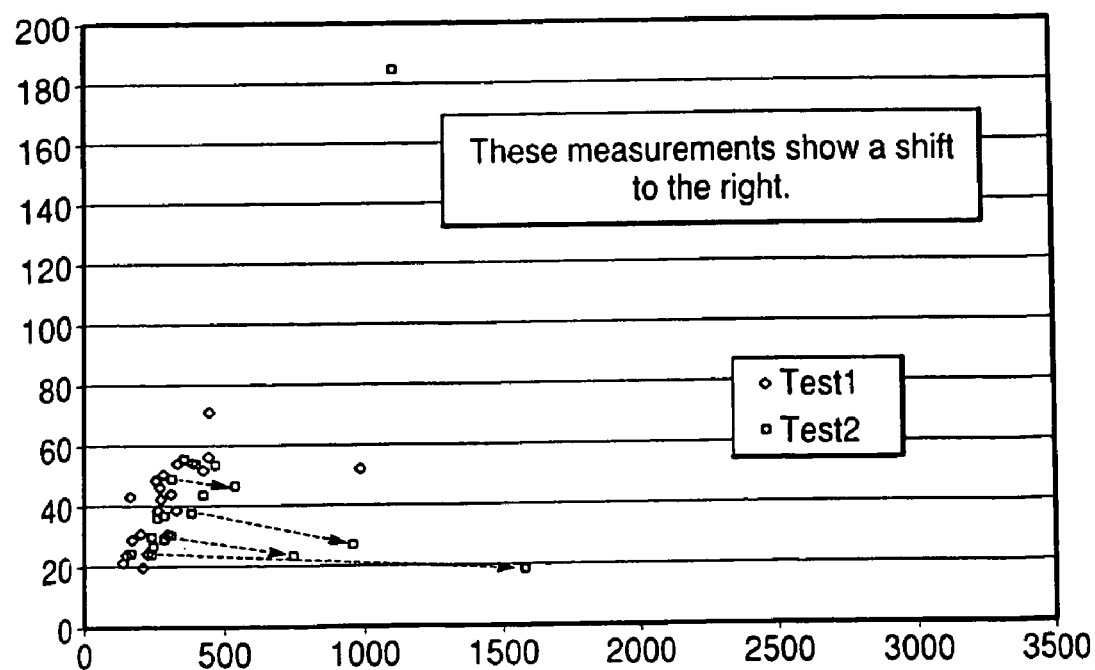

A 62 year old female presented in the neurological clinic complaining of slight feelings of unsteadiness during walking. Transcranial Doppler analysis was performed and the different cerebral vessels were analyzed. The initial nomogram schematic representation of a 2-dimensional nomogram of the transcranial Doppler sonography data, in which mean flow velocity is indicated on the y-axis and systolic acceleration is provided on the x-axis, is provided in FIG. 9a. Shortly thereafter, the patient's symptoms worsened, however, no definitive diagnosis was yet established. Transcranial Doppler analysis was performed a second time and the transcranial Doppler sonography data was represented in a second nomogram provided in FIG. 9b. The results were compared to the first test and showed a clear shifting to the right on the flow velocity versus systolic acceleration plot.

Figure 9C:
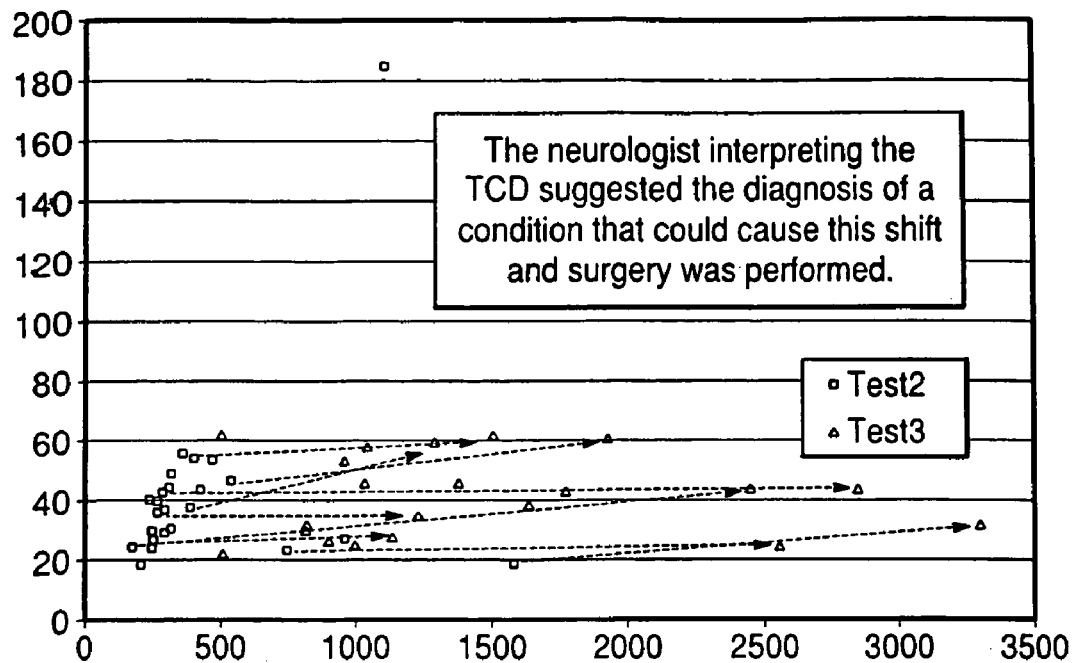
Figure 9D:
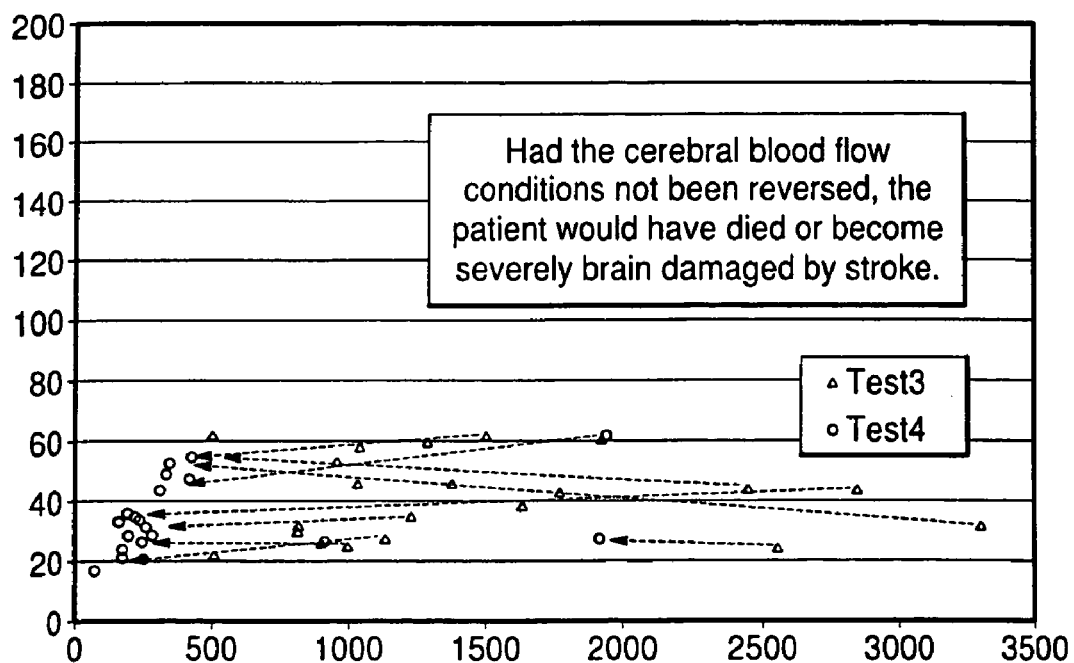

Next, the patient was hospitalized in critical condition and yet no diagnosis had been established. The technician performed another transcranial Doppler test and the transcranial Doppler sonography data was represented in a third nomogram provided in FIG. 9c. A dramatic shifting to the right of many of the vascular points was observed. A cisternogram revealed hydrocephalus, so a shunt was inserted. The neurologist concluded that an increased intracranial pressure had exerted a deleterious effect on the cerebral vessels displacing them from the normal auto-regulation zone. Following surgery, a fourth transcranial Doppler analysis was performed and the transcranial Doppler sonography data was represented in a fourth nomogram provided in FIG. 9d. The results showed a clear return toward baseline, i.e., a left shifting in the characteristic data points for the vessels analyzed toward their prior location at the time of the second test.

This example demonstrated that the results from the transcranial Doppler analysis, a non-invasive and highly accurate test, provided valuable information for the neurologist to select an appropriate course of action thereby probably preventing a massive increase in intracranial pressure resulting in an occlusive stroke and probable death. These results also provided an indication of the onset of the life-threatening changes that occurred between tests 2 and 3.

EXAMPLE 6

Use of Transcranial Doppler to Analyze Blunt Force Trauma in an Athlete

During a soccer match, a 17 year old high school student receives a severe blow to the forehead when he and an opponent jumped together to head the ball. The student becomes unconscious but is then revived with smelling salts. After the game, he complains of changes in his vision. He is taken to the emergency room and a transcranial Doppler analysis is performed. The results of the analysis are compared to a transcranial Doppler analysis performed at the beginning of the soccer season. Transcranial Doppler analysis shows a slight change in the flow dynamics of the left posterior cerebral artery indicating hyperemia or increased flow often observed in patients with cerebral contusions. Twenty-four hours later the patient's mental state deteriorates and a CT scan only reveals subarachnoid blood. A repeat transcranial Doppler analysis shows vasospasm of the same artery. An interventional neuroradiologist is called into the case and performs angioplasty. Following the procedure, transcranial Doppler analysis is performed periodically over a 6 week period. The results are compared to the transcranial Doppler profile at the time of admission to the emergency room and also to the normal readings obtained at the beginning of the soccer season. The results show a gradual return to the normal flow patterns for the left posterior cerebral vessel.

EXAMPLE 7

Use of Transcranial Doppler to Analyze Blunt Force Trauma in the Vascular Effects of a Drug A pharmaceutical company has developed a new substance which it suspects may have antihypertensive activity by inducing partial dilation of blood vessels. The company selects a patient population of individuals with normal blood pressure, a population with mild hypertension, and a population with severe hypertension. Sub-populations are constructed based on age (fourth, fifth and six decades of life) and sex.

The cerebral vessels of all patients are analyzed using transcranial Doppler analysis, as described in the present invention, two hours before and two hours following oral administration of 25 mg of the test substance. Blood pressure was monitored at 30 minute intervals for the two hours before and two hours following oral administration of the new substance. The results demonstrate no discernable effect in the normotensive and mildly hypertensive group, and a significant anti-hypertensive effect in the severely hypertensive patients in all age groups tested. Analysis of the data obtained with transcranial Doppler revealed a decreased flow velocity in the vessels of the great arterial circle.

Significant variation is detected in the data set from the female test groups in the fifth and sixth decades of life. Further questioning of these individuals revealed use of anti-menopausal hormone replacement therapy through combined administration of estrogen and progesterone. Removal of data contributed from these individuals dramatically decreases variance in these test groups. The pharmaceutical company initiates a new study to examine the potential interactions of the test substance with estrogen, progesterone, or a combination of estrogen, and progesterone, in normotensive, mildly hypertensive, and severely hypertensive females in premenopausal and postmenopausal groups, further subdivided by history of hormone replacement therapy or exposure to oral contraceptives.

The invention disclosed above is also applicable as both a system and method for monitoring and improving the design, performance, marketing and use of vascular stents. Stents are devices that are adapted to be implanted into a patient's body lumen, such as a blood vessel, to maintain the patency thereof. In particular, these devices are very useful in the treatment of atherosclerotic stenosis in blood vessels. Stents are generally tubular-shaped devices which function to hold open a segment of a blood vessel or other anatomical lumen. They are particularly suitable for supporting and holding back a dissected arterial lining which can occlude the fluid passageway therethrough.

Stent properties can be broadly characterized in two ways. Stents can be categorized according to their physical properties. Such physical properties include, as described above, the ability of certain stents to hold open or further open a narrowed stenotic segment of a blood vessel.

Alternatively, stents can be classified according to their chemical properties. Such stents may be used as physical repositories for chemicals (e.g., special coatings or drugs), wherein the chemicals may be impregnated in the physical material of the stent such that they are released at an appropriate time or rate to achieve certain medical effects within the vascular system. Such chemicals may have global and/or local effects within the vascular system. For example, a stent could be deployed at a site of vasculopathy to provide a local transudation of chemical to diseased endothelium. Simultaneous with its use as a chemical repository, a stent may also gradually and continuously exert pressure radially (i.e., outward) from within the lumen of a vessel segment, thus achieving the same result achieved by forced balloon angioplasty. Consequently, the results may include a gradual reduction of stenosis and/or the resorption/remodeling of plaque by, among other mechanisms, either the dissolution and absorbtion of calcium contained within plaque or through the break down of cholesterol esters that may be present.

Among the types of chemicals that can be used with and/or delivered via stents are: (a) agents that reduce platelet aggregation (e.g., Aspirin or Plavix); (b) agents that reduce local inflammation (e.g., Persantine, statins, or Cox 2 inhibitors); (c) agents that reduce local calcium accumulations (e.g., chelators like EDTA); (d) agents that reduce local cholesterol depositions (e.g., statins or certain enzymes, like a cholesterol esterase, that actually will elude cholesterol from the site of the vascular lesion); (e) agents that cause local vasodilation and reduce the spasm-induced by placement of a statin (e.g., Paclitaxel, Sirolimus, Persantine, statins, Papaverine, nitric oxide, or Nitric Oxide synthetase-ENOS or INOS).

A stent may be made of material that is capable of being completely reabsorbed (much like an absorbable suture (i.e., once the medicinal and/or mechanical effects are complete, the stent material gradually dissolves). In the unlikely event a dissolving stent fragments, any such fragment would also readily be dissolved and reabsorbed.

The use of Dynamic Vascular Analysis (DVA) (formerly described as DCA or Dynamic Cerebrovascular Analysis) methodology described above has been uniquely applied for the monitoring and improvement of the design, performance, marketing and use of vascular stents. DVA is particularly applicable to evaluating stents because it enables the real time monitoring of the dynamic components of blood flow (within a single pulse or multiple pulses) to ascertain the physical properties and performance of the vasculature prior to, and in response to, stent placement. These measurements can be made in areas of the vasculature that are both proximate and distal to the location of a stent. Importantly, DVA-assisted stenting considers the global effects of stent implantation, which is a distinct improvement over traditional stenting and stroke risk monitoring methodologies that only considered a discreet, cross sectional view of the flow effects at the point of (or in close proximity to) a carotid blockage. DVA-assisted stenting measures all of the areas of the intracranial vasculature, as well as the arteries supplying those areas, to determine the flow effects before, during and after a stenting procedure. DVA further enables new uses and optimized placement of stents (including monitoring extraneous events associated with stent placement such as emboli occurrence, etc.), new indications for existing stents, new designs for future stents (including new ways of marketing/specializing stents), among other things.

As described above, DVA involves the analysis of the Transcranial Doppler data (TCD). As applied to stenting, DVA can include TCD and/or Intravascular Ultrasound data (collectively "ultrasound data") that is collected and evaluated (via software) as a function of time and velocity. Among the factors that can be measured and considered when evaluating stenting efficacy and procedures are (a) a simultaneous consideration of the ultrasound data values (peak systolic velocity (PSV), end diastolic velocity (EDV), peak systolic time (PST), end diastolic time (EDT), mean flow velocity (MFV), systolic acceleration (SA), pulsatility index (PI), the natural logarithm of the SA (LnSA)) for each of the established 19 vessel segments within the cerebral vasculature; (b) a comparison of the ultrasound data values against a reference database to quantify the degree of variance from mean values; and (c) a series of indices (blood flow velocity ratios) derived from the ultrasound data values that are representative of the vascular status/performance/health of each the 19 vessel segments.

The derived indices include:
1. Dynamic Work Index (DWI or Acceleration/Mean Flow Velocity Index (VAI))=(the natural logarithm of the Systolic Acceleration value divided by the Mean Flow Velocity value and/or reciprocals thereof). Thus, the DWI relates to the force of flow to the mean flow velocity and describes kinetic efficiency of a segment in moving blood forward.
2. Dynamic Flow Index (DFI or Velocity/Impedance Index (VPI))=(Mean Flow Velocity value divided by the Pulsatility Index value and/or reciprocals thereof). Thus, the DFI relates the mean flow velocity to the impedance (pulsatility index) and describes how capacitance volume affects flow through the conductance vessel; and
3. Dynamic Pressure Index (DPI or Acceleration/Impedance Index (API))=(the natural logarithm of the Systolic Acceleration value divided by the Pulsatility Index value and/or reciprocals thereof). Thus, the DPI relates the force of flow to impedance and describes the effect of capacitance vessel volume on the force of flow.

Figure 33:
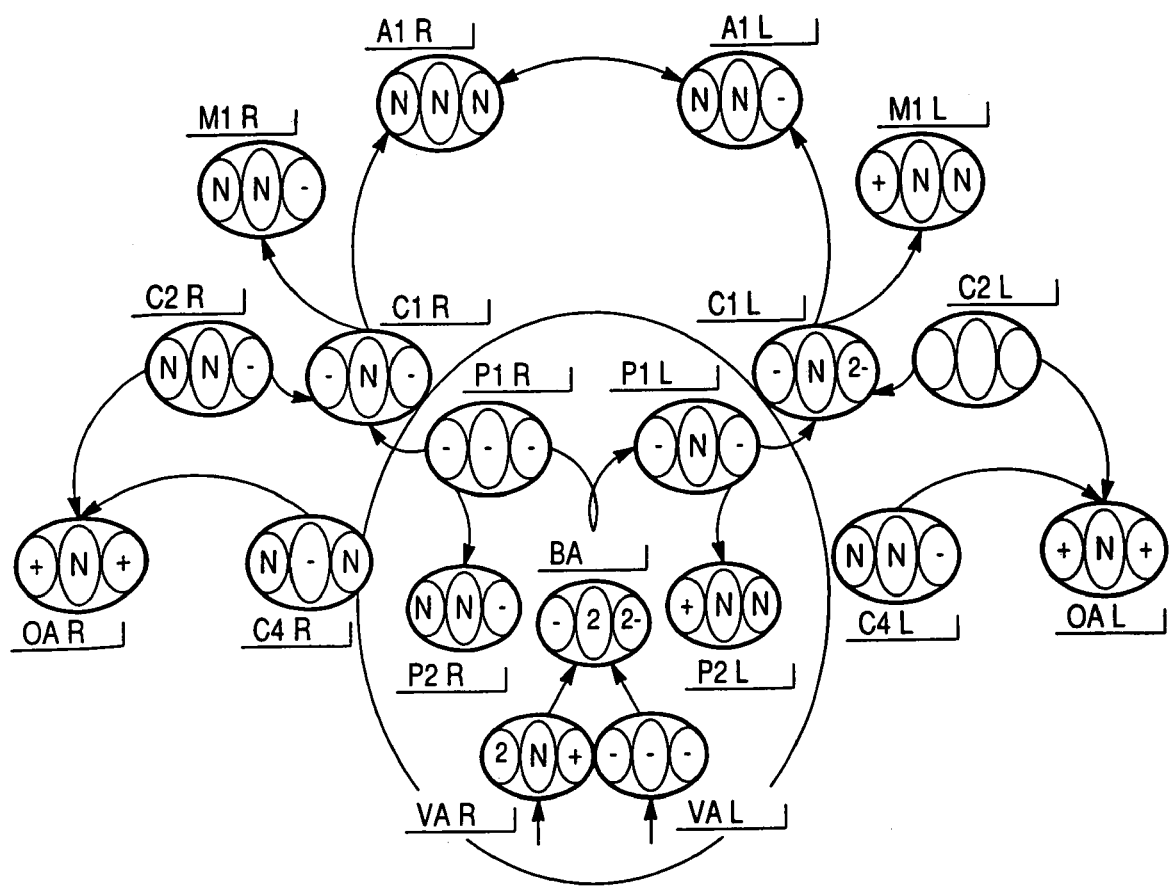
FIGS. 33 and 34 depict 19 intracranial vessel segments available for evaluation by the invention.
Figure 34:
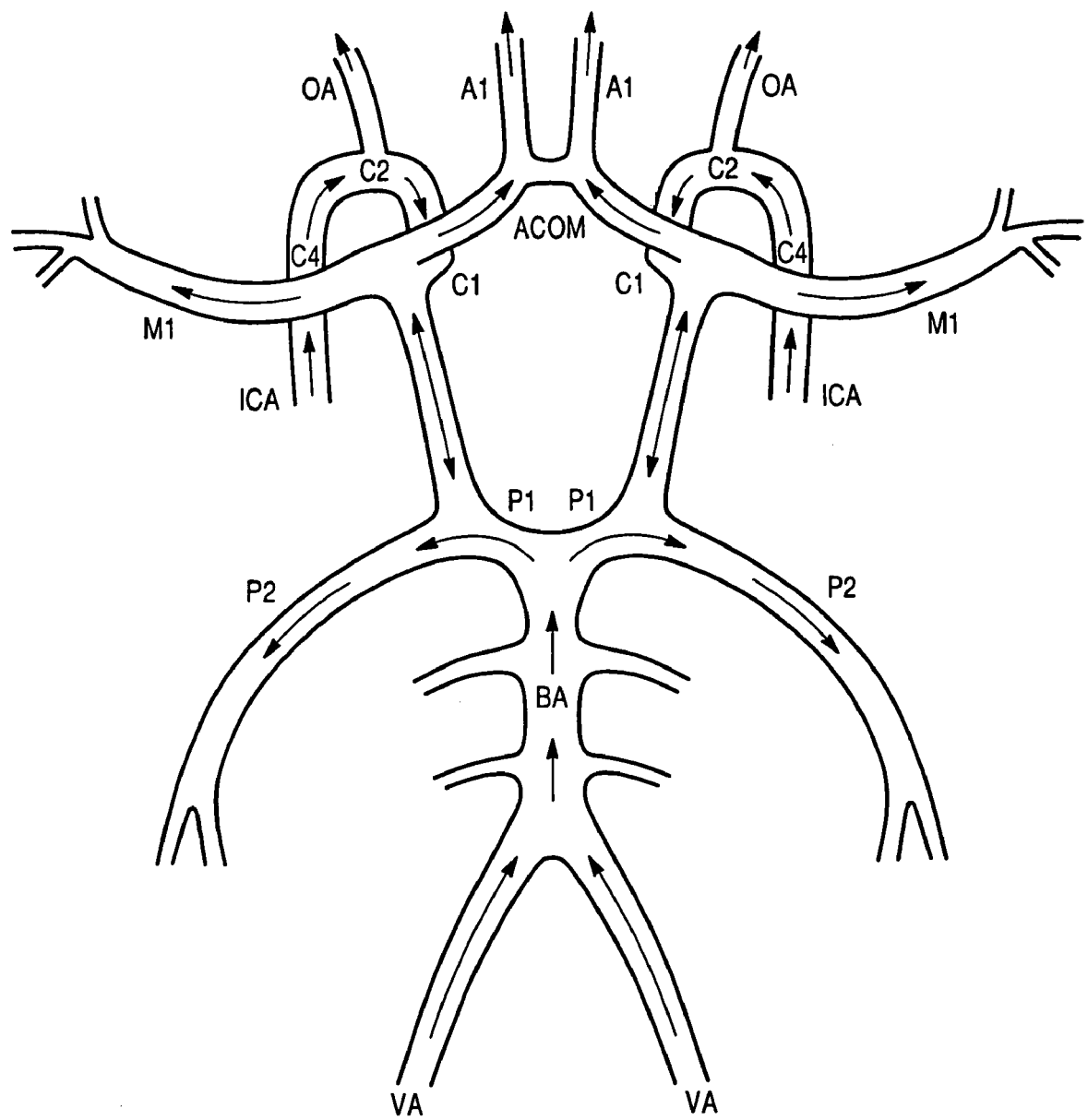

The 19 intracranial vessel segments considered are depicted in FIGS. 33 and 34. The vessel segments depicted in FIGS. 33 and 34 represent the left and right vertebral artery (VA), basilar artery (BA), posterior cerebral artery/PCA t (towards) (P1), posterior cerebral artery/PCA a (away) (P2), internal carotid artery/ICA t (towards) (C1), middle cerebral artery (M1), anterior cerebral artery (A1), anterior communicating artery (ACOM), carotid siphon (towards) (C4), carotid siphon (away) (C2), and the ophthalmic artery (OA).

I. Stent Placement

In accordance with an embodiment of the invention, DVA may be used identify and localize the need, placement and efficacy of a stent after it is placed. In addition to being used to determine the need for a stent, DVA can be used to monitor and analyze downstream vessel performance in evaluating the effectiveness of the stent and/or whether additional or other types of stents are required. This process differs from traditional stenting procedures in that traditional procedures only treat individual points of stenosis thereby potentially missing more appropriate upstream vessel segments having downstream stenotic effects, but that are themselves not yet fully stenotic (i.e., the stent could or should more appropriately be used on an upstream vessel segment that's becoming imminently stenotic). Under such circumstances it is also important to be able to use drug-impregnated stents at an upstream point because the pathogenesis at the downstream point of stenosis may not be sufficiently advanced and therefore could be reversed with the use of a medicinally impregnated stent. Furthermore, optimized stent placement helps minimize the need for (and indeed the damage caused by) angioplasty as a first alternative for clearing vessel blockages. Accordingly, use of DVA-assisted stenting procedures as described herein can expand the number of approved stent indications.

Since DVA provides a highly sensitive means for thoroughly assessing the hemodynamics of the cerebral vascular system, it can particularly identify lesion types in the cerebral vascular system with better specificity than traditional angiography. As such, DVA enables and facilitates the use of stents intended to effect coronary circulation into the cerebrovascular system by way of the carotid artery and associated vessels as well as into other vascular systems of other organs. For example, DVA facilitates the use of stents to treat non-surgically accessible internal carotid artery lesions that are at the base of the jaw or at an entrance into the skull. Similarly, DVA-assisted stent placement can be used in areas with lesions causing significant diminution of flow to the brain stem (e.g., lesions within the basal artery).

Figure 35:
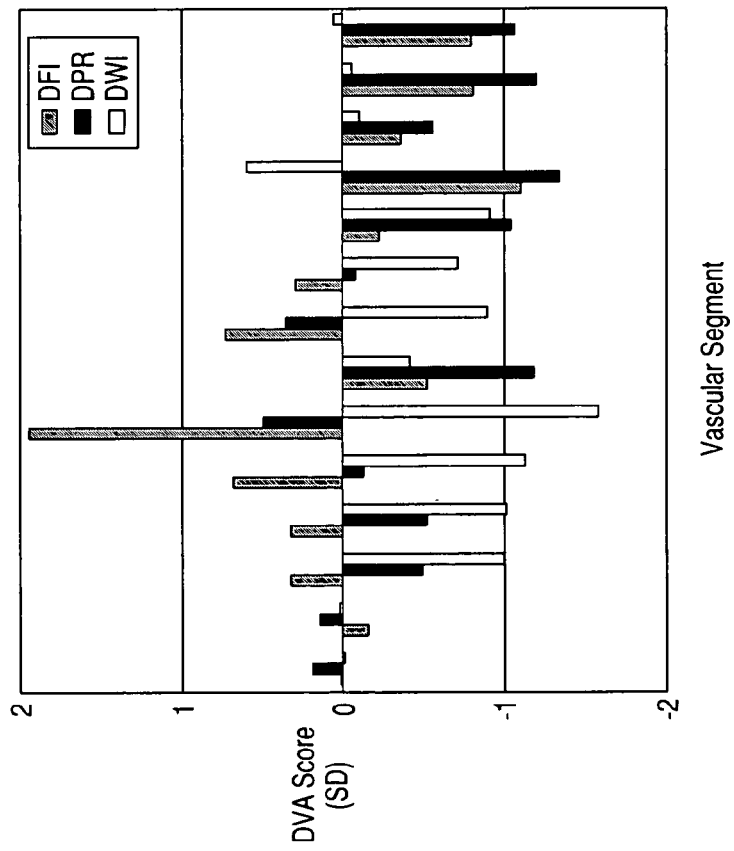
FIGS. 35a and 35b depict the pre-stenting and post-stenting of effects of revascularization procedures.

Indeed, as described in FIGS. 35A and 35B, DVA-assisted stenting procedures are useful for evaluating the global effects of a stenting procedure. In FIG. 35, it can be observed that both a localized and global increase in flow can be observed after a revascularization procedure (i.e., after stenting or angioplasty). Thus, DVA-assisted stenting procedures enable a treating physician to dynamically observe both the localized and system-wide effects of a stenting procedure. Importantly, a global perspective also enables the treating physician to treat and manage the global flow increase that will likely be associated with stent implantation.

In accordance with another embodiment of the invention, DVA is used to monitor the effects of emboli (which can then cause infarction) associated with stent placement. Since stent placement (and angioplasty) inherently result in tissue damage and emboli formation, the incidence of emboli associated with such procedures must be monitored, and if possible, minimized. Accordingly, DVA can be used to identify a potential lesion before a full stenosis has occurred allowing a stent to be placed therapeutically and without angioplasty. Similarly, DVA enables the treating physician to estimate the likelihood of emboli occurrence associated with stent placement at a particular location before undertaking an invasive procedure. Thus, DVA-assisted stent placement allows a treating physician to balance the benefits of stent placement at a particular location against the risks due to emboli formation associated with that specific location.

Figure 36:
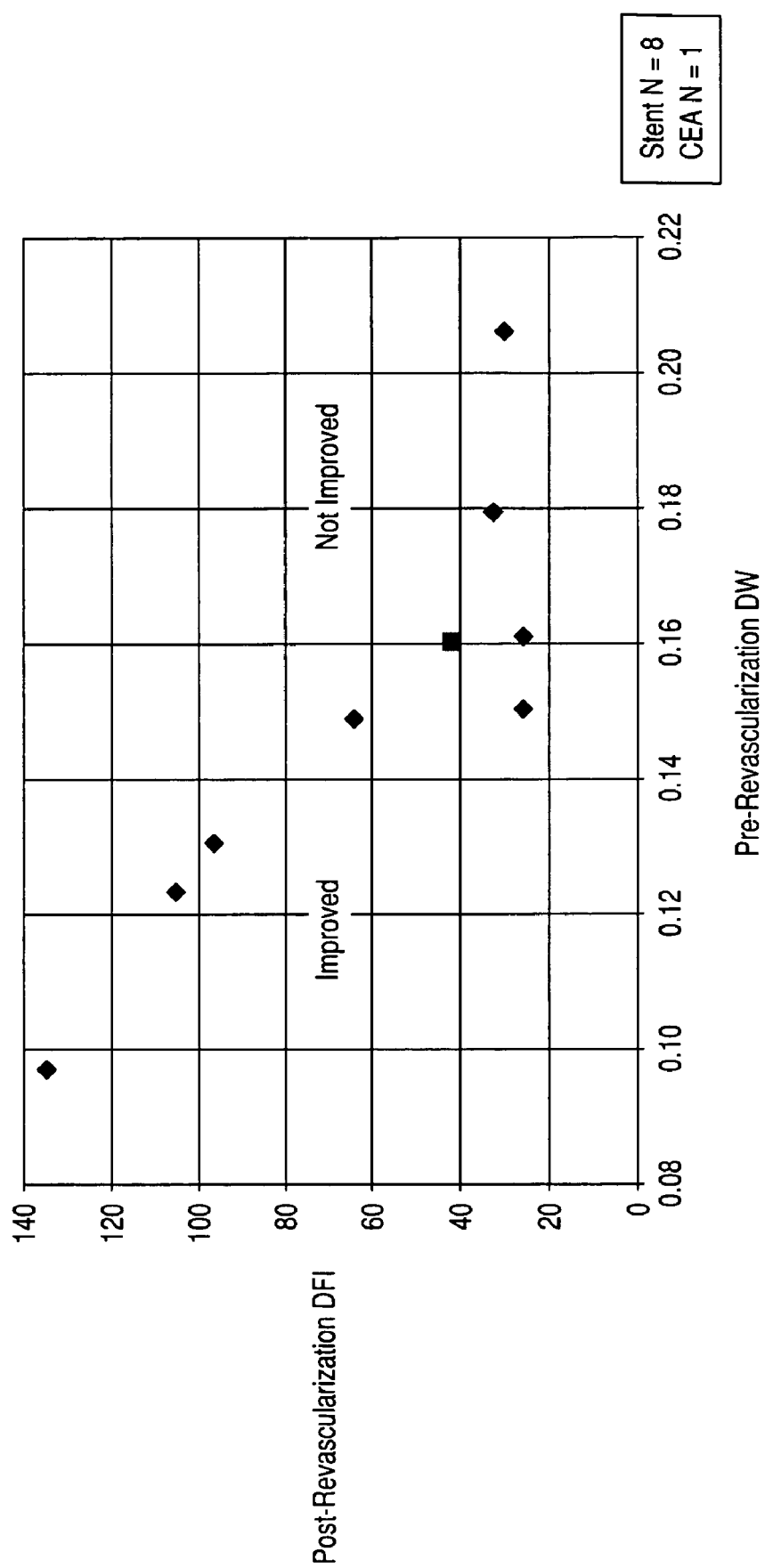
FIG. 36 is a plot of DWI versus DFI values following stenting procedures.

In particular, it has been observed that the DVA measured Dynamic Work Index (DWI) is predictive of the microcirculatory effect of stent placement at a particular vessel site. As depicted in FIG. 36, a plot of DWI versus DFI can predict the likely effects of carotid stenting (and thus allows a treating physician to balance the potential risks and benefits from stenting procedure prior to surgical intervention). In particular, it was observed that there is little benefit to be gained from performing a stenting procedure on patients with DWI values above approximately 0.16 due to excessive perfusion and the potential effects of emboli formation. Similarly, it appears that patients with DWI values below approximately 0.10 have little need for a stenting procure (i.e., there is minimal if any flow impedance). Finally, the data reveals that patients with DWI values between approximately 0.10 and 0.16 obtain maximum benefits from stenting procedures when offset against the potential effects of emboli.

In accordance with another embodiment of the invention, DVA-assisted stenting procedures are used to manage the incidence of induced hyperemia occurring after a stenting procedure by enabling staged (or stepped) stent expansion. Pathological hyperemia refers to the breakthrough increase in flow following any revascularization (i.e., stenting) procedure. Downstream vessels are particularly susceptible to such effects because they may have become weakened or atrophied (e.g., decreased elasticity) due to minimal performance demands during the time period (which may cover many years) in which flow has been diminished.

Staged (or stepped) DVA-assisted stenting procedures allow the treating physician to gradually expand the stent diameter after it has been placed inside the target vessel. In addition to minimizing the trauma associated with the initial implantation (i.e., emboli occurrence), Staged stenting permits the treating physician to regulate the increase in blood flow as the stent is expanded. Since DVA is a dynamic process that produces real time results, it can readily be used to simultaneously monitor the reaction of down stream vessels in response to gradually expanding stent (and thus minimize any risks associated with the increasing flow).

Figure 37:
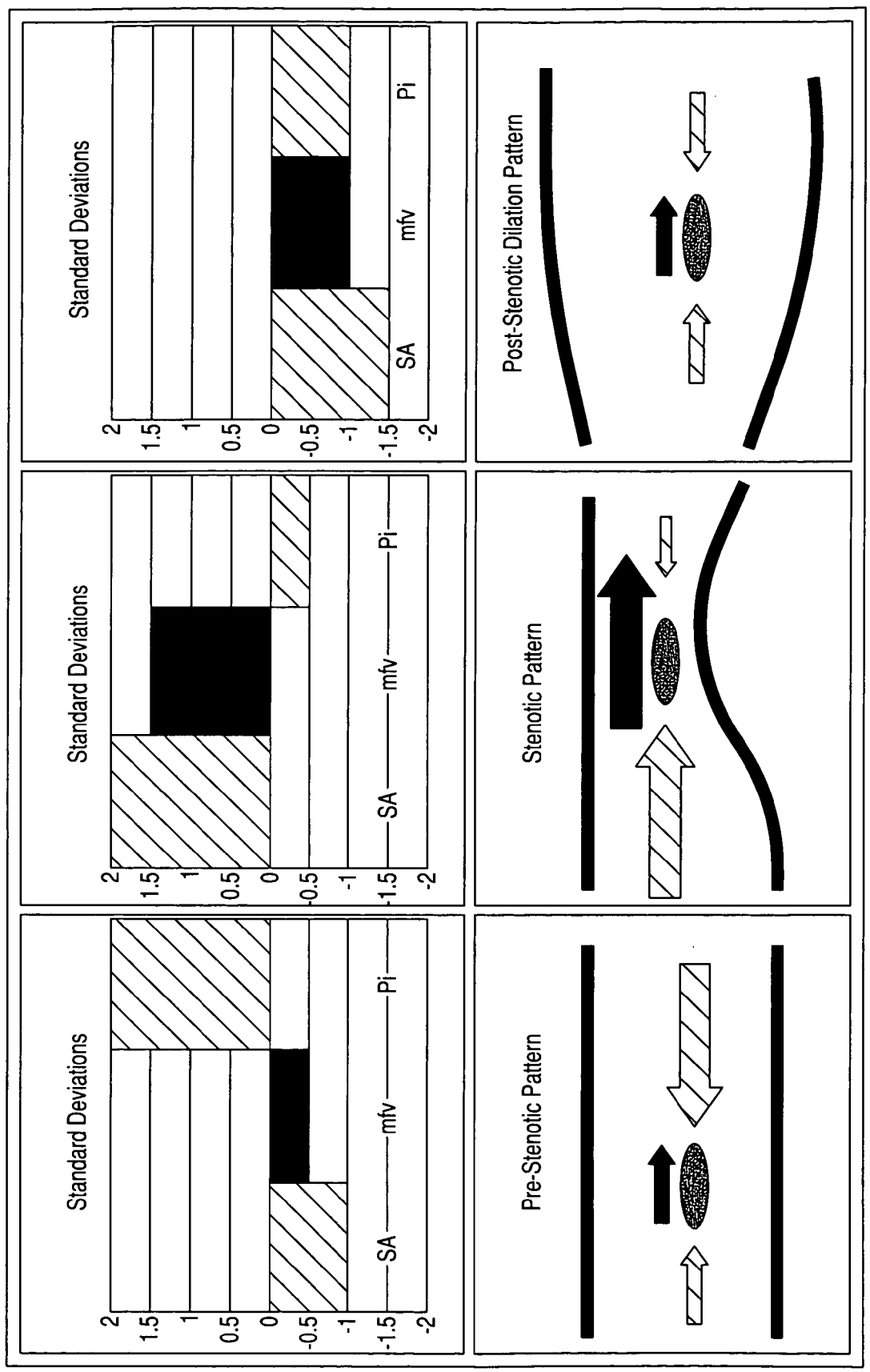
FIG. 37 depicts IVUS measured effects on flow at vascular regions proximate to an area of stenosis.

In accordance with another embodiment of the invention, DVA-assisted stenting can be used to enable and/or assist thin wire intravascular ultrasound (IVUS) procedures. For example, a thin wire IVUS device can be pulled across a stented vascular region whereby it passes through the pre-stent, stented and post-stent areas. As depicted in FIG. 37, when data is evaluated following such a procedure, three distinct vectors representing the net effect on flow can be observed. This type of data is particularly important as part of, among other things, bifurcation procedures and studies. Bifurcation procedures and studies entail stenting a blocked vessel and monitoring a second ancillary vessel that shares a common blood supply and determining whether the increase in flow in the blocked vessel (due to stent implantation) impacts flow in the non-blocked vessel.

II. Stent Design, Marketing and Selection

DVA may also be used to enable new ways of using, marketing and selling stents to the medical community. Specifically, DVA-assisted stenting assists the marketing and design of new stents and helps optimize stent selection based on a patient's condition. DVA can also be used to evaluate and validate new indications for existing or newly designed stents, including for conducting clinical stent trials.

In accordance with another embodiment of the invention, DVA-assisted stenting can be used to enhance the pulsatile movement of blood in stenotic regions and/or selectivity tailor stent design and selection based on individual patient needs. In particular, DVA-assisted stenting permits a treating physician to tailor (or otherwise) optimize stent selection with regard to a wide number of patient variables, including, among other things, the propensity for re-stenosis, the presence of tandem lesions, the vulnerability to the effects of emboli, the location of the lesion (e.g., at or near a bifurcation) and the overall risk-benefit ration associated with the stenting procedure. Currently, it is not possible to foresee, prior to stent implantation, how a stenting a particular vessel affects the dynamic components of pulsatile blood flow. For example, it is not known what a stent does to the pulsatile and laminar components of blood flow.

It is generally presumed that angioplasty substantially damages any remaining smooth muscle at the point of stenosis. As such, after angioplasty procedures, there is no smooth muscle in the immediate stenotic area available to contribute to the perpetuation of the pulsatile wave. Thus, it is highly advantageous to design a stent that can mimic smooth muscle within the immediate stenotic areas (i.e., a stent that can perpetuate the pulsatile wave better and preserve the contribution to the pulsatile wave made by the smooth muscle adjacent to the stenotic area). Thus, DVA-assisted stenting protocols can aide in the design and development of stents with durable elastic properties that better match the vessel wall tension at the point of placement. In turn, such stents would also have improved drug delivery characteristics (in fact, the drug elution profile of such stents can be evaluated by DVA as a function of vascular performance at points downstream from the stent).

DVA-assisted stenting also enables custom tailoring of stents to meet individual patient needs. For example, a stent can be tailored for a particular patient containing that contains a unique chemical(s) to address a particular condition (e.g., a particular type of arteriosclerotic plaque) and that has been individually sized for a specific vessel segment and in view of that vessel's condition and pliability. Thereafter, DVA can be used to assess the performance of the stent after implantation and to determine whether a different chemical agents vis a vis different types of plaque should administered. Indeed, it is envisioned that such stents could be designed to include, for example, crystalline materials capable of generating a Doppler signal such that the stent could be detected and interrogated by DVA (and thereby be self-reporting).

In accordance with another embodiment of the invention, DVA-assisted stenting can facilitate formal FDA approval for the use of coronary stents in non-coronary vascular beds. Generally, the stents used in the coronary vascular system can gain relatively quick FDA approval. Despite this approval, many approved coronary vascular system stents have been used by angiographers, cardiologists, and invasive radiologists for "off-label" treatment of, among other things, cerebrovascular lesions in a variety of vessel beds and vascular systems. In fact, such "off-label" uses of coronary vascular system stents in other vessel beds are becoming more frequent for the treatment of cerebrovascular disease.

Given the increasing frequency of "off label" use of coronary stents for the treatment of cerebrovascular conditions (as well as other blood flow conditions), DVA-assisted stenting provides a reliable means for measuring the efficacy of such regimens. Thus, DVA-assisted stenting provides a means for designing, marketing and establishing the utility of coronary (as well as newly designed non-coronary) stents to be used in a variety of organ beds including, among others, the cerebrovascular circulatory system, the carotid artery cerebrovascular bed, the peripheral vascular beds, and even the gastrointestinal vascular beds. Indeed, DVA can be used to support clinical trials by identifying lesions that would be amendable to the placement of coronary stents in non-coronary vascular beds. Accordingly, DVA-assisted stenting may facilitate obtaining formal FDA approval for the use of coronary or newly designed stents in non-coronary vascular beds.

The invention claimed is:

1. A method of assisting a stenting procedure in a human or an animal, comprising the steps of:
    obtaining a first set of intracranial blood flow data from a patient;
    generating blood flow factor values from said first set of blood flow data, the blood flow factor values including at least a value for mean blood flow velocity and a value for systolic acceleration;
    correlating said blood flow factor values;
    assessing blood flow based upon said correlated blood flow factor values; and
    inserting a stent at a location within a lumen, the location being based upon the assessed blood flow.

2. The method of claim 1, wherein said stent is expanded in stages.

3. The method of claim 1, wherein said steps of obtaining a first set of blood flow data, generating at least two blood flow factor values from said first set of blood flow data, correlating said at least two blood flow factor values and assessing blood flow at least on said correlated blood flow factor values occur before inserting the stent.

4. The method of claim 1, further comprising performing the steps of obtaining a second set of blood flow data, generating at least two blood flow factor values from said second set of blood flow data, correlating said at least two blood flow factor values and assessing blood flow at least on said correlated blood flow factor values after inserting the stent.

5. The method of claim 1, wherein said blood flow factor values also include at least one of a pulsatility index value, a natural logarithm of systolic acceleration value, a peak systolic velocity value, an end diastolic velocity value, a peak systolic time value, an end diastolic time value, an acceleration/mean flow velocity index value, a velocity/impedance index value and an acceleration/impedance index value.

6. The method of claim 5, further comprising the step of correlating at least three blood flow factor values.

7. The method of claim 1, wherein said step of obtaining intracranial blood flow data comprises use of emissive and reflective wave technology.

8. The method of claim 7, wherein said emissive and reflective wave technology includes ultrasound technology.

9. The method of claim 8, wherein said ultrasound technology includes Doppler technology.

10. The method of claim 8, wherein said ultrasound technology includes thin wire intravascular ultrasound technology.

11. The method of claim 7, wherein said emissive and reflective wave technology includes laser technology.

12. The method of claim 1, further comprising the step of generating a reference data set of correlated blood flow factor values.

13. The method of claim 1, further comprising the step of supplementing a reference data set of correlated blood flow factor values with additional correlated blood flow factor values and data.

14. The method of claim 1, further comprising the step of comparing said correlated blood flow factor values with a reference data set of correlated blood flow factor values.

15. The method of claim 1, further comprising the step of designing a stent.

16. The method of claim 15, further comprising the step of infusing a stent with at least one chemical composition.

17. The method of claim 15, further comprising the step of coating a stent with at least one chemical composition.

18. The method of claim 15, further comprising the step of inserting the blood flow factor values into a schema.

19. The method of claim 1, wherein the step of assessing blood flow based upon said correlated blood flow factor values includes evaluating the patient's anticipated reaction to a proposed treatment approach.

* * * * *

UNITED STATES PATENT AND TRADEMARK OFFICE
CERTIFICATE OF CORRECTION

PATENT NO. : 7,604,599 B2
APPLICATION NO. : 10/755208
DATED : October 20, 2009
INVENTOR(S) : Mozayeni et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1424 days.

Signed and Sealed this

Fifth Day of October, 2010

David J. Kappos
*Director of the United States Patent and Trademark Office*